(12) United States Patent
Medeiros et al.

(10) Patent No.: US 11,559,372 B2
(45) Date of Patent: Jan. 24, 2023

(54) PATIENT-MOUNTED SURGICAL RETRACTOR

(71) Applicant: Medos International Sarl, Le Locle (CH)

(72) Inventors: Andrew Medeiros, Fall River, MA (US); Zoher Bootwala, Foxboro, MA (US); Nicholas Miller, Raynham, MA (US); Roman Lomeli, Plymouth, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 124 days.

(21) Appl. No.: 16/139,434

(22) Filed: Sep. 24, 2018

(65) Prior Publication Data

US 2019/0090864 A1 Mar. 28, 2019

Related U.S. Application Data

(60) Provisional application No. 62/562,055, filed on Sep. 22, 2017, provisional application No. 62/562,046, filed on Sep. 22, 2017.

(51) Int. Cl.
*A61B 17/02* (2006.01)
*A61B 90/57* (2016.01)
(Continued)

(52) U.S. Cl.
CPC ............ *A61B 90/57* (2016.02); *A61B 17/025* (2013.01); *A61B 17/0206* (2013.01);
(Continued)

(58) Field of Classification Search
CPC ..... A61B 90/50; A61B 90/57; A61B 17/0206; A61B 17/025; A61B 2017/0256
See application file for complete search history.

(56) References Cited

U.S. PATENT DOCUMENTS

| 4,874,375 A | 10/1989 | Ellison |
|---|---|---|
| 5,728,046 A | 3/1998 | Mayer et al. |

(Continued)

FOREIGN PATENT DOCUMENTS

| CN | 101489497 A | 7/2009 |
|---|---|---|
| CN | 102821673 A | 12/2012 |

(Continued)

OTHER PUBLICATIONS

[No Author Listed] MIS Lateral Platform, "Surgical Technique Guide," DePuy Spine Inc., 2012 (29 pages).

(Continued)

*Primary Examiner* — Amy R Sipp
(74) *Attorney, Agent, or Firm* — Barnes & Thornburg LLP

(57) ABSTRACT

Surgical tissue retraction systems and methods are described herein. Such systems and methods can be employed in some embodiments to provide medial-lateral tissue retraction to increase access to a surgical site. In one embodiment, a surgical instrument can include a body configured to couple to an implantable anchor, a first tissue manipulating implement coupled to the body and capable of polyaxial movement relative thereto, and a second tissue manipulating implement coupled to the body and capable of polyaxial movement relative thereto. Further, the first and second tissue manipulating implements can be opposed to one another such that they can move any of toward and away from one another.

11 Claims, 92 Drawing Sheets

(51) Int. Cl.
*A61B 90/60* (2016.01)
*A61B 17/70* (2006.01)
*A61B 90/50* (2016.01)
*A61B 17/29* (2006.01)
*A61B 17/86* (2006.01)
*A61B 90/00* (2016.01)
*A61B 17/00* (2006.01)

(52) U.S. Cl.
CPC .......... *A61B 17/29* (2013.01); *A61B 17/7032* (2013.01); *A61B 17/7076* (2013.01); *A61B 17/7077* (2013.01); *A61B 90/50* (2016.02); *A61B 90/60* (2016.02); *A61B 17/8625* (2013.01); *A61B 2017/003* (2013.01); *A61B 2017/00398* (2013.01); *A61B 2017/0256* (2013.01); *A61B 2090/062* (2016.02); *A61B 2090/571* (2016.02)

(56) References Cited

U.S. PATENT DOCUMENTS

| | | | |
|---|---|---|---|
| 5,902,233 A * | 5/1999 | Farley | A61B 17/0206 600/213 |
| 5,931,777 A * | 8/1999 | Sava | A61B 17/02 600/210 |
| 5,944,658 A | 8/1999 | Koros et al. | |
| 6,083,154 A * | 7/2000 | Liu | A61B 17/0293 |
| 6,869,398 B2 | 3/2005 | Obenchain et al. | |
| 6,951,538 B2 | 10/2005 | Ritland | |
| 7,014,608 B2 | 3/2006 | Larson et al. | |
| 7,179,261 B2 | 2/2007 | Sicvol et al. | |
| 7,491,168 B2 | 2/2009 | Raymond et al. | |
| 7,918,792 B2 | 4/2011 | Drzyzga et al. | |
| 7,959,564 B2 | 6/2011 | Ritland | |
| 8,182,519 B2 | 5/2012 | Loftus et al. | |
| 8,202,216 B2 | 6/2012 | Melkent et al. | |
| 8,357,184 B2 | 1/2013 | Woolley et al. | |
| 8,394,109 B2 | 3/2013 | Hutton et al. | |
| 8,409,087 B2 | 4/2013 | Ames et al. | |
| 8,435,269 B2 | 5/2013 | Woolley et al. | |
| 8,469,960 B2 | 6/2013 | Hutton et al. | |
| 8,535,320 B2 | 9/2013 | Woolley et al. | |
| 8,636,655 B1 | 1/2014 | Childs | |
| 8,668,715 B2 | 3/2014 | Sandhu | |
| 8,882,661 B2 | 11/2014 | Hutton et al. | |
| 8,894,573 B2 | 11/2014 | Loftus et al. | |
| 8,900,137 B1 | 12/2014 | Lovell et al. | |
| 8,911,442 B2 | 12/2014 | Wing et al. | |
| 8,974,381 B1 | 3/2015 | Lovell et al. | |
| 9,050,146 B2 | 6/2015 | Woolley et al. | |
| 9,216,016 B2 | 12/2015 | Fiechter et al. | |
| 9,307,972 B2 | 4/2016 | Lovell et al. | |
| 9,386,971 B1 | 7/2016 | Casey et al. | |
| 9,414,828 B2 | 8/2016 | Abidin et al. | |
| 9,572,560 B2 | 2/2017 | Mast et al. | |
| 9,615,818 B2 | 4/2017 | Baudouin et al. | |
| 9,649,099 B1 | 5/2017 | Casey et al. | |
| 9,693,762 B2 | 7/2017 | Reimels | |
| 9,700,293 B2 | 7/2017 | Cryder et al. | |
| 9,801,667 B2 | 10/2017 | Hawkes et al. | |
| 9,844,400 B2 | 12/2017 | Stevenson et al. | |
| 9,907,583 B2 | 3/2018 | Hayes | |
| 10,792,168 B2 | 10/2020 | Malcolmson et al. | |
| 2004/0230191 A1 | 11/2004 | Frey et al. | |
| 2005/0131408 A1 | 6/2005 | Sicvol et al. | |
| 2005/0131422 A1 | 6/2005 | Anderson et al. | |
| 2005/0228400 A1 | 10/2005 | Chao et al. | |
| 2005/0245929 A1 | 11/2005 | Winslow et al. | |
| 2006/0052671 A1 | 3/2006 | McCarthy | |
| 2007/0093823 A1 | 4/2007 | Booth et al. | |
| 2007/0191955 A1 | 8/2007 | Zucherman et al. | |
| 2007/0213715 A1 | 9/2007 | Bridwell et al. | |
| 2008/0021285 A1 * | 1/2008 | Drzyzga | A61B 17/708 600/215 |
| 2008/0140120 A1 | 6/2008 | Hestad et al. | |
| 2008/0262318 A1 | 10/2008 | Gorek et al. | |
| 2009/0036746 A1 | 2/2009 | Blackwell et al. | |
| 2009/0093684 A1 | 4/2009 | Schorer | |
| 2009/0149885 A1 | 6/2009 | Durward et al. | |
| 2009/0187080 A1 | 7/2009 | Seex | |
| 2010/0317928 A1 | 12/2010 | Subramaniam | |
| 2011/0004248 A1 | 1/2011 | Abdou | |
| 2011/0034779 A1 * | 2/2011 | Louftus | A61B 17/7076 606/301 |
| 2011/0137345 A1 | 6/2011 | Stoll et al. | |
| 2012/0089150 A1 | 4/2012 | Smith | |
| 2012/0232350 A1 | 9/2012 | Seex | |
| 2013/0345755 A1 * | 12/2013 | Prajapati | A61B 17/7037 606/273 |
| 2014/0074166 A1 | 3/2014 | Scarrow et al. | |
| 2014/0194697 A1 | 7/2014 | Seex | |
| 2014/0277163 A1 | 9/2014 | Kretzer et al. | |
| 2014/0296917 A1 | 10/2014 | Donner et al. | |
| 2015/0148853 A1 | 5/2015 | Hawkes et al. | |
| 2015/0313585 A1 | 11/2015 | Abidin et al. | |
| 2016/0015433 A1 | 1/2016 | Jackson | |
| 2016/0030029 A1 | 2/2016 | Mahoney et al. | |
| 2016/0074029 A1 | 3/2016 | O'Connell et al. | |
| 2016/0106408 A1 | 4/2016 | Ponmudi et al. | |
| 2016/0296220 A1 | 10/2016 | Mast et al. | |
| 2016/0354073 A1 | 12/2016 | Nel et al. | |
| 2017/0035406 A1 | 2/2017 | Abidin et al. | |
| 2017/0105770 A1 | 4/2017 | Woolley et al. | |
| 2017/0135735 A1 | 5/2017 | Hawkes et al. | |
| 2017/0265850 A1 | 9/2017 | Cryder et al. | |
| 2019/0090979 A1 | 3/2019 | Medeiros et al. | |
| 2021/0196326 A1 | 7/2021 | Medeiros et al. | |

FOREIGN PATENT DOCUMENTS

| | | |
|---|---|---|
| CN | 103442656 A | 12/2013 |
| JP | 2009052813 A | 3/2009 |
| JP | 2017528197 A | 9/2017 |
| WO | 2010121291 A1 | 10/2010 |
| WO | 2016131077 A1 | 8/2016 |

OTHER PUBLICATIONS

[No Author Listed] [No Date Given] "NuVasive MAS TLIF Surgical Technique," (25 pages).
[No Author Listed] "NuVasive MAS TLIF 2 Surgical Technique," NuVasive Inc., 2016 (48 pages).
[No Author Listed] Pipeline Access System and CONCORDE, "Surgical Technique—Guide and Protect Catalogue," DePuy Spine Inc., 2011 (24 pages).
International Search Report and Written Opinion for Application No. PCT/IB18/57366, dated Jan. 18, 2019 (8 pages).
International Search Report and Written Opinion for Application No. PCT/IB18/57367, dated Jan. 29, 2019, (10 pages).
International Preliminary Report on Patentability for Application No. PCT/US2018/044631, dated Dec. 12, 2018 (10 pages).
International Search Report and Written Opinion for Application No. PCT/US2018/044631, dated Dec. 12, 2018 (15 pages).
[No Author Listed] "Click'X System Surgical Technique Guide," DePuy Spine Inc., 2015 (52 pages).
[No Author Listed] "Point to Point Minimally Invasive Retractor System Technique Guide," Synthes Spine, 2006 (24 pages).
Extended European Search Report for European Application No. 18858218.3, dated Jun. 2, 2021 (6 pages).
Japanese Office Action for Application No. 2020516705, dated Jun. 28, 2022 (10 pages).
Japanese Office Action for Application No. 2020516582, dated Jun. 21, 2022 (10 pages).
Chinese Office Action for Application No. 201880075167.0, dated Jul. 14, 2022 (17 pages).
Extended European Search Report for European Application No. 18857923.9, dated Feb. 24, 2022 (19 pages).

* cited by examiner

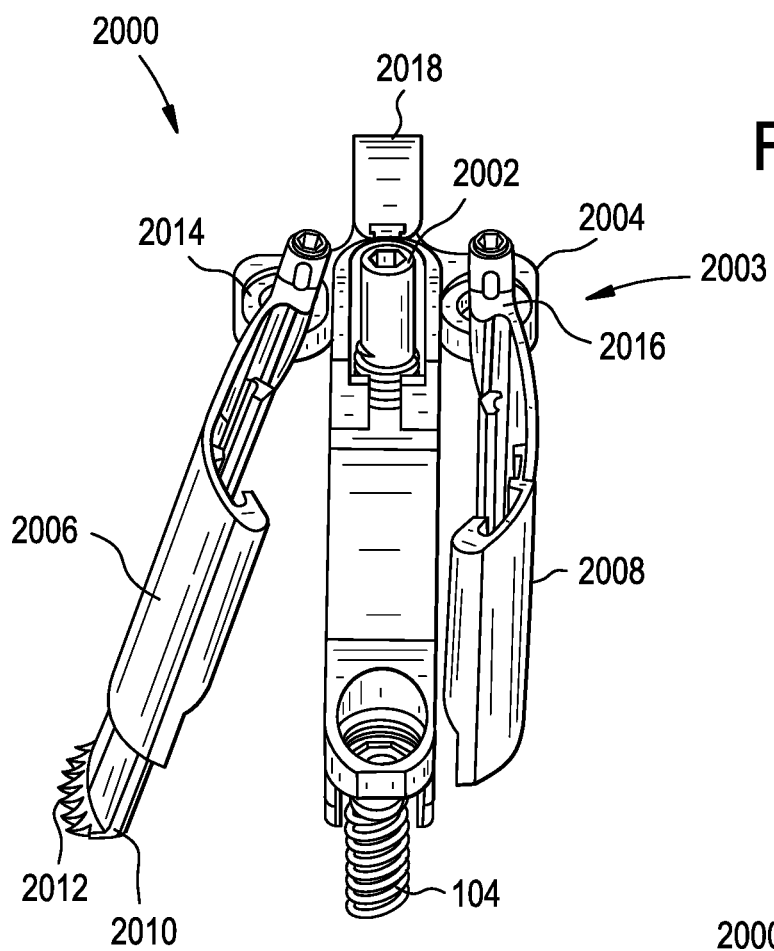
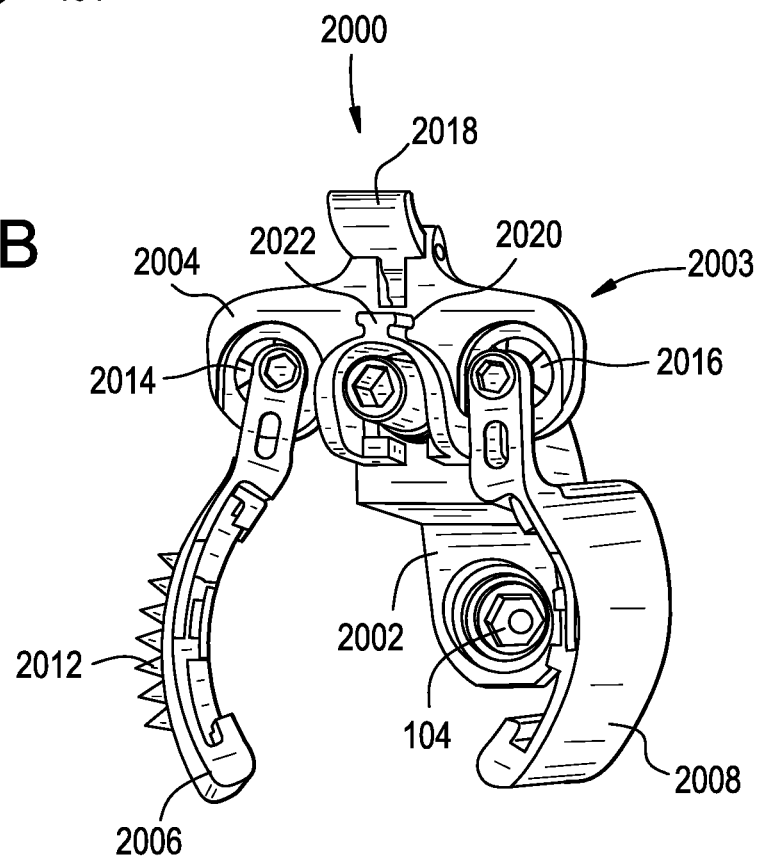
FIG. 20A
FIG. 20B

FIG. 22A
FIG. 22B
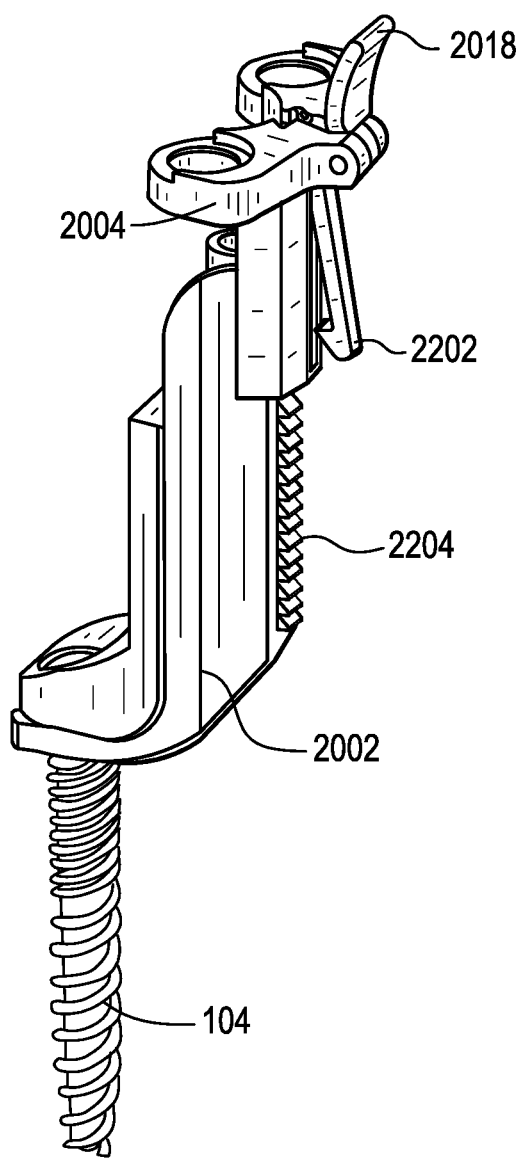
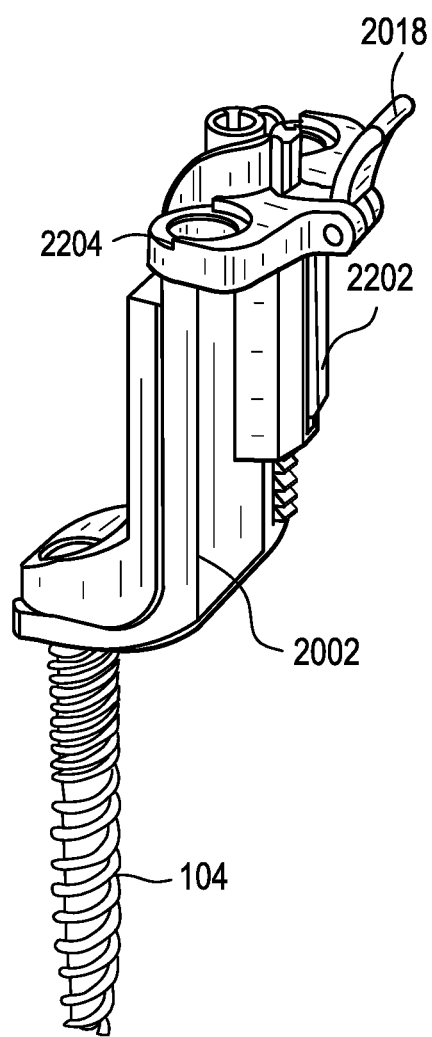

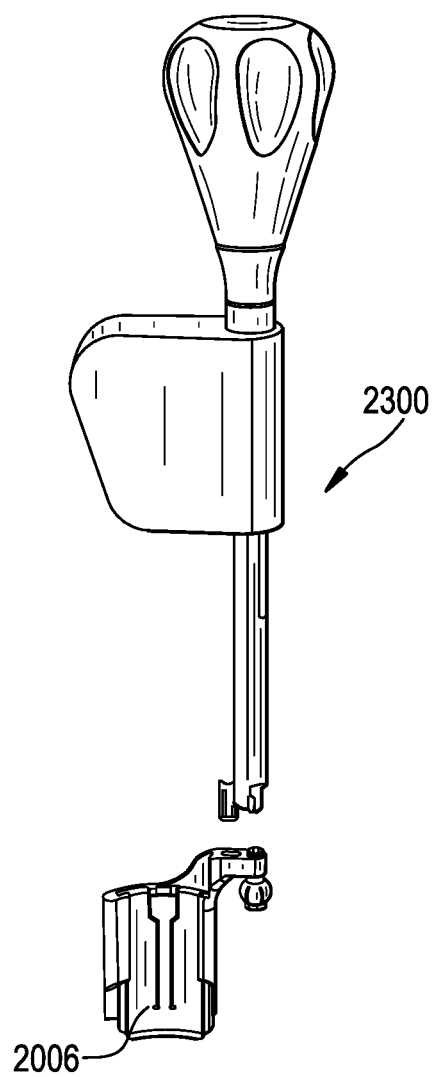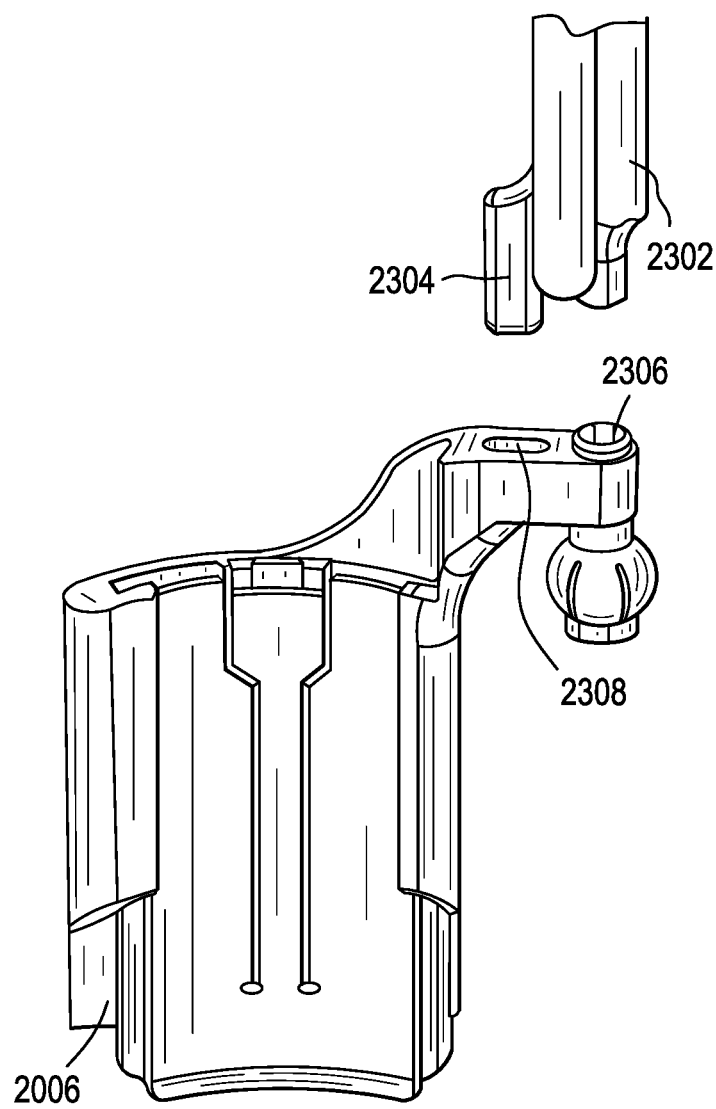

FIG. 24
FIG. 25
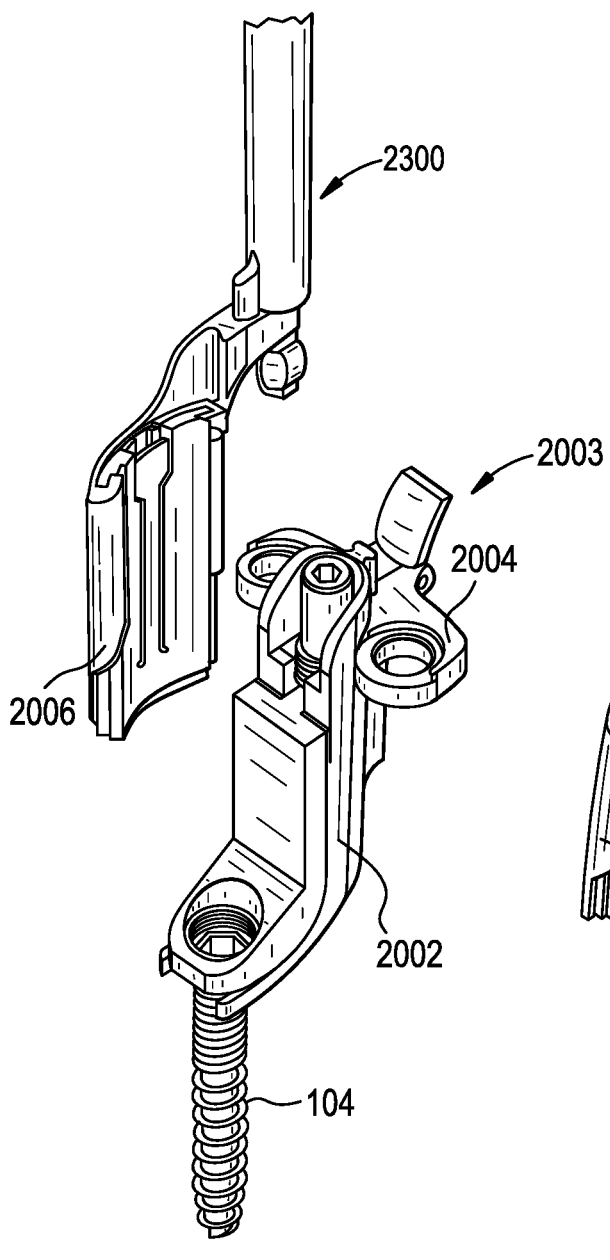
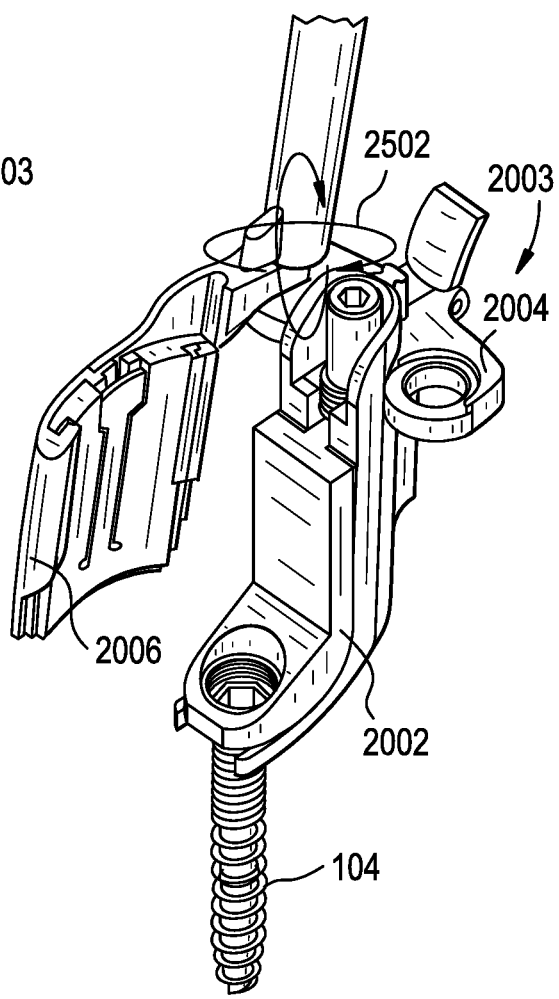

FIG. 26
FIG. 27
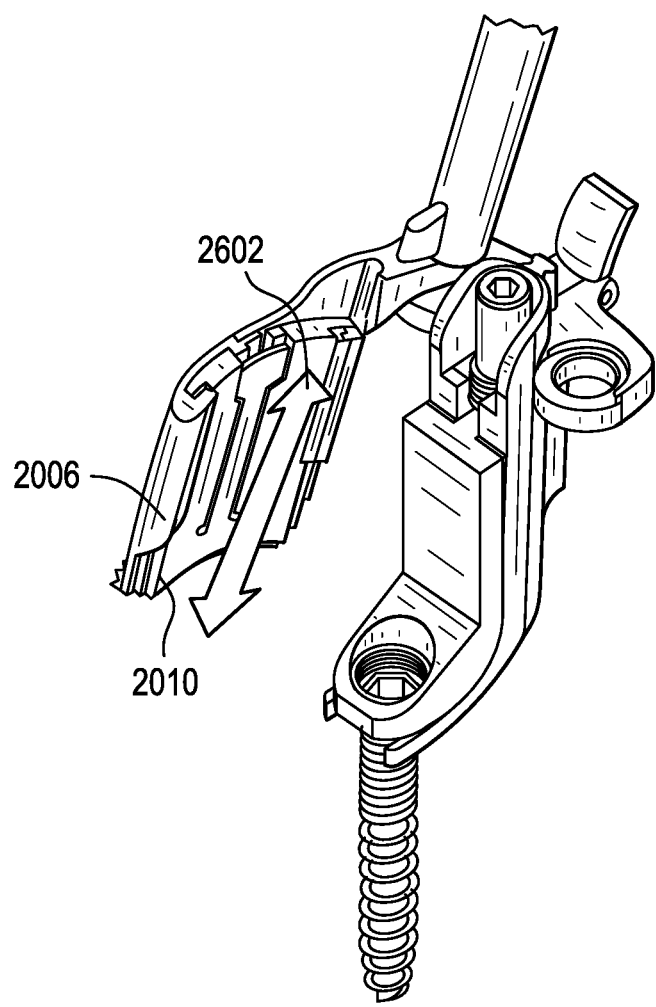
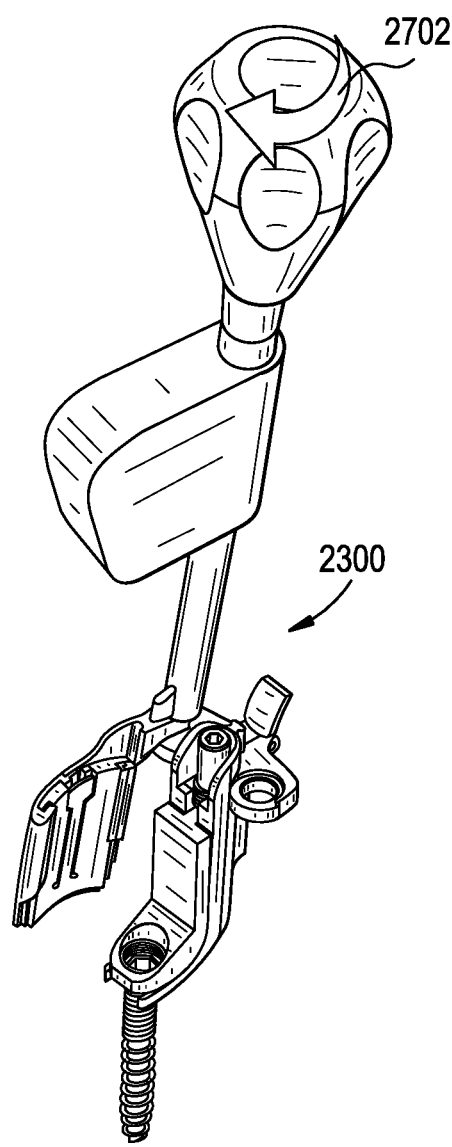

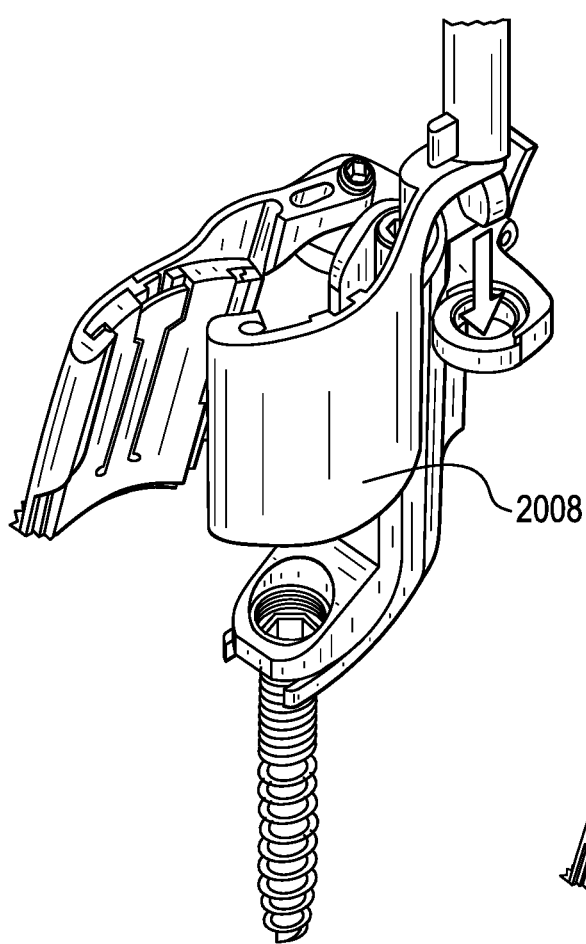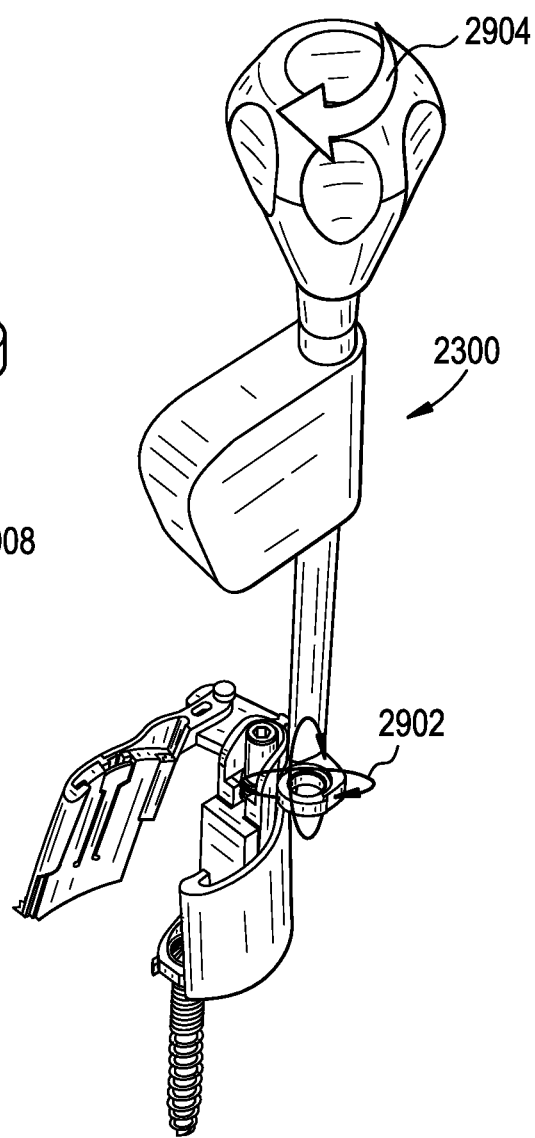

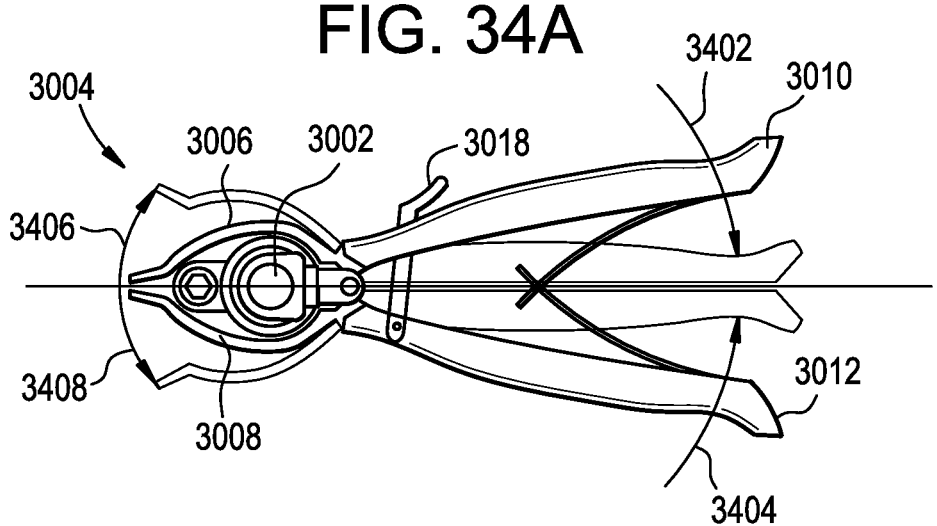
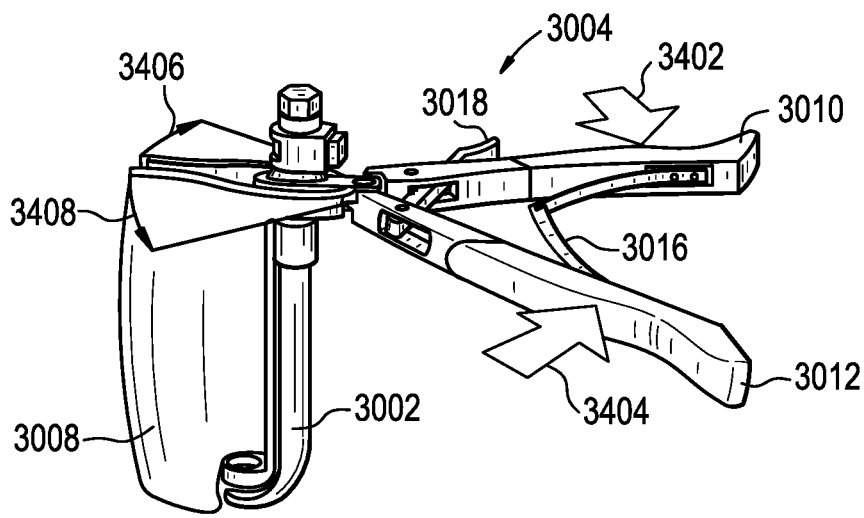
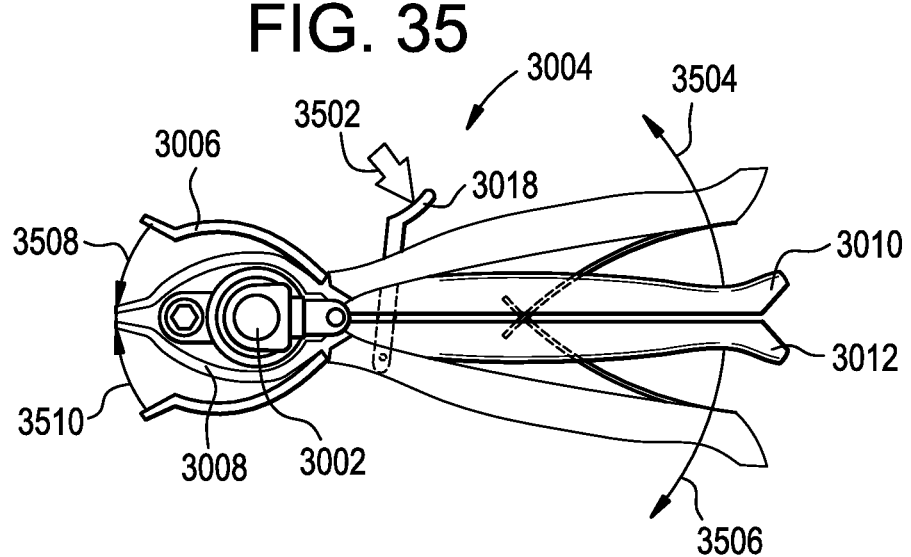

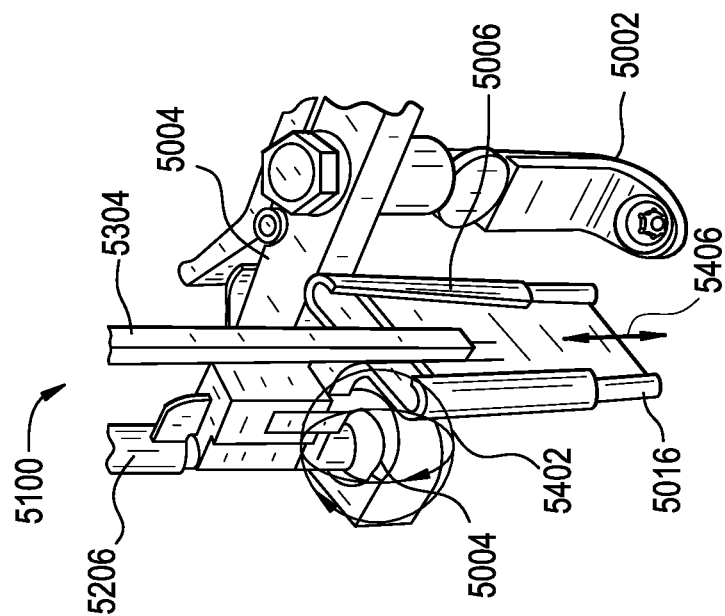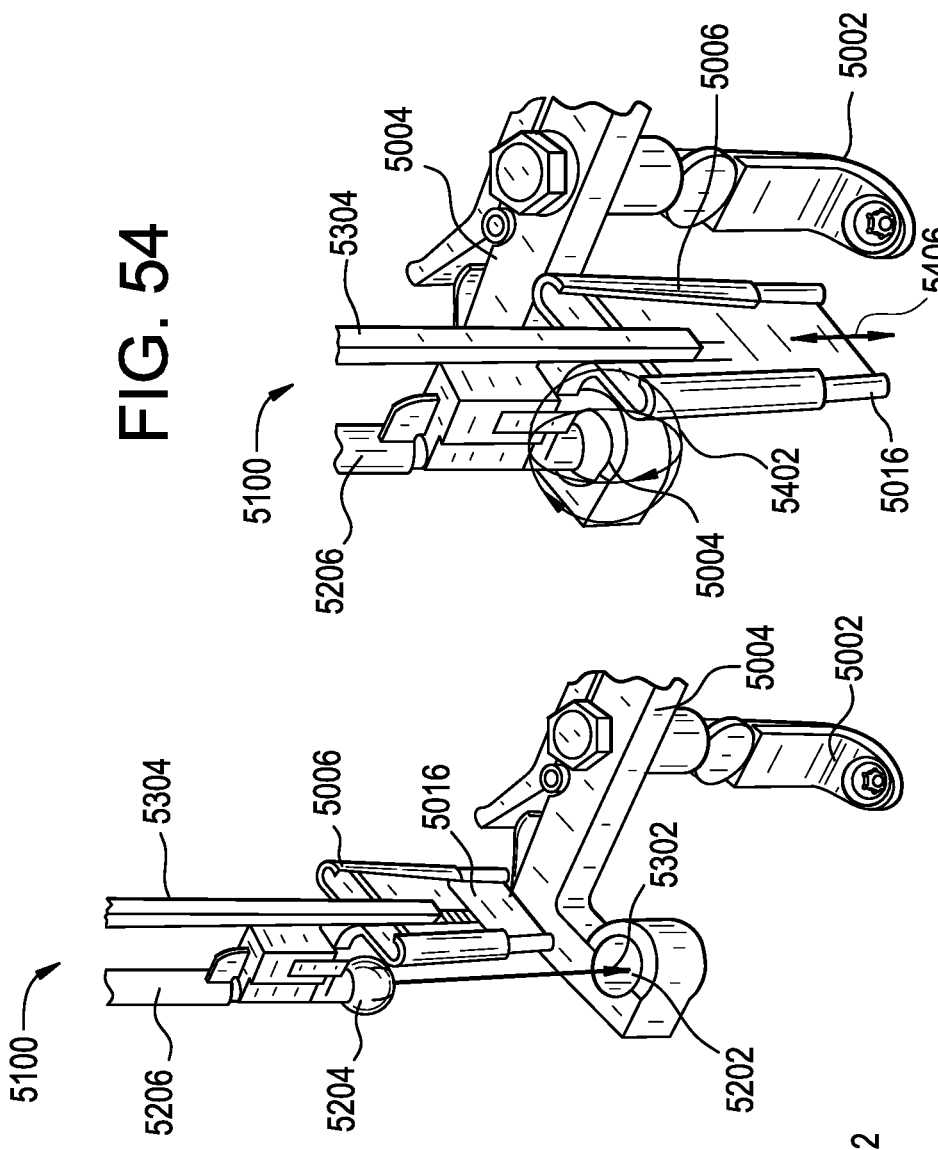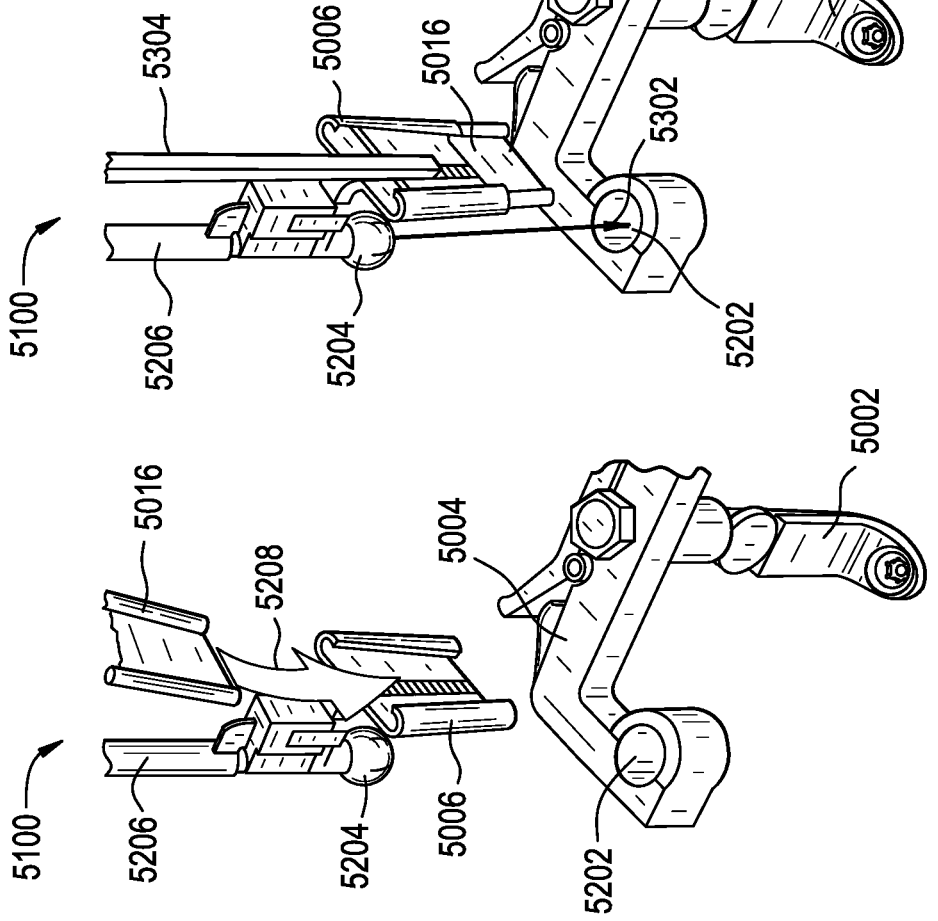

FIG. 66
FIG. 67
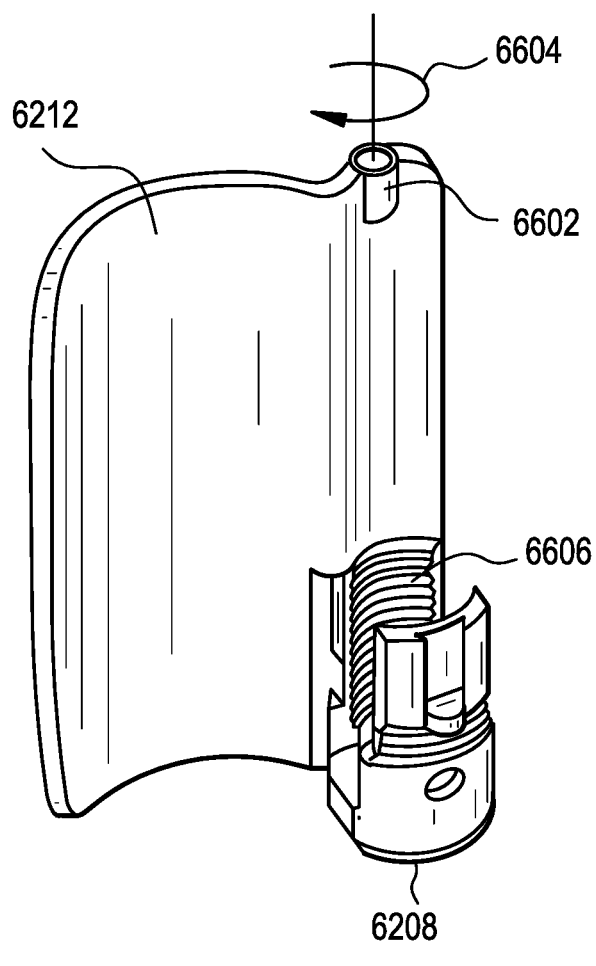
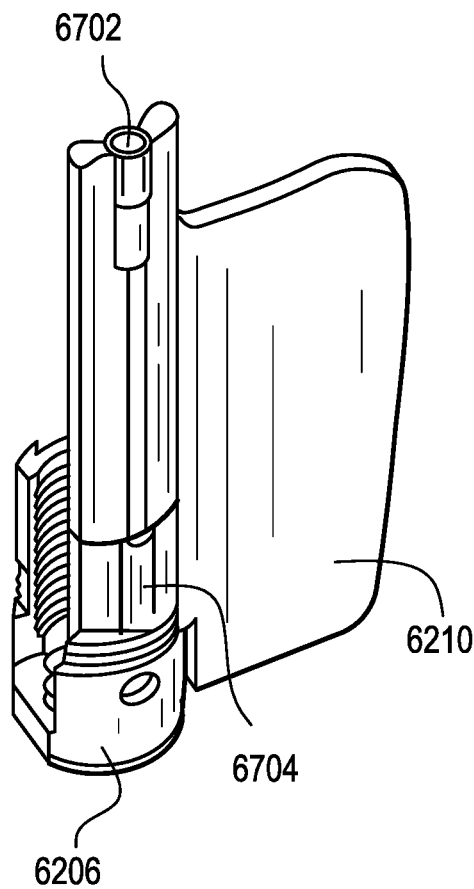

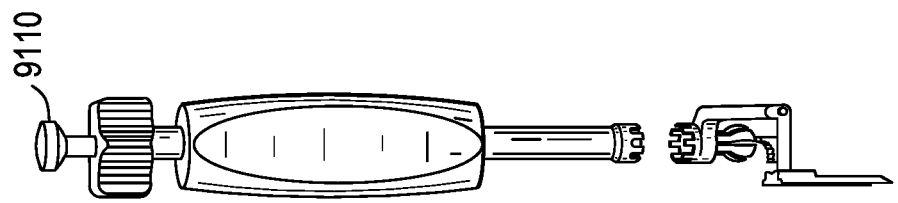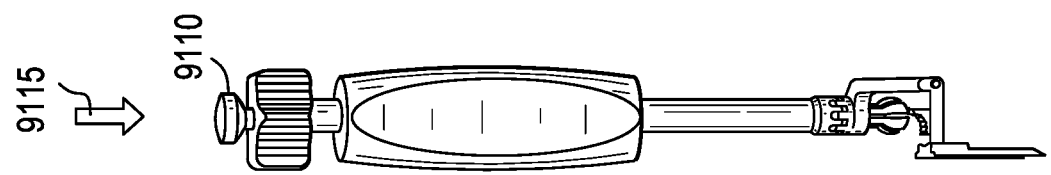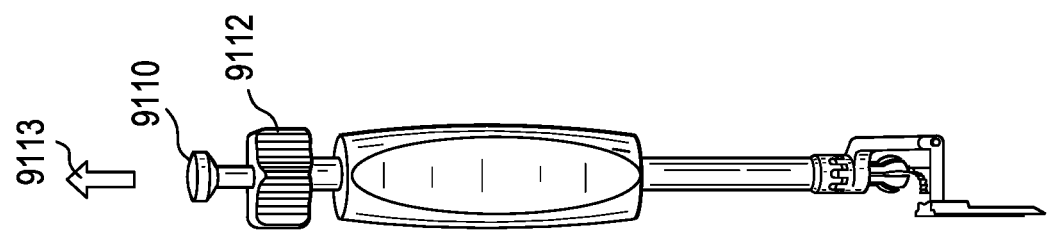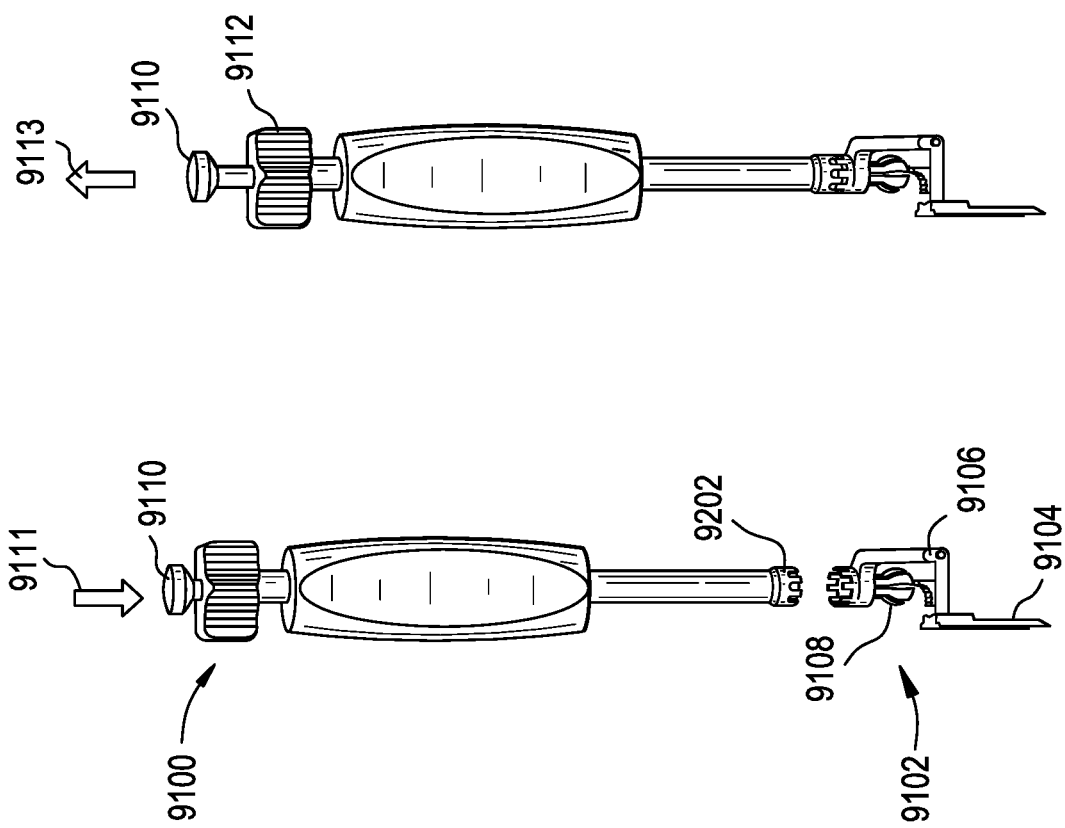

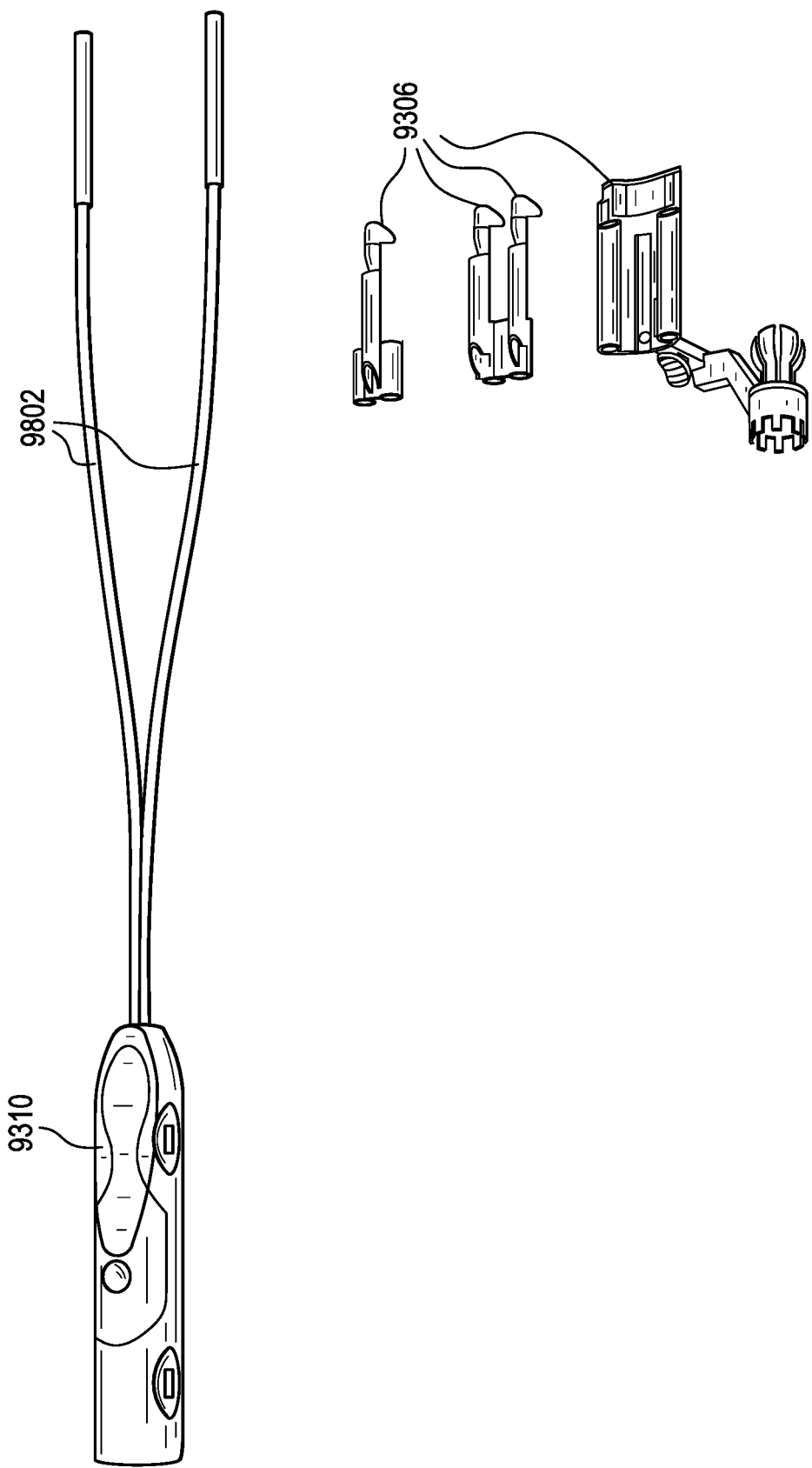

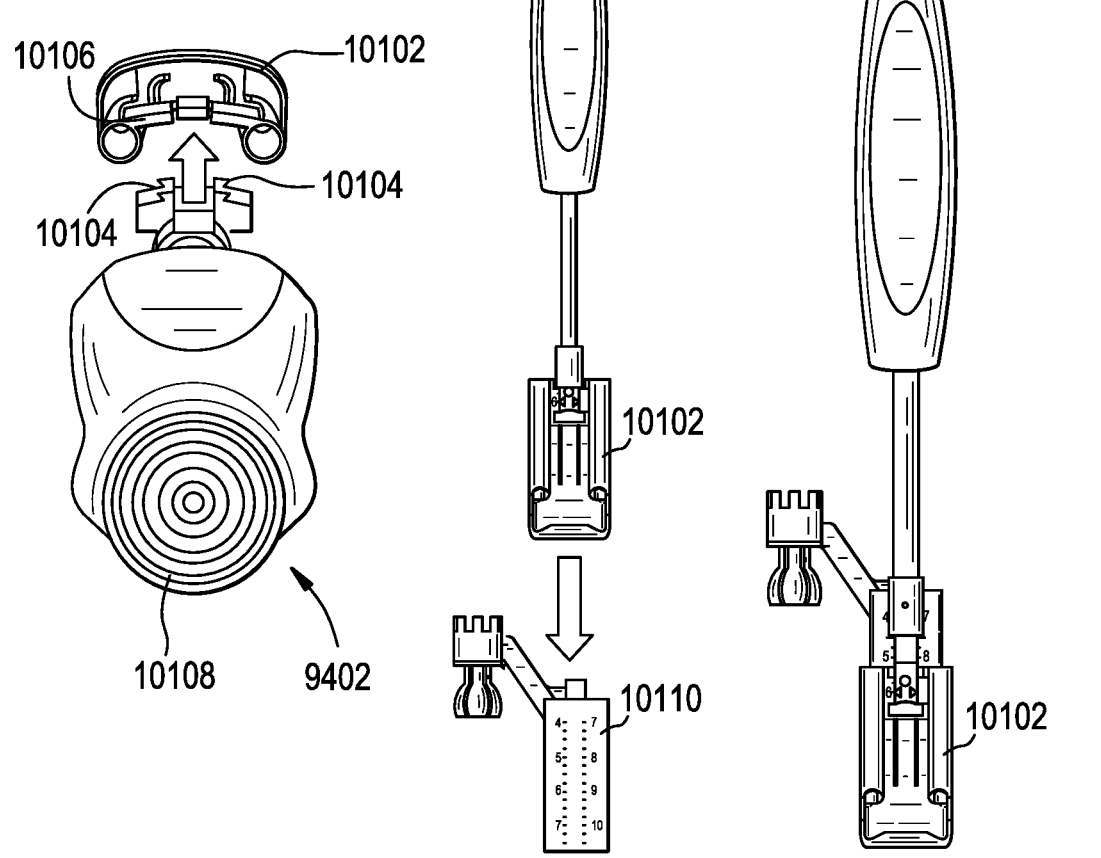

PATIENT-MOUNTED SURGICAL RETRACTOR

CROSS-REFERENCE TO RELATED APPLICATIONS

This application claims the benefit of U.S. Provisional Application Nos. 62/562,055 and 62/562,046, both filed on Sep. 22, 2017. The entire contents of each of these applications is incorporated herein by reference.

FIELD

This disclosure relates generally to surgical instruments, systems, and methods, and more particularly to instruments, systems, and methods for providing access to a surgical site using patient-mounted components. Such instruments, systems, and methods can be used in various procedures, e.g., orthopedic or neurologic surgical procedures such as spinal fusion surgery.

BACKGROUND

Surgical procedures are used to treat and cure a wide range of diseases, conditions, and injuries. Surgery often requires access to internal tissue through open or minimally invasive surgical procedures. The term "minimally invasive" refers to all types of minimally invasive surgical procedures, including endoscopic, laparoscopic, arthroscopic, natural orifice intraluminal, and natural orifice transluminal procedures. Minimally invasive surgery can have numerous advantages compared to traditional open surgical procedures, including reduced trauma, faster recovery, reduced risk of infection, and reduced scarring.

Whether minimally invasive or not, there are a number of surgical procedures in which it can be desirable to form a working channel in a patient to provide access to a surgical site within the patient. One such example is orthopedic or neurologic surgical procedures, including, e.g., spinal fusion procedures where it can be desirable to form a working channel through a patient's tissue to access their vertebrae and/or the intervertebral discs disposed between adjacent vertebrae.

A variety of methods for providing such a working channel are known, including various devices that are anchored to a surgical table upon which a patient is disposed, devices that penetrate tissue without being anchored to any other structure, or devices that anchor to a plurality of anchors implanted in a patient's bone. In such arrangements, the devices may be inadequately supported, may undesirably move relative to a patient if the patient moves relative to the operating table or some other external structure, or may impede a surgeon or other user in performing some aspect of a procedure.

By way of example, in spinal procedures involving operation on a patient's intervertebral disc disposed between adjacent vertebrae, access to the disc space can be difficult. Prior approaches can involve performing work on intervertebral discs before implanting pedicle screws in the adjacent vertebrae. Surgery on the intervertebral disc, however, can involve removal of portions of bone from the adjacent vertebrae, which can make subsequent implanting of pedicle screws more difficult. Implanting screws before removing vertebral bone can therefore be desirable, but surgeons cannot implant the pedicle screws with receiver heads before performing intervertebral disc work because the receiver heads (and extension posts typically coupled thereto) can block access to the intervertebral disc space. As a result, surgeons often resort to inserting guidewires for the pedicle screws, bending the guidewires away from the intervertebral space to perform disc operations around the guidewires, then implanting the pedicle screws.

The advent of modular pedicle screws can allow pedicle anchors to be implanted before performing intervertebral disc operations. This is because modular pedicle screws can include a lower-profile implantable anchor that can be implanted without impeding access to, e.g., an intervertebral disc. A spinal fixation element receiver can be coupled to the anchor after implantation and completion of any intervertebral disc operation. Such anchors can also provide a rigid access point indexed to the patient's anatomy.

Accordingly, there is a need for improved access devices, systems, and methods that can streamline the instrumentation and methodology of various surgical procedures. For example, there is a need for improved access devices, systems, and methods that can utilize anchors implanted in a patient's anatomy to support surgical instruments.

SUMMARY

In some embodiments, a patient-mounted surgical retractor is provided that can couple to an implanted anchor by way of, for example, a surgical support or extension that couples to the anchor. The retractor can include one or more tissue manipulating implements that can be configured to interface with tissue. In some embodiments, the retractor can include at least first and second opposed tissue manipulating implements that can be configured to move in a variety of manners, including various combinations of moving and/or pivoting toward and away from one another. For example, a retractor can be provided that can couple to a single implanted pedicle screw or other anchor and provide medial-lateral tissue retraction by moving opposed tissue manipulating implements toward or away from one another. Further, a retractor can be capable of toeing opposed tissue manipulating implements in a medial-lateral direction, e.g., pivoting or moving the tissue manipulating implements such that distal ends thereof move toward to away from one another while a distance between proximal ends thereof remains unchanged. By manipulating tissue in such a manner, the retractor can be used to widen an incision formed in patient's skin and underlying tissue to provide a working channel to a surgical site, such as a patient's intervertebral disc space. Such a retractor can advantageously be indexed to a patient via coupling with the implanted anchor and can provide medial-lateral or other tissue retraction while minimizing instrumentation size and complexity. While the systems, devices, and methods described herein can be utilized in a variety of surgical procedures, they can have particular utility in various orthopedic or neurologic surgical procedures, such as spinal operations.

In one aspect, a surgical instrument is provided that can include a body configured to couple to an implantable anchor, a first tissue manipulating implement coupled to the body and capable of polyaxial movement relative thereto, and a second tissue manipulating implement coupled to the body and capable of polyaxial movement relative thereto. Moreover, the first and second tissue manipulating implements can be opposed to one another such that they can move any of toward and away from one another.

The devices and methods described herein can have a number of additional features and/or variations, all of which are within the scope of the present disclosure. In some embodiments, for example, the instrument can further include an anchor extension extending between the body and the implantable anchor. In some embodiments, the instrument can further include a lock coupled to the body and configured to interface with the anchor extension to selectively lock a position of the body relative to the anchor extension. In certain embodiments, the lock can include a pawl configured to move relative to the body and interface with a ratchet formed on the anchor extension.

In some embodiments, each of the first and second tissue manipulating implements can couple to the body via a ball and socket joint. Still further, in some embodiments each of the ball and socket joints can include an expanding member configured to selectively lock the ball and socket joint against movement.

The tissue manipulating implements can have a variety of forms. In some embodiments, at least one of the tissue manipulating implements can be a planar blade. In certain embodiments, the tissue manipulating implements can include a first blade and a second blade configured to translate relative to one another to adjust an overall length of the tissue manipulating implement. Moreover, in some embodiments at least one of the tissue manipulating implements can include a distal tip configured to scrape tissue from bone. In other embodiments, at least one of the tissue manipulating implements can include a pointed distal tip.

In some embodiments, the instrument can further include an extension post coupled to the body. The extension post can, in some embodiments, pivot relative to the body. The extension post can be utilized to, for example, couple the instrument to an external structure in some embodiments.

A variety of movements of the tissue manipulating implements are possible. For example, and as noted above, the implements can be configured to move any of toward and away from one another, for example in medial and lateral directions relative to a patient's body. In certain embodiments, polyaxial movement of the tissue manipulating implements relative to the body can also include toeing of a distal end of the tissue manipulating implements any of toward and away from one another. For example, a distal end of the tissue manipulating implements can move any of toward and away from one another while a distance between a proximal end of the tissue manipulating implements remains unchanged.

In another aspect, a surgical instrument is provided that can include first and second opposed handles pivotably coupled to one another and configured to couple to an implantable anchor, as well as a first tissue manipulating implement coupled to the first handle and a second tissue manipulating implement coupled to the second handle. Moreover, movement of the first and second handles any of toward and away from one another can cause movement of the first and second tissue manipulating implements any of toward and away from one another.

As with the system described above, a number of variations and additional features are possible. For example, in some embodiments the instrument can further include an anchor extension extending between the opposed handles and the implantable anchor. In certain embodiments, the instrument can further include a lock coupled to the opposed handles and configured to interface with the anchor extension to selectively lock a position of the opposed handles along a length of the anchor extension. Further, in some embodiments the first and second tissue manipulating implements can be configured to move polyaxially relative to the anchor extension.

In some embodiments, the instrument can further include a lock configured to selectively prevent movement of the opposed handles relative to one another. Such a lock can also serve to prevent movement of the tissue manipulating implements relative to one another.

The tissue manipulating implements can have a variety of configurations. For example, in some embodiments at least one of the tissue manipulating implements can be a planar blade. In certain embodiments, the tissue manipulating implements can include a first blade and a second blade configured to translate relative to one another to adjust an overall length of the tissue manipulating implement. In other embodiments, at least one of the tissue manipulating implements can include a distal tip configured to scrape tissue from bone. Still further, in some embodiments at least one of the tissue manipulating implements can include a pointed distal tip.

In some embodiments, the instrument can further include an extension post coupled to the opposed handles. The extension post can be configured to adjust relative to the opposed handles in certain embodiments. The extension post can be utilized in certain embodiments to couple the instrument to an external structure, such as a surgical table, etc.

A variety of movements of the tissue manipulating implements are possible. In some embodiments, for example, the first and second tissue manipulating implements can be configured for toeing movement relative to one another. In such movement, distal ends of the tissue manipulating implements can move any of toward and away from one another by a greater amount than proximal ends of the tissue manipulating implements.

In another aspect, a surgical method is provided that can include implanting an anchor in a patient's bone and coupling an anchor extension to the anchor. The method can further include coupling a retractor assembly to the anchor extension such that first and second tissue manipulating implements of the retractor assembly extend into an incision formed in the patient's tissue. Further, the method can include moving the first and second implements of the retractor assembly away from one another in a medial-lateral direction to increase a size of the incision formed in the patient's tissue.

In some embodiments, at least one of the first and second tissue manipulating implements can be a planar blade. In certain embodiments, the method can further include scraping tissue from bone using a distal end of at least one of the tissue manipulating implements. For example, a distal end of a planar blade can be utilized for this purpose.

In some embodiments, the method can further include toeing the first and second tissue manipulating implements relative to one another such that distal ends of the tissue manipulating implements move any of toward and away from one another by a greater amount than proximal ends of the tissue manipulating implements.

In some embodiments, the method can further include adjusting a length of at least one of the tissue manipulating implements. Moreover, in certain embodiments the method can include locking a position of the retractor assembly along a length of the anchor extension. The method can also include locking a position of the anchor extension relative to the anchor in some embodiments. Still further, in some embodiments the method can include locking a position of at least one of the tissue manipulating implements relative to the anchor extension.

Any of the features or variations described above can be applied to any particular aspect or embodiment of the present disclosure in a number of different combinations.

The absence of explicit recitation of any particular combination is due solely to the avoidance of repetition in this summary.

BRIEF DESCRIPTION OF THE DRAWINGS

FIG. 20A is a front perspective view of one embodiment of a surgical instrument assembly according to the teachings provided herein;

FIG. 20B is a top perspective view of the assembly of FIG. 20A;

FIG. 22A is an alternative detail view of the assembly of FIG. 21;

FIG. 22B is another alternative detail view of the assembly of FIG. 21;

FIG. 23A is a detail view of one embodiment of a tissue manipulating implement and a driver;

FIG. 23B is a detail view of the tissue manipulating implement and driver of FIG. 23A;

FIG. 24 is a front perspective view of the tissue manipulating implement of FIG. 23A coupling to the assembly of FIG. 21;

FIG. 25 is a front perspective view of polyaxial movement of the tissue manipulating implement of FIG. 23A when coupled to the assembly of FIG. 21;

FIG. 26 is a front perspective view of adjusting a length of the tissue manipulating implement of FIG. 23A;

FIG. 27 is a front perspective view of the driver locking the tissue manipulating implement of FIG. 23A;

FIG. 28 is a front perspective view of coupling a second tissue manipulating implement to the assembly of FIG. 21;

FIG. 29 is a front perspective view of a driver selectively inducing polyaxial movement of the second tissue manipulating implement of FIG. 28 and selectively locking against such movement;

FIG. 34A is a top view of one embodiment of ranges of motion of tissue manipulating implements and opposed handles of the instrument of FIG. 30;

FIG. 34B is a side perspective view of the instrument of FIG. 34A;

FIG. 35 is a top view of one embodiment of a lock to selectively maintain a position of opposed handles relative to one another;

FIG. 52 is a detail view illustrating a first step in coupling a tissue manipulating implement to another component of a surgical instrument assembly;

FIG. 53 is a detail view illustrating a second step in coupling a tissue manipulating implement to another component of a surgical instrument assembly;

FIG. 54 is a detail view illustrating degrees of freedom of a tissue manipulating implement relative to a surgical instrument assembly;

FIG. 66 is a front perspective view of one embodiment of a tissue manipulating implement coupled to a polyaxial screw receiver head;

FIG. 67 is a rear perspective view of the tissue manipulating implement and receiver head of FIG. 66;

FIG. 91A is a side view of another embodiment of an actuating instrument prior to coupling with a tissue manipulating implement;

FIG. 91B is a side view of the actuating instrument of FIG. 91A coupled to the tissue manipulating implement of FIG. 91A;

FIG. 91C is a side view of the actuating instrument of FIG. 91A being decoupled from the tissue manipulating implements of FIG. 91A;

FIG. 91D is a side view of the actuating instrument of FIG. 91A decoupled from the tissue manipulating implement of FIG. 91A;

FIG. 98 is a side view of the light source of the assembly of FIG. 93 and various tissue manipulating implements of the assembly of FIG. 93;

FIG. 99C is a perspective view of the various tissue manipulating implements of FIG. 98;

FIG. 100A is a perspective view of one embodiment of a modular tissue manipulating implement aligned with an arm of the assembly of FIG. 93;

FIG. 100B is a perspective view of the modular tissue manipulating implement of FIG. 100A coupled to the arm of FIG. 100A;

FIG. 101A is a top perspective view of one embodiment of a tissue manipulating implement adjuster aligned with an expandable tissue manipulating implement of the assembly of FIG. 93;

FIG. 101B is a side view of the tissue manipulating implement adjuster and expandable tissue manipulating implement of FIG. 101A aligned with a static tissue manipulating implement of the assembly of FIG. 93;

FIG. 101C is a side view of the tissue manipulating implement adjuster and expandable tissue manipulating implement of FIG. 101A coupled with the static tissue manipulating implement of FIG. 101B;

FIG. 101D is a detail view of the tissue manipulating implement adjuster, expandable tissue manipulating implement, and static tissue manipulating implement of FIG. 101C; and FIG. 101E is a detail view of the expandable and static tissue manipulating implements of FIG. 101D after decoupling the tissue manipulating implement adjuster.

DETAILED DESCRIPTION

Figure 1:
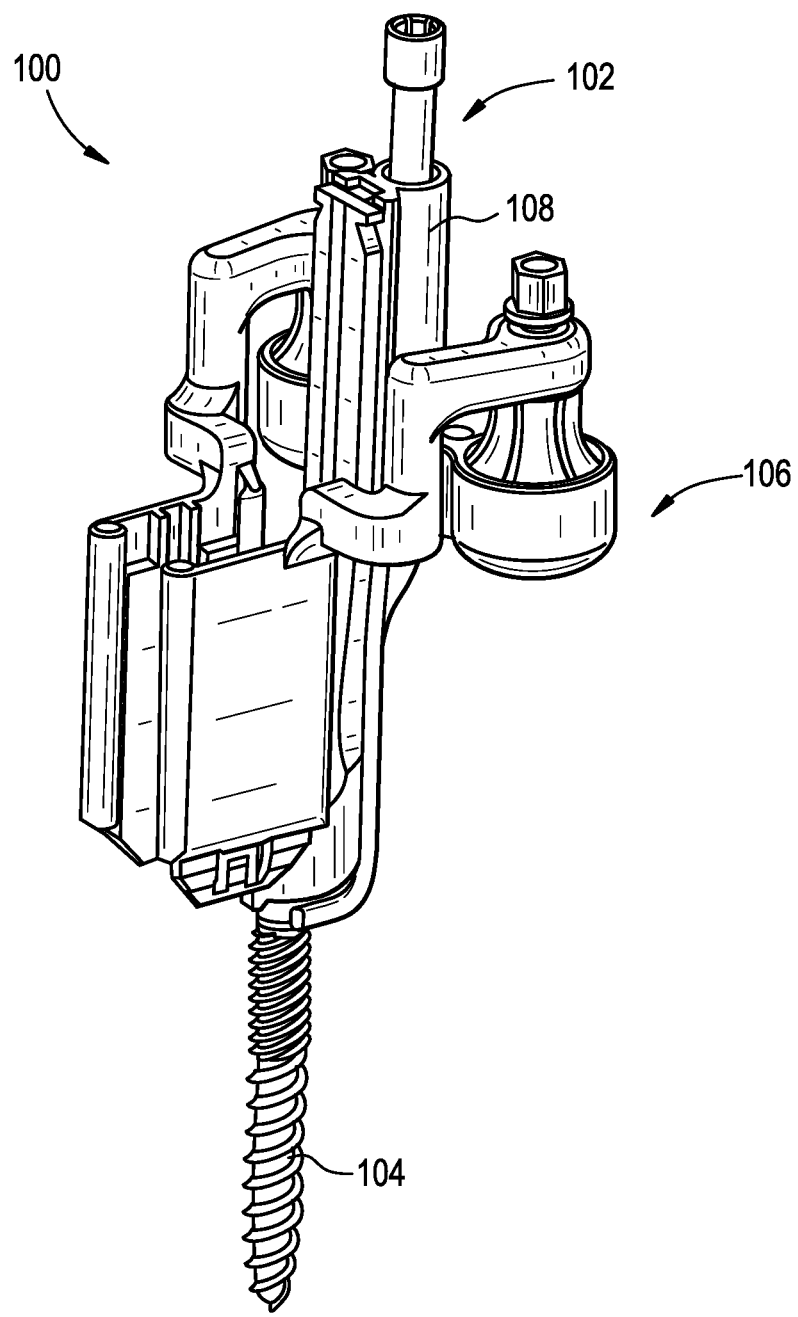
FIG. 1 is an illustration of one embodiment of a surgical instrument assembly according to the teachings provided herein.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used, and the methods and procedures in which the devices will be used.

FIGS. 1-9 illustrate an exemplary surgical instrument assembly 100 according to the teachings provided herein. The assembly 100 can be used in various surgical procedures, including spinal surgeries such as microsurgical bone resection, spinal decompression, spinal fusion, and the like. In general, the assembly 100 can include a support instrument 102 that couples to an implanted anchor 104, such as a pedicle or other bone screw. The assembly 100 can further include a retractor 106 coupled to the support instrument 102. Other components not illustrated here can be included or coupled to the assembly 100. Such components can include, for example, any of a variety of cameras or visualization systems, and any of a variety of other surgical instruments.

An exemplary method of using the assembly 100 of FIGS. 1-9 can include any one or more of the following steps, performed in any of a variety of sequences: a) making an incision in a skin of a patient; b) percutaneously inserting through the incision an implantable anchor, such as a pedicle or other bone screw; c) coupling the support instrument 102 to the implanted anchor (e.g., a pedicle anchor); d) coupling a tissue retractor to the instrument; e) providing medial-lateral retraction of tissue surrounding an incision; f) coupling an optical visualization instrument to the tissue retractor and/or instrument; g) resecting a portion of the superior articular process, and/or performing a microsurgical decompression procedure; h) extracting intervertebral disc material including removing cartilaginous material from the vertebral endplates; i) inserting an interbody device; and j) deploying a mechanism of stabilization to stabilize the intervertebral segment.

Returning to FIGS. 1-9, FIG. 1 illustrates one embodiment of a surgical instrument assembly 100 that includes a support instrument 102 coupled to an implantable anchor 104 and a tissue retractor 106. Further details regarding embodiments of the support instrument 102 can be found in U.S. application Ser. No. 16/139,409, entitled "PATIENT-MOUNTED SURGICAL SUPPORT," filed on Sep. 24, 2018, and issued as U.S. Pat. No. 10,945,773. Further details regarding embodiments of the implantable anchor 104 can be found in U.S. application Ser. No. 15/208,872, filed on Jul. 13, 2016, entitled "BONE ANCHOR ASSEMBLIES AND RELATED INSTRUMENTATION," and issued as U.S. Pat. No. 10,463,402. Furthermore, details regarding certain embodiments of retractors that can be used in the surgical assembly 100 can be found below and in U.S. Pat. No. 7,491,168. The entire contents of each of these references are incorporated by reference herein.

Figure 3:
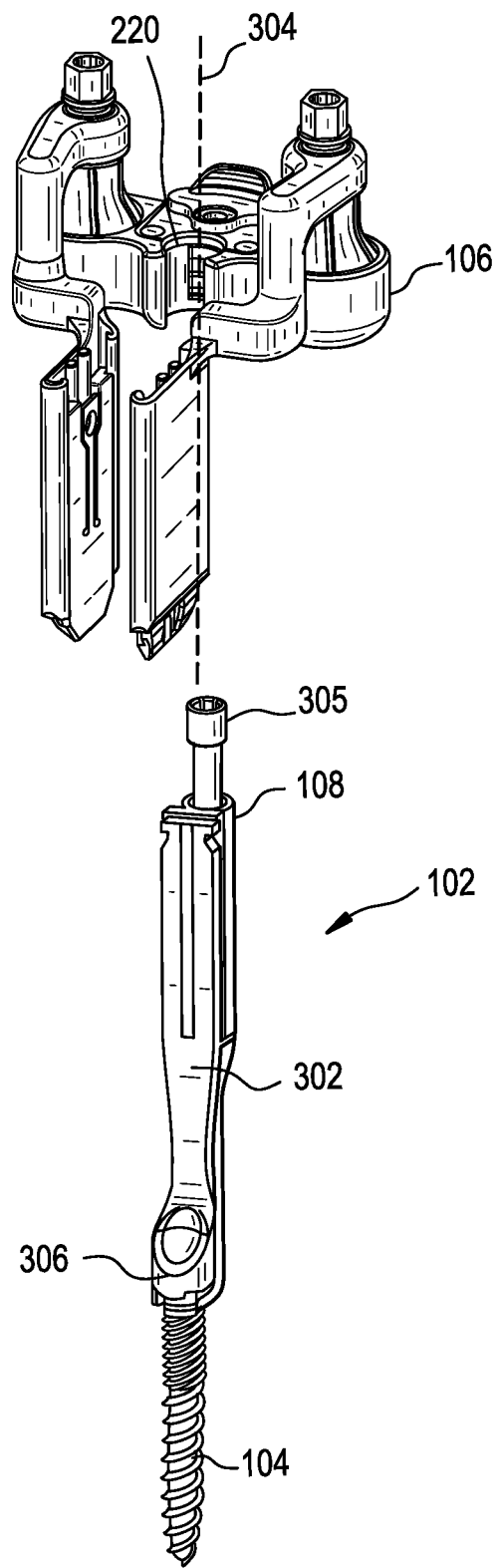
FIG. 3 is an exploded view of the assembly of FIG. 1.
Figure 4:
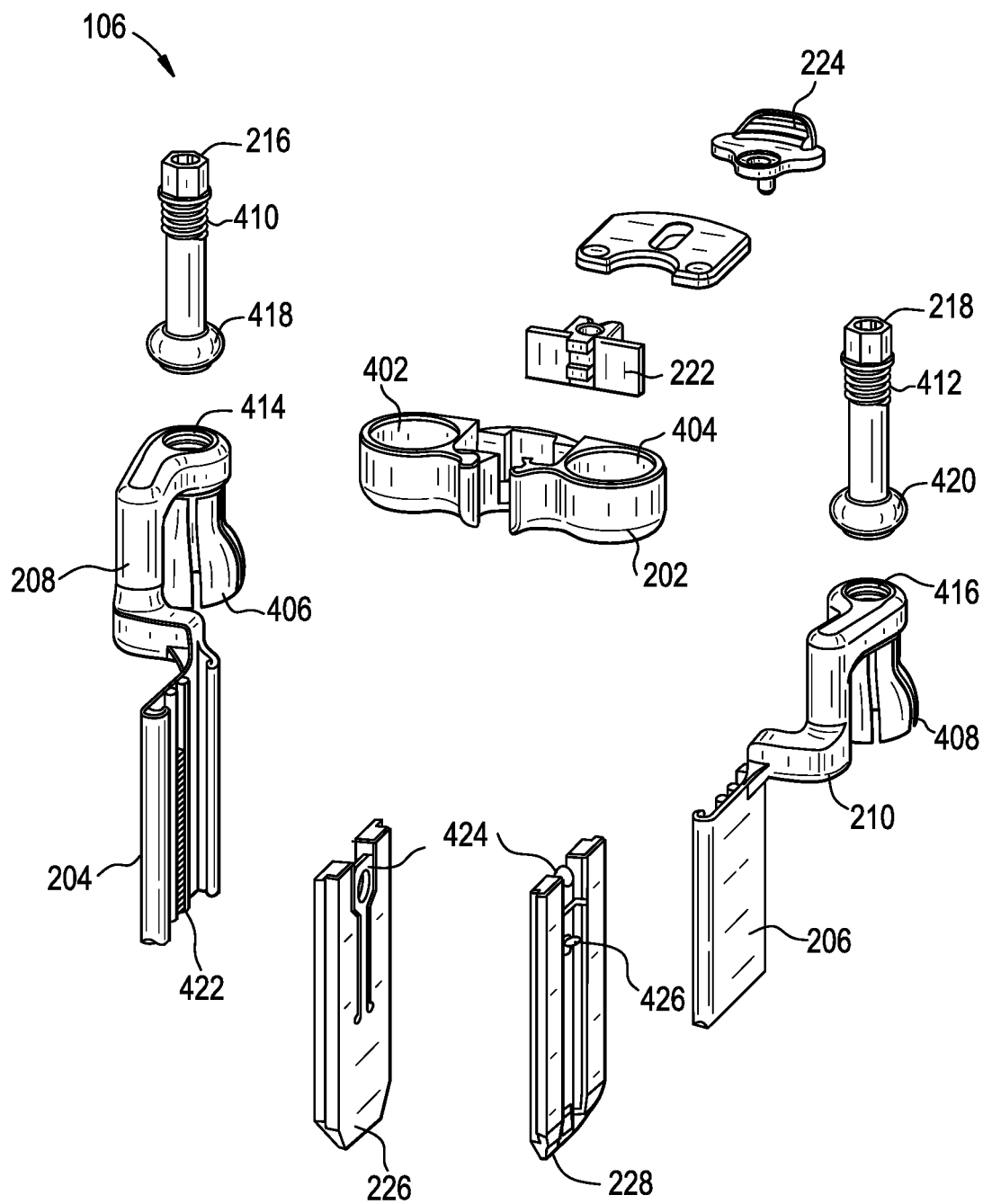
FIG. 4 is an exploded view of the retractor of FIG. 2.

Generally, the support instrument can include an elongate body 108 with a laterally-extending fork formed at a distal end thereof that can interface with a narrowed neck of the anchor 104. The fork can include opposed projections that extend laterally from a distal portion of the elongate body and define a U-shaped or otherwise open-ended recess that can be sized to receive a portion of the implantable anchor 104. For example, the projections can be configured to fit around a proximal portion of a bone anchor that can be part of a modular mono- or poly-axial pedicle screw. Such anchors can include a generally cylindrical distal shank portion with threads for tapping into bone, as well as a narrowed neck proximal of the shank portion and a wider proximal head. The proximal head can be generally spherical or semi-spherical in shape and can be configured to couple with a receiver head before or after implantation in a patient's bone. The elongate body can also include a lock configured to exert a drag force on the head of the anchor to control polyaxial movement of the instrument 102 relative to the anchor 104. As shown in FIG. 3, the lock can include a lock body 302 that is coupled to the elongate body 108 and translatable relative thereto along a longitudinal axis 304 of the elongate body. The lock body 302 can have a generally elongate shape to facilitate coupling with and translating or sliding along or relative to the elongate body 108. The lock can be actuated by a lock screw 305 that can cause distal translation of the lock body 302 as the screw is threaded further into the elongate body 108. The lock body 302 can further include a laterally-extending ring-shaped projection 306 at a distal end thereof that can be configured to contact the proximal head of the anchor 104 and exert a drag force thereon. The ring-shaped projection 306 can define a lumen to maintain access to a drive feature formed on a proximal end of the head of the anchor 104. This lumen, in combination with the lateral extension of the projection 306 and the fork formed at the distal end of the elongate body 108 can orient the instrument 100 such that a longitudinal axis of the instrument is laterally offset or non-coaxial with a longitudinal axis of the anchor 104. Such a configuration can allow a driver or other instrument to access the drive feature of the anchor 104 even when the instrument 100 is coupled thereto. This can enable flexibility to implant the anchor 104 any of before and after coupling the instrument 100 thereto.

Returning to FIG. 2, a more detailed illustration of one embodiment of the tissue retractor 106 is provided. The retractor 106 can include a body 202 that can be configured to couple to the support instrument or anchor extension 102. First and second tissue manipulating implements 204, 206 can be coupled to the body 202 by, for example, rigid arms 208, 210, respectively. Each of the first and second tissue manipulating implements 204, 206 can be capable of polyaxial movement relative to the body via a polyaxial joint 212, 214, such as a ball-and-socket joint. Such a joint can allow the tissue manipulating implements 204, 206 to move relative to one another in a variety of manners. For example, the implements 204, 206 can be pivoted toward or away from one another about an axis extending parallel to a longitudinal axis of a support instrument 102, (e.g., an axis parallel to the axis 304 in FIG. 3). The implements 204, 206 can also be pivoted toward or away from one another about an axis transverse or oblique to, e.g., the axis 304. For example, the implements 204, 206 can be toed relative to one another, wherein distal ends of the implements are moved toward or away from one another by an amount greater than proximal ends of the implements. In some embodiments, toeing can include moving distal ends of the implements away from one another while proximal ends of the implements are either moved toward one another or do not move such that a distance between the proximal ends of the implements remains unchanged. Furthermore, each polyaxial joint 212, 214 can include a lock 216, 218 that can be used to selectively lock a position of the associated tissue manipulating implement 204, 206 or impose a drag force to inhibit movement in the absence of at least a threshold level of force.

Figure 2:
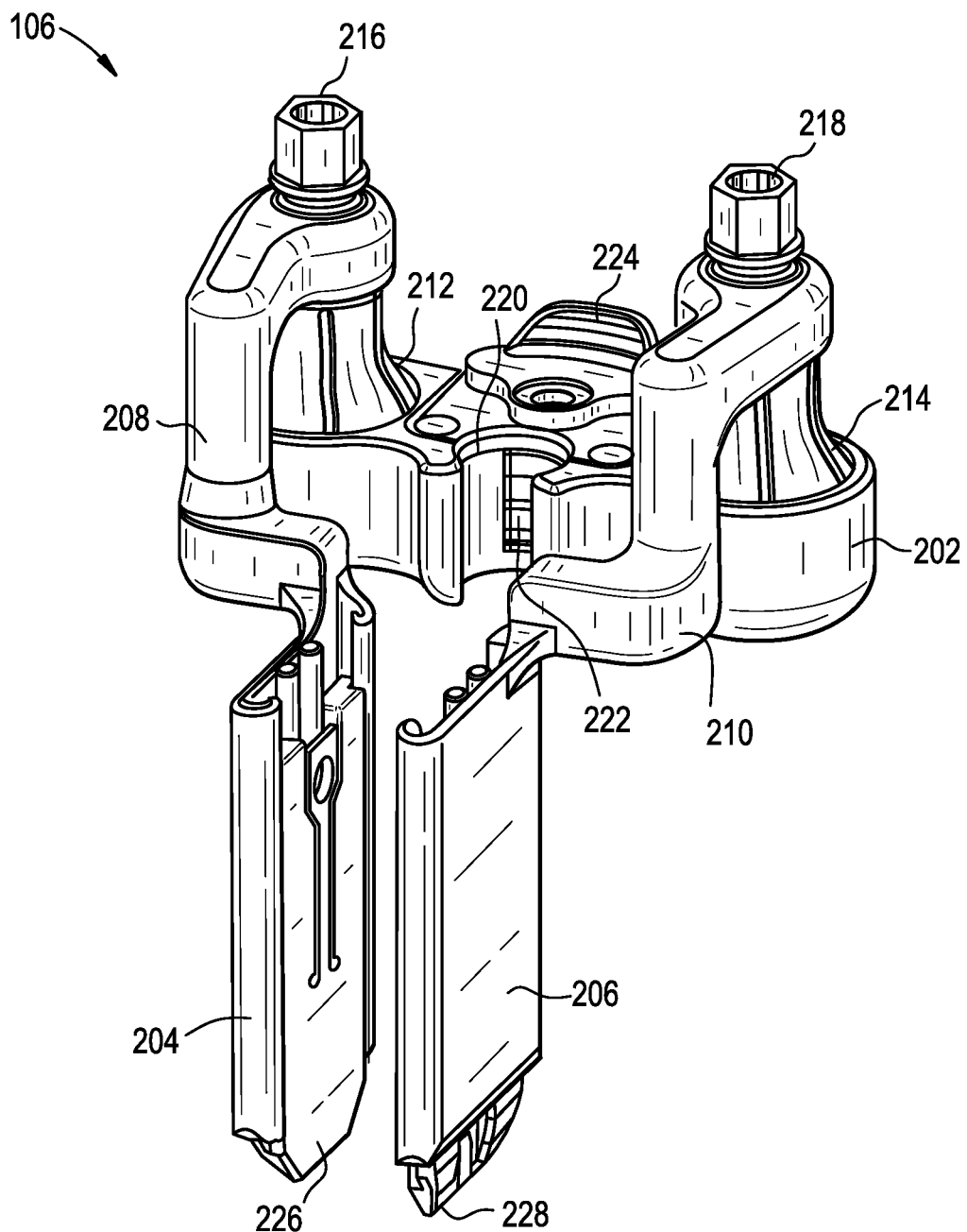
FIG. 2 is a detail view of a retractor of the assembly of FIG. 1.

As noted above, the tissue retractor 106 can be configured to couple to a support instrument or anchor extension 102 and can be configured to slide along a length of such an instrument to adjust a height of the retractor relative to the implanted anchor 104. As shown in FIG. 2, the body 202 of the retractor can include a closed or partially-open lumen or recess 220 configured to receive a portion of the support instrument 102, such as a generally cylindrical elongate body 108 (see FIG. 1). The retractor 106 can further include a feature to selectively lock a position of the retractor relative to the support instrument 102, such as a spring-biased protrusion or pawl 222 that can engage a ratchet rack or other series of recesses or other surface features formed on the elongate body 108 of the support instrument. Furthermore, in some embodiments the locking feature 222 can be configured to prevent not only movement along a length of the support instrument 102, but also rotation thereabout. An actuator 224, such as the illustrated sliding or translating member, can be included to allow a user to easily withdraw the protrusion 222 against the biasing force of a spring or other biasing element disposed within the body 202 of the retractor 106.

In addition to adjusting a position of the retractor 106 along a length of the support instrument 102, a length of each of the tissue manipulating implements 204, 206 can also be adjusted. For example, in some embodiments the tissue manipulating implements 204, 206 can each include an extension 226, 228 that can be configured to translate relative to the tissue manipulating implements 204, 206. Proximally or distally translating either extension 226, 228 relative to the associated implement 204, 206 can change an overall length of the implement and, for example, can allow an implement to reach deeper into tissue even if the retractor 106 is mounted at a greater height above a patient's skin surface along a more proximal portion of the support instrument elongate body 108.

FIG. 3 illustrates a partially exploded view showing how the retractor 106 can be coupled to the support instrument 102 by sliding the retractor down or distally over a proximal portion of the support instrument. For example, the recess or lumen 220 of the retractor 106 can be aligned with the generally cylindrical elongate body 108 of the support instrument and the retractor can be advanced down or distally along the axis 304. While advancing the retractor relative to the support instrument, a user can manually retract the spring biased pawl or protrusion 222 using the sliding lever 224 to allow free movement of the retractor relative to the support instrument. When a desired position is reached, the user can release the lever 224 such that the protrusion 222 is advanced into engagement with a complementary recess or other feature formed on the elongate body 108 to maintain the relative positioning of the retractor and support instrument. In other embodiments, the complementary features formed on the elongate body 108 and the protrusion 222 can be formed as a biased ratchet wherein, e.g., distal advancement of the retractor can be achieved without actuating the lever 224, but proximal withdrawal of the retractor 106 relative to the instrument 102 requires actuating the lever 224 to withdraw the biased protrusion 222.

FIGS. 4-7 illustrate the retractor 106 in various exploded and partially transparent views to better explain the interaction of various components thereof. For example, the polyaxial joints 212, 214 can be seen in greater detail. Each polyaxial joint 212, 214 can include a socket 402, 404 formed in the body 202 of the retractor 106. Each of the arms 208, 210 coupled to the tissue manipulating implements 204, 206 can have a generally ball-shaped proximal end 406, 408 that includes one or more relief slots formed therein such that various portions of the proximal end can deform relative to other portions thereof. A lock 216, 218 can be coupled to each arm 208, 210 by cooperation between threads 410, 412 formed on the lock and threads 414, 416 formed on an inner surface of through-holes in the arms 208, 210. Further, a deformable expanding member 418, 420 can be formed at a distal end of each lock 216, 218.

Figure 5:
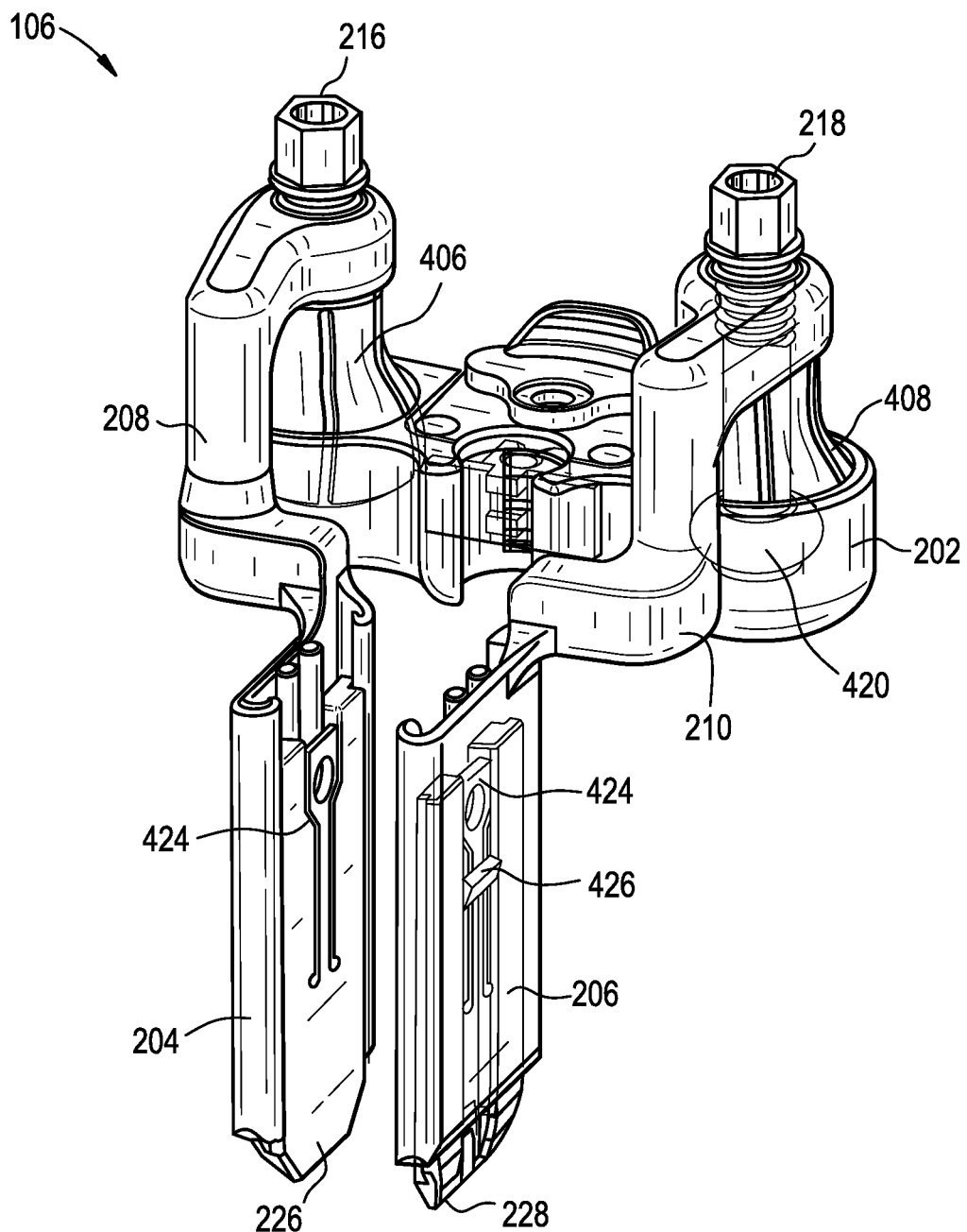
FIG. 5 is a partially-transparent detail view of the retractor of FIG. 2.
Figure 6:
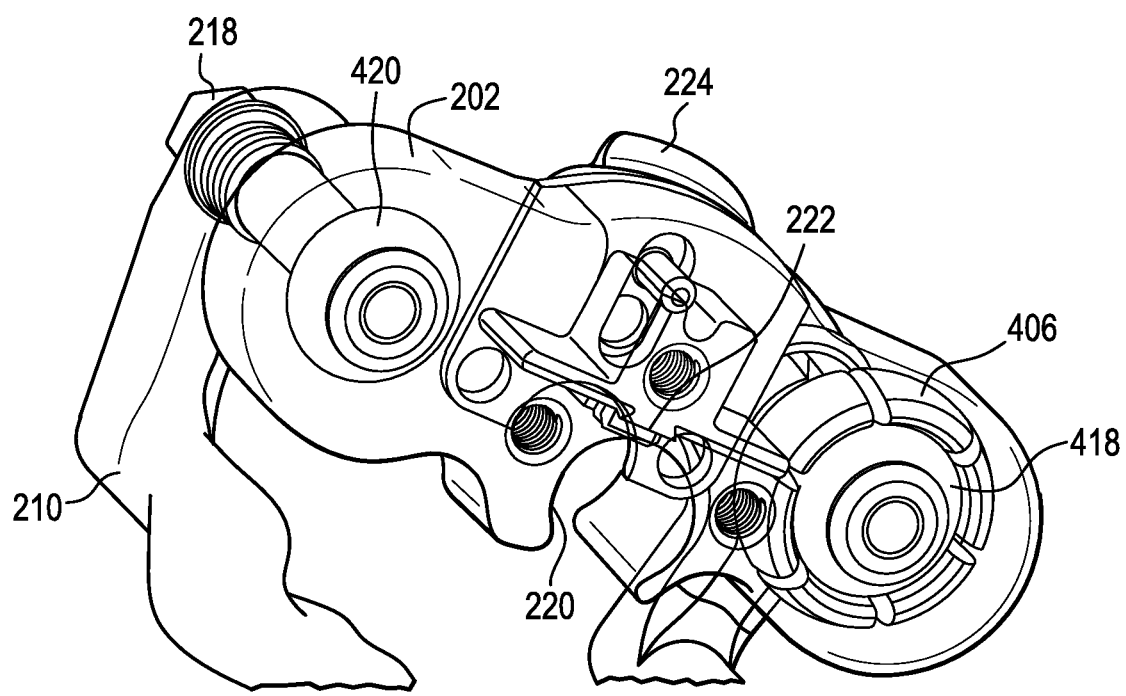
FIG. 6 is a bottom partially-transparent detail view of the retractor of FIG. 2.
Figure 7:
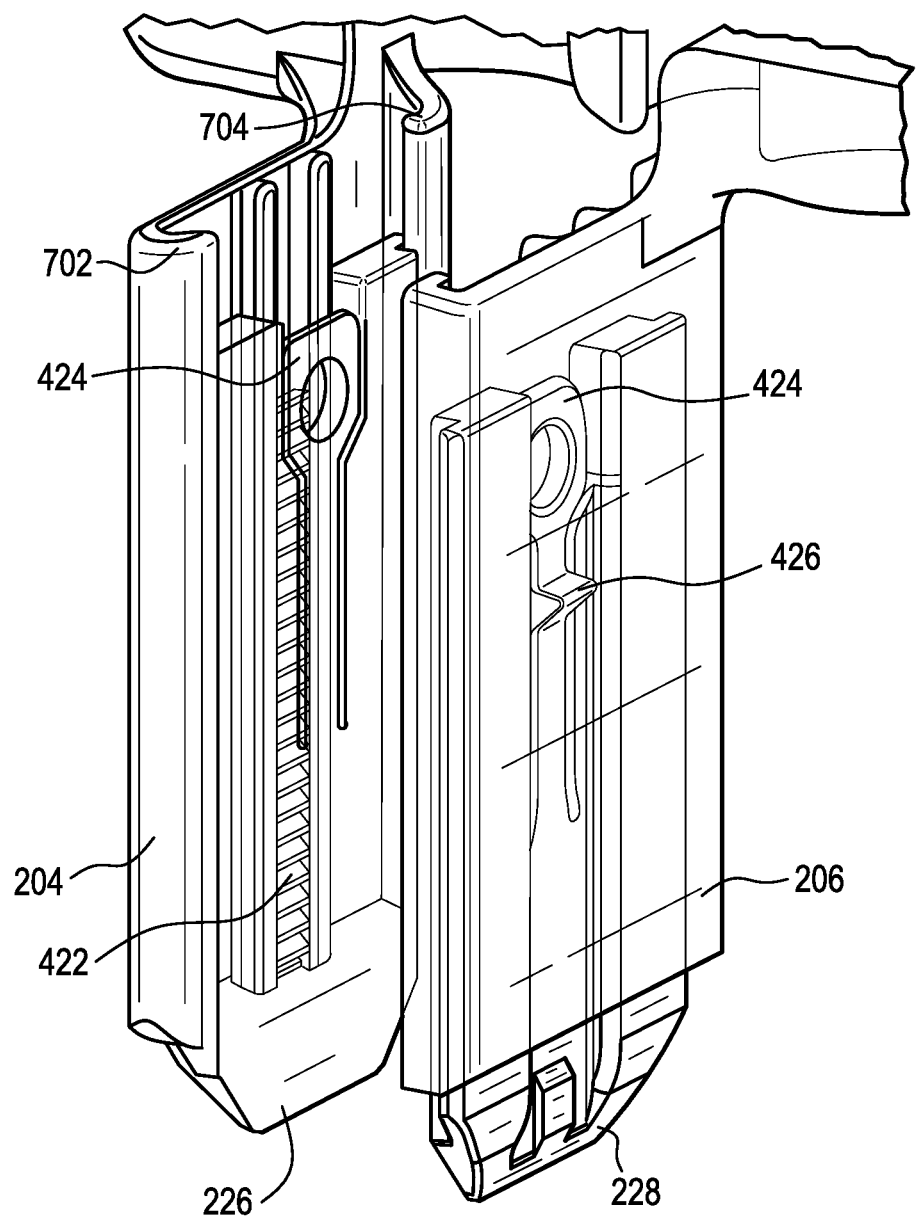
FIG. 7 is a detail view of tissue manipulating implements of the retractor of FIG. 2.

When assembled, as shown in FIGS. 5 and 6, the expanding members 418, 420 can be disposed within the generally ball-shaped proximal ends 406, 408. Further, both of these components can be disposed within one of the sockets 402, 404 of the body 202. In use, as the locks 216, 218 are rotated relative to the arms 208, 210, they can advance farther into the sockets 402, 404 due to the threaded coupling between the arms 208, 210 and the locks 216, 218. Advancement of the locks 216, 218 into the sockets 402, 404 can cause the deformable expanding member 418, 420 formed at a distal end of each lock to compress and expand radially outward. As the deformable expanding members 418, 420 expands radially, they can urge the various portions of the ball-shaped proximal ends 406, 408 of the arms 208, 210 into contact with the sidewalls of the sockets 402, 404. This can cause an increase in frictional force between the sockets 402, 404 and the ball-shaped proximal ends 406, 408 of the arms 208, 210. Further, upon sufficient advancement of the locks 216, 218, the force of the expanding members 418, 420 can effectively lock the ball-shaped proximal ends 406, 408 in a given position and thereby prevent any movement of the arms 208, 210 or tissue manipulating implements 204, 206 coupled thereto.

FIGS. 4-7 also show additional features of the tissue manipulating implements 204, 206, as well as the extensions 226, 228 coupled thereto. For example, the tissue manipulating implements 204, 206 can each be generally planar blades or surfaces configured to abut against and hold back tissue in order to effectively perform tissue retraction. In other embodiments, however, a variety of other shapes can be utilized, including non-planar blades or surfaces having curvature along any axis. The illustrated implements 204, 206 also include arms 702, 704 formed along a length thereof that define a recess that can receive an edge of an extension 226, 228 to prevent separation of the extension 226, 228 and the implement 204, 206. The extensions 226, 228 can translate relative to the implements 204, 206 and a relative position of the extension and the implement can be maintained by interaction between a ratchet rack 422 formed on each implement 204, 206 and a leaf spring 424 with a pawl 426 formed on each extension 226, 228. The pawl 426 and/or teeth or other surface features formed on the ratchet rack 422 can be biased to allow, for example, advancement of the extensions 226, 228 relative to the implements 204, 206 in one direction while preventing retracting in an opposite direction without urging the pawl 426 against the biasing force of the leaf spring 424.

Figure 8A:
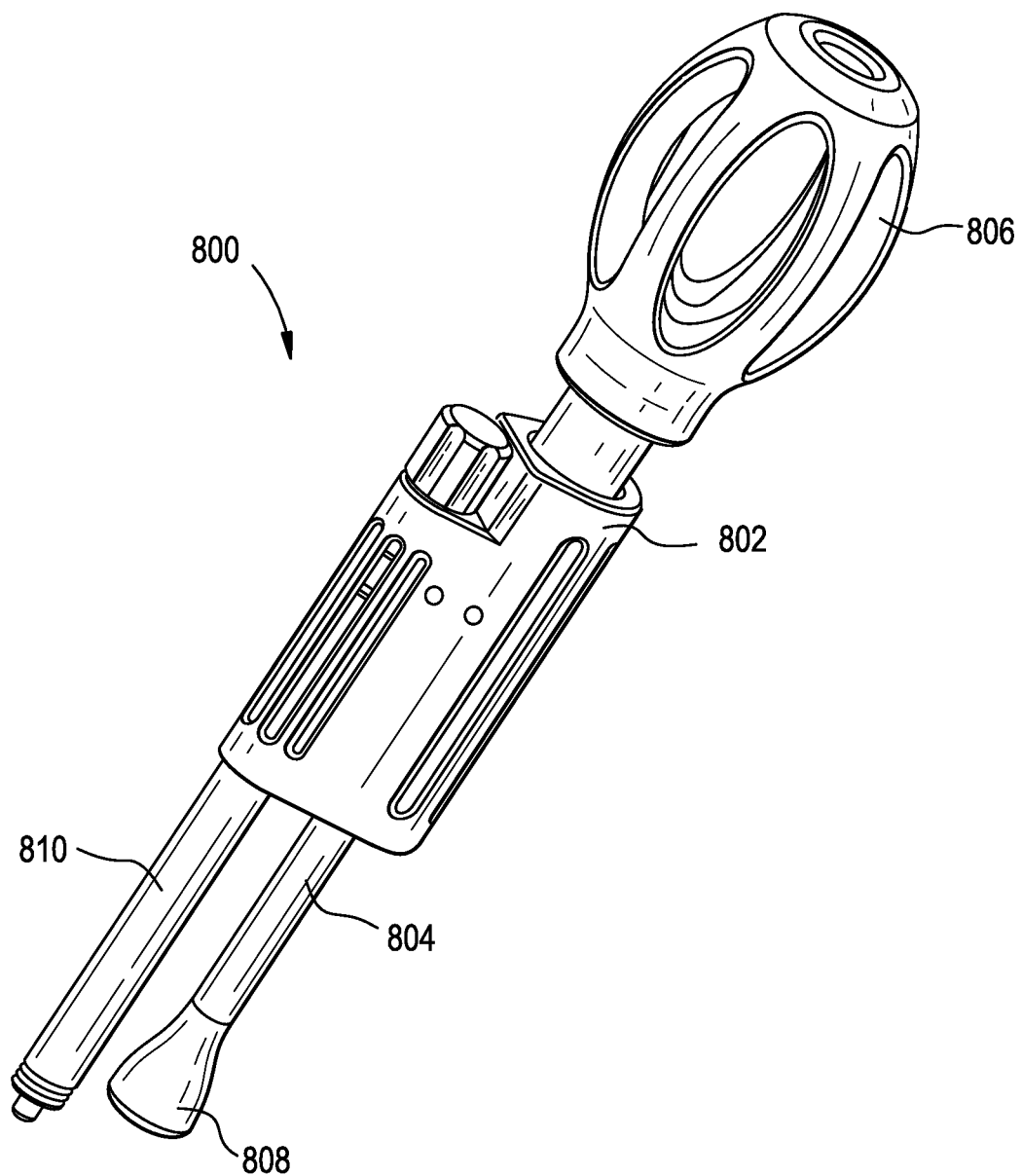
FIG. 8A is a perspective view of one embodiment of an actuating instrument according to the teachings provided herein.
Figure 8B:
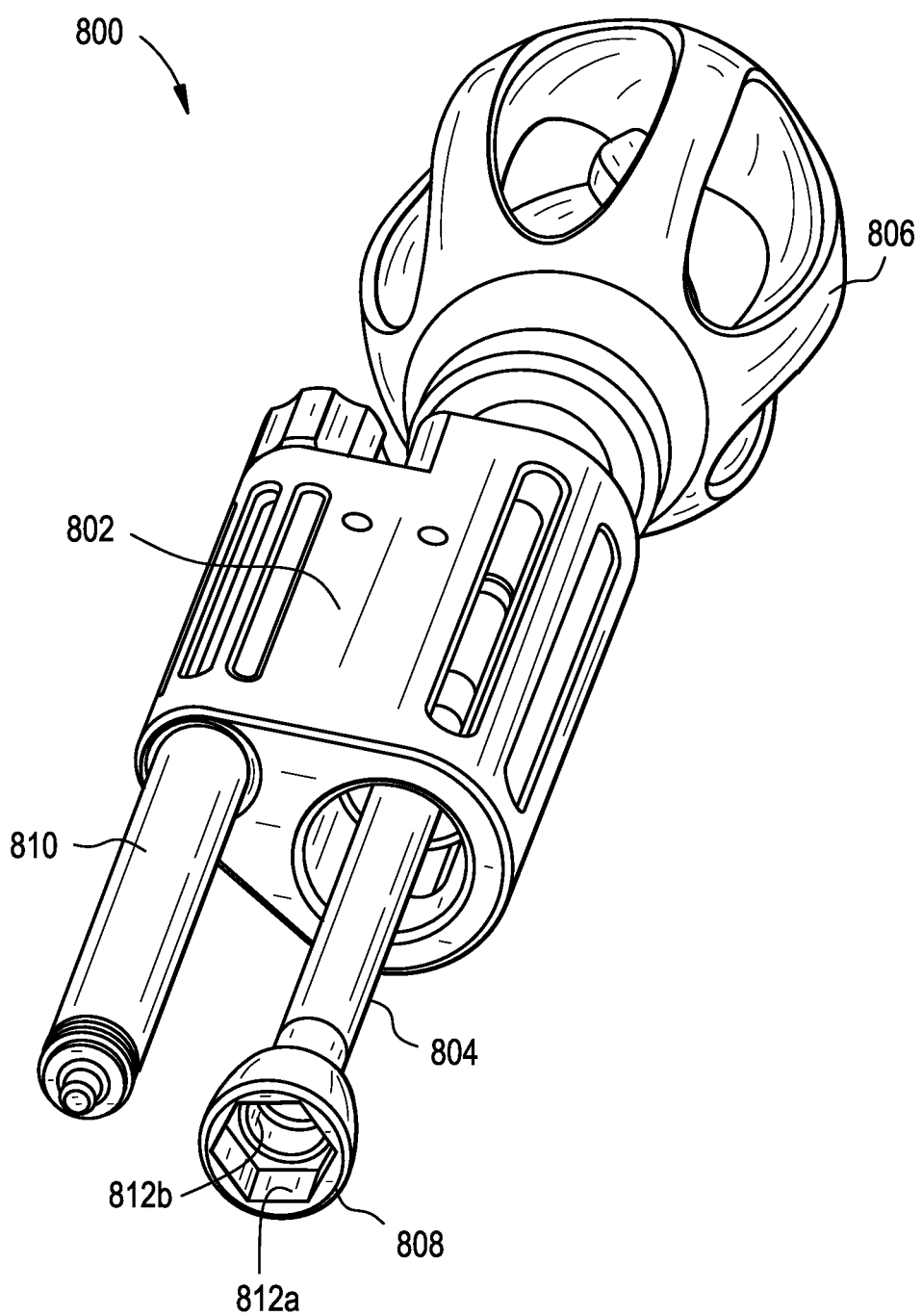
FIG. 8B is an alternative view of the actuating instrument of FIG. 8A.
Figure 9:
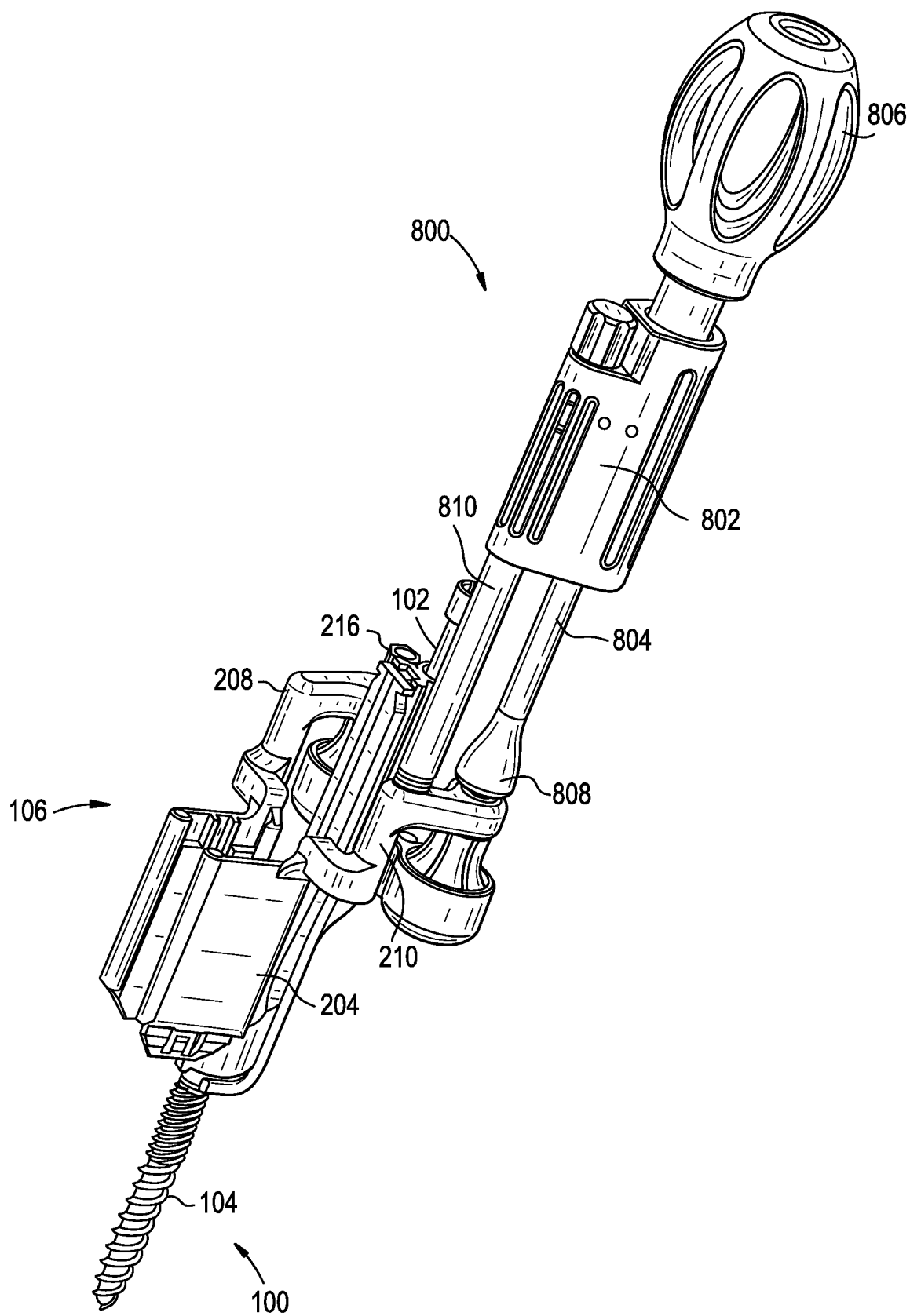
FIG. 9 is a front perspective view of the actuating instrument of FIG. 8A coupled to the surgical assembly of FIG. 1.
Figure 10:
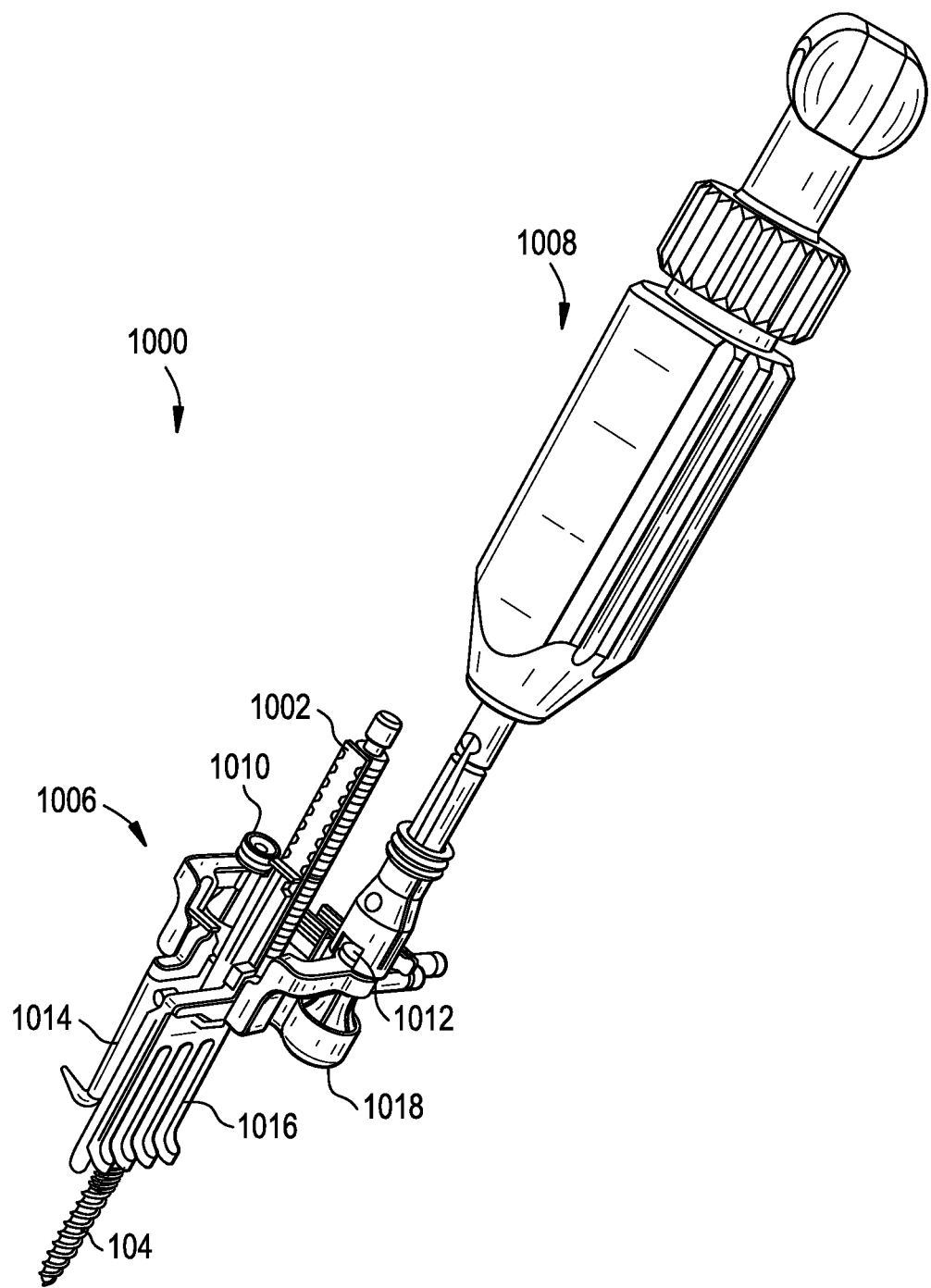
FIG. 10 is a front perspective view of another embodiment of a surgical instrument assembly according to the teachings provided herein.

FIGS. 8A-9 illustrate one embodiment of a driver 800 that can be used to actuate the locks 216, 218 of the retractor 106. As shown in FIGS. 8A and 8B, the driver 800 can include a housing 802 surrounding a driveshaft 804. The driveshaft 804 can be coupled to a handle 806 at a proximal end thereof and a drive interface 808 at a distal end thereof. The housing can also surround a second stabilizing shaft 810 that can aid in preventing torque applied to the driveshaft 804 from rotating or otherwise moving the retractor 106 and/or support instrument 102 about the implanted anchor 104, as described below. The drive interface 808 can be configured to abut against a proximal end of one of the locks 216, 218, as shown in FIG. 9. Accordingly, the drive interface can include features to aid in transferring torque to the lock, such as a socket including one or more pairs of opposed planar surfaces 812a, 812b that can abut against one or more pairs of opposed planar surfaces formed on a proximal end of the locks 216, 218.

In use, as shown in FIG. 9, the driver 800 can be positioned such that the drive interface 808 receives a proximal end of one of the locks 216, 218. The stabilizing shaft 810 can be advanced distally to abut against the corresponding arm 208, 210 and apply a distally-directed force thereto. In certain embodiments, the arm 208, 210 can include a recess formed therein that can receive a distal end of the stabilizing shaft 810, as described in connection with FIG. 23A-29 below. Torque can then be applied by a user via the handle 806 to actuate the lock 218 and the stabilizing shaft 810 can prevent the torque from rotating the entire retractor assembly 106.

The above described retractor assembly 106, in combination with the support instrument or anchor extension 102 and implanted anchor 104, can be used to, for example, widen an incision formed in a patient's skin and tissue to enable better access to a surgical site. By way of further example, in some embodiments these components can form an assembly that is anchored to a single implanted screw or anchor and provides medial-lateral tissue retraction to increase access for a variety of surgical procedures. Medially and laterally retracting skin and underlying tissue surrounding an incision can provide a wider opening and working channel between the tissue manipulating implements to access the patient's spine or intervertebral space. In some embodiments, the working channel can extend to encompass an adjacent anchor implanted in an adjacent vertebra. Once the tissue of the incision walls is retracted to form the working channel, any of a variety of surgical procedures can be performed by introducing one or more instruments through the working channel defined by the tissue manipulating implements of the retractor assembly. For example, procedures on the intervertebral disc space, such as disc replacement, discectomy, endplate preparation, fusion cage insertion, bone graft delivery, and the like can be performed by passing instruments or implants through the working channel.

FIGS. 10-19 illustrate an alternative embodiment of a surgical instrument assembly 1000 that includes a support instrument 1002 coupled to an implantable anchor 104 and a tissue retraction assembly 1006. Also shown is an alternative embodiment of a driver 1008 that can be used to actuate locks 1010, 1012 that can selectively permit or prevent polyaxial movement of opposed tissue manipulating implements 1014, 1016 relative to a body 1018 of the retraction assembly 1006.

Figure 11:
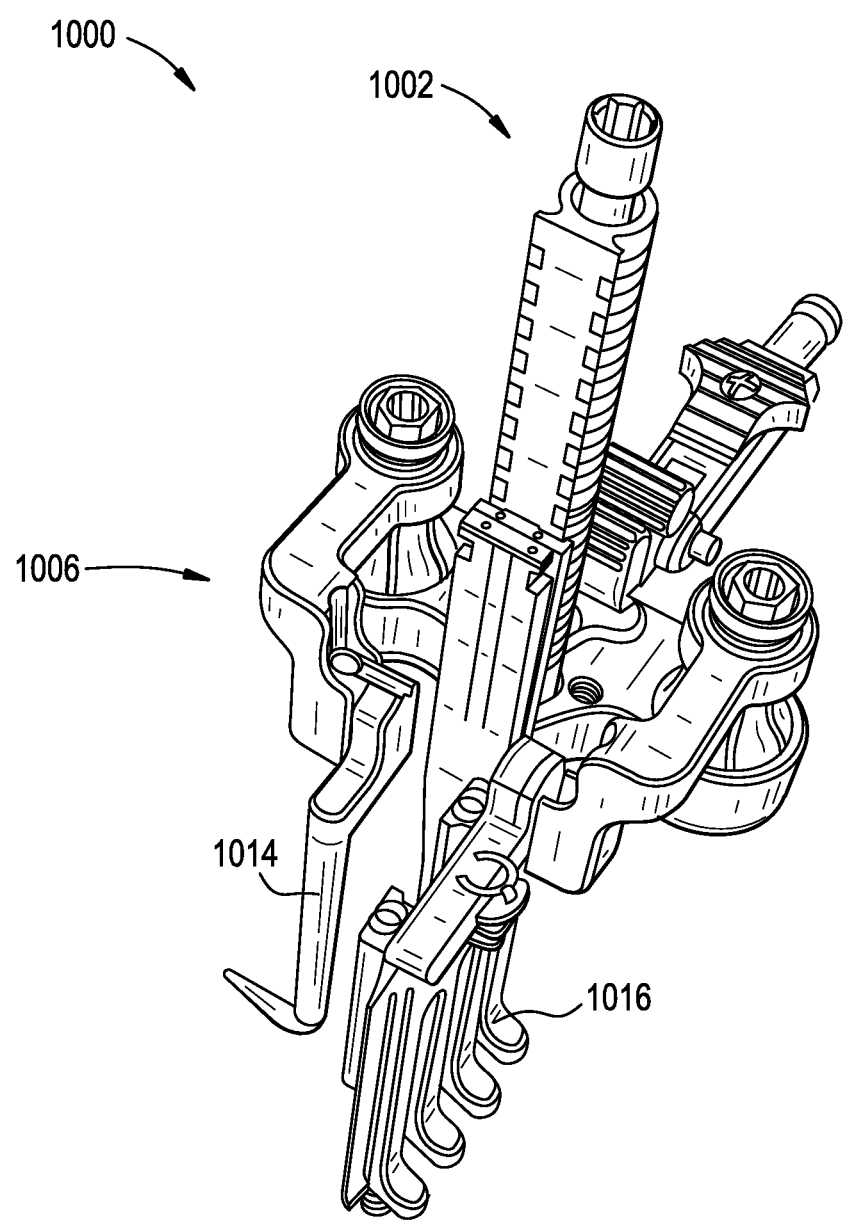
FIG. 11 is a detail view of a retractor of the assembly of FIG. 10.

As shown in FIGS. 11-14, the surgical instrument assembly 1000 is similar to the assembly 100 described above, including the basic configuration of the support instrument 1002 and the retractor assembly 1006. The support instrument 1002 has an extended length, as shown in FIG. 11, to allow for a greater range of adjustment of the retractor assembly 1006 along the support instrument 1002. Of course, any of a variety of lengths can be utilized for the support instrument 1002. Moreover, the tissue manipulating implements 1014, 1016 have a different configuration. For example, the implement 1014 is not a planar tissue retracting blade, but instead has a pointed tip that can be useful in contacting bone.

Figure 12:
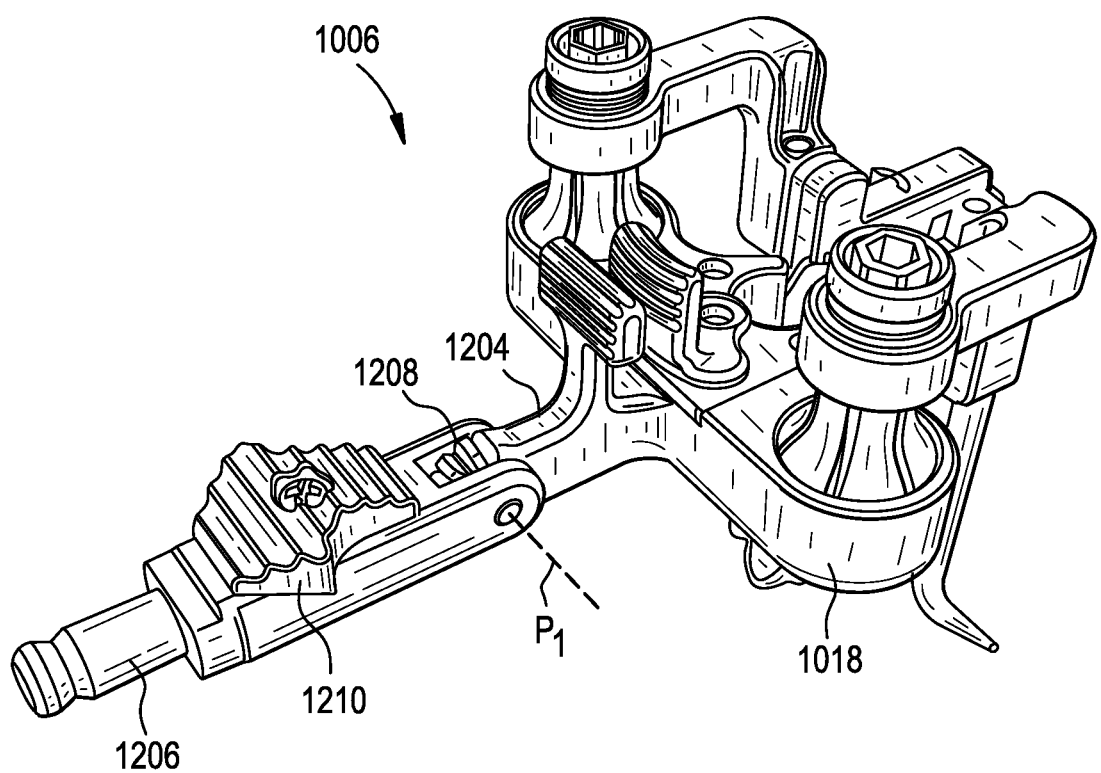
FIG. 12 is an alternative detail view of the retractor of FIG. 11.
Figure 13:
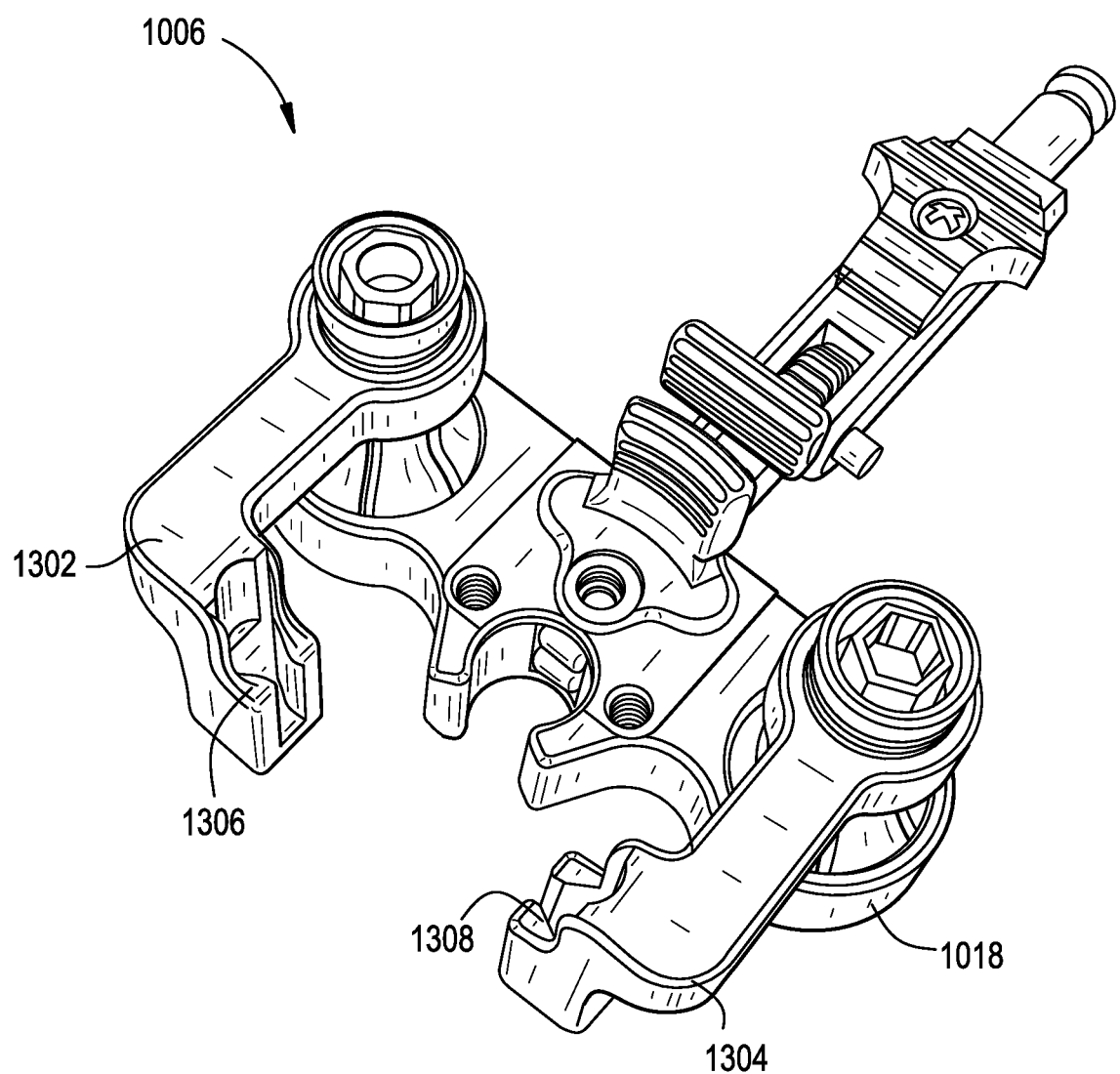
FIG. 13 is another detail view of the retractor of FIG. 11.

Further, and as shown in FIG. 12, the tissue retractor assembly 1006 can include a protrusion 1204 extending from the body 1018 that can pivotably couple to an extension post 1206. The extension post 1206 can pivot relative to the protrusion 1204 and the body 1018 about the axis Pi such that the extension post 1206 can be positioned at a variety of angles relative to the body 1018. The extension post 1206 can be used to couple the tissue retractor assembly 1006 to an external structure, such as a surgical table, etc. In some embodiments, it can be advantageous to utilize an assembly that is anchored to a patient's body—and particularly to a single implanted bone screw or other anchor—as opposed to an external structure, such as a surgical table, etc. For example, anchoring relative to a patient's body can provide an advantage by maintaining a relative position between an access device and a patient even if a patient moves during a procedure. Moreover, it can be advantageous to anchor to a single bone screw or other anchor (e.g., as opposed to constructs that span across multiple implanted anchors), as this can reduce the footprint of instrumentation and can allow greater working space for other implements employed in a procedure. In some embodiments, however, it can be possible to also anchor the instruments and assemblies described herein to an external structure, such as a surgical table, etc. The extension post 1206 can be utilized in some such embodiments. In some embodiments where external fixation is employed, locking a support instrument or anchor extension against movement relative to an implanted anchor can be avoided such that some adjustment relative to an implanted anchor is possible in case of patient movement, etc.

Figure 14:
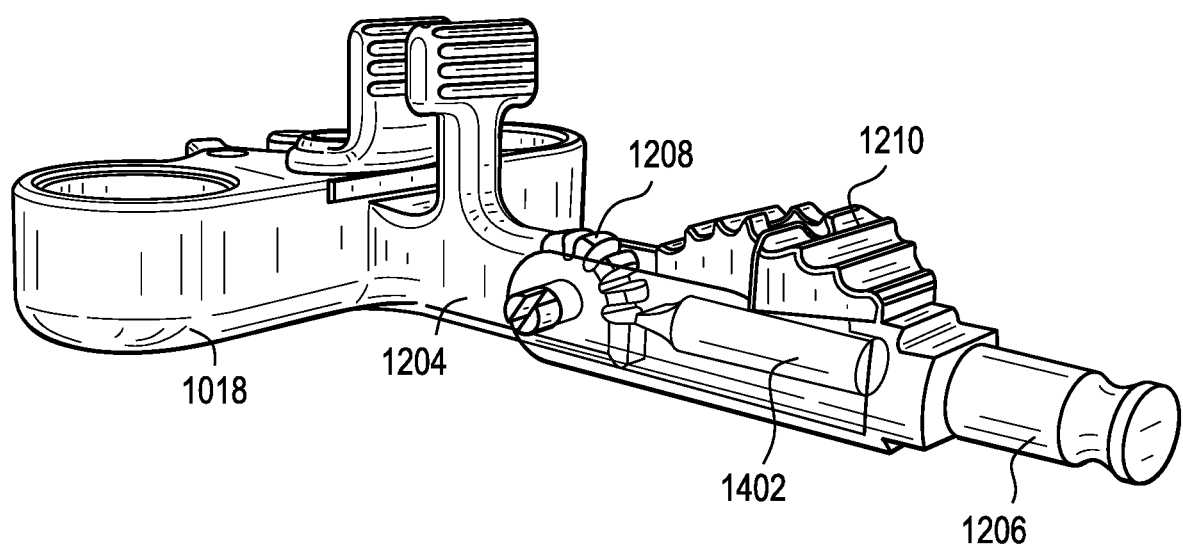
FIG. 14 is still another detail view of the retractor of FIG. 11.

As shown in FIGS. 12 and 14, the extension post 1206 can be locked at any of a variety of angles relative to the body 1018 using a pawl 1402 that can selectively engage with any of a series of recesses 1208 or other complementary surface features formed on an end of the protrusion 1204. A thumb slide 1210 can be coupled to the pawl 1402 and used to selectively advance the pawl into engagement with one of the recesses 1208 or withdraw it from contact to allow pivoting of the extension post 1206 relative to the protrusion 1204 of the body 1018.

Figure 15:
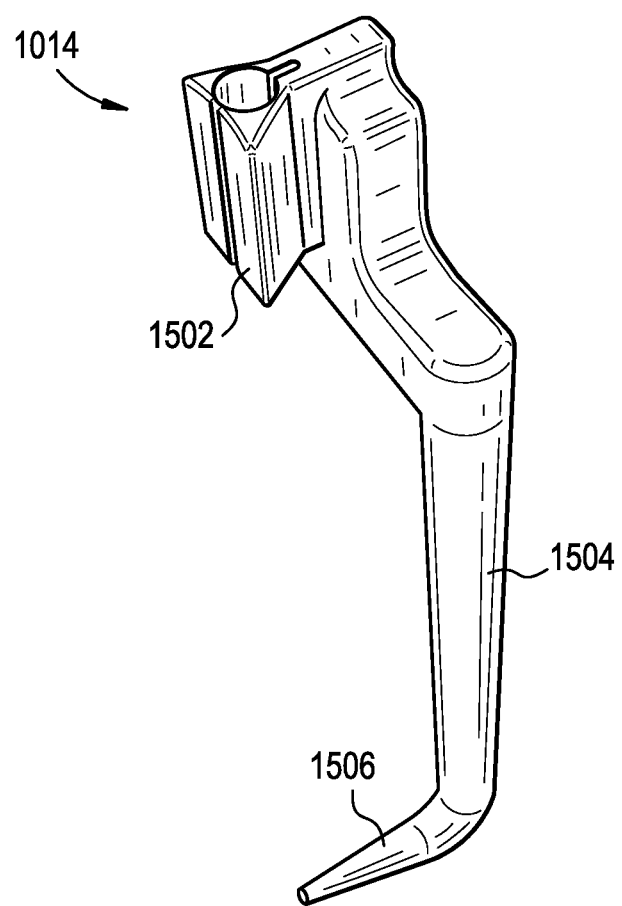
FIG. 15 is a detail view of a tissue manipulating implement of the retractor of FIG. 11.

FIGS. 13 and 15-17 illustrate various embodiments of tissue manipulating implements, as well as a modular connection mechanism for easily swapping different implements. For example, arms 1302, 1304 of the tissue retractor assembly 1006 that are polyaxially coupled to the body 1018 can include slots 1306, 1308 formed at distal ends thereof that can receive proximal portions of the tissue manipulating implements 1014, 1016. As shown in FIG. 15, for example, the tissue manipulating implement 1014 can include a proximal portion 1502 configured to be received within any one of the slots 1306, 1308 of the arms 1302, 1304. The proximal portion 1502 of the arm can include a shape that is complementary to the slots 1306, 1308, including features such as shoulders, ridges, overhangs, arms, etc. that can help prevent unintended separation of the implement 1014 from, e.g., the arm 1302. FIG. 15 also illustrates in greater detail one example of a non-planar tissue manipulating implement, including a shaft 1504 extending from the proximal portion 1502 and a laterally extending tapered distal tip 1506. Such an implement can be useful for contacting a hard surface, such as bone.

Figure 16:
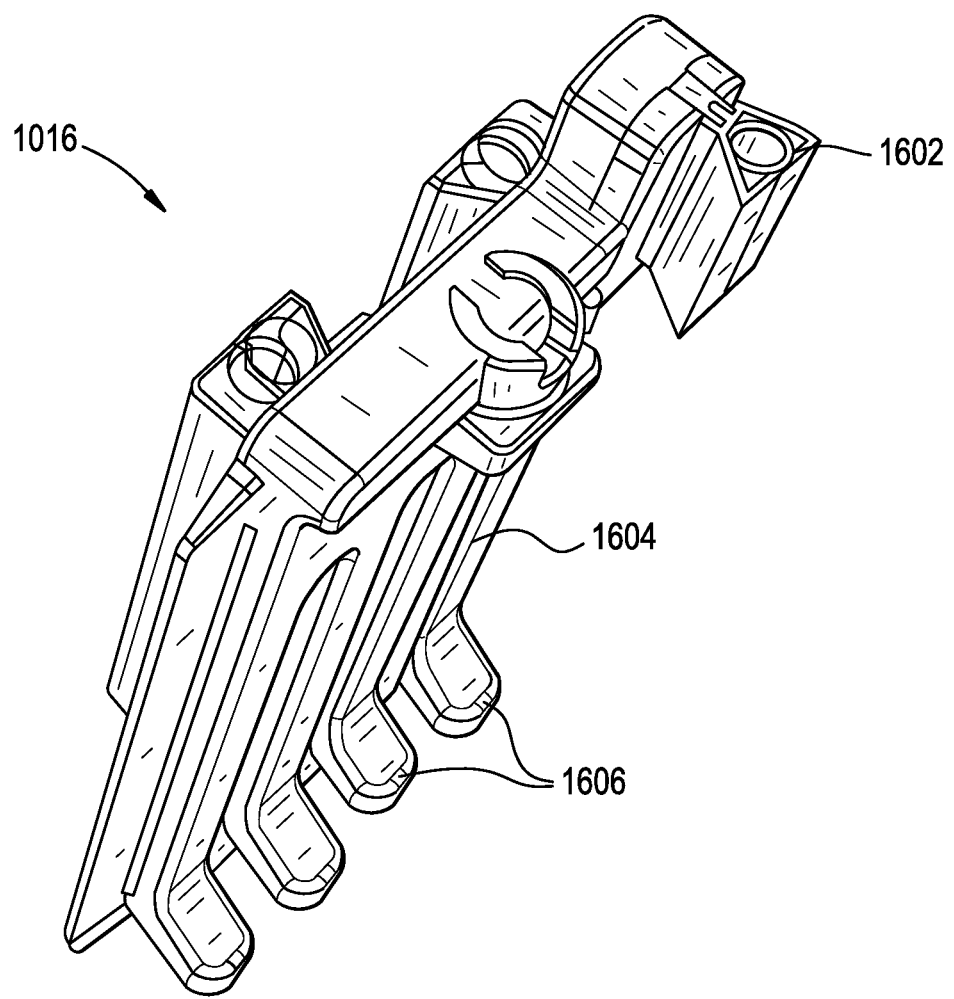
FIG. 16 is a detail view of another embodiment of a tissue manipulating implement of the retractor of FIG. 11.
Figure 17:
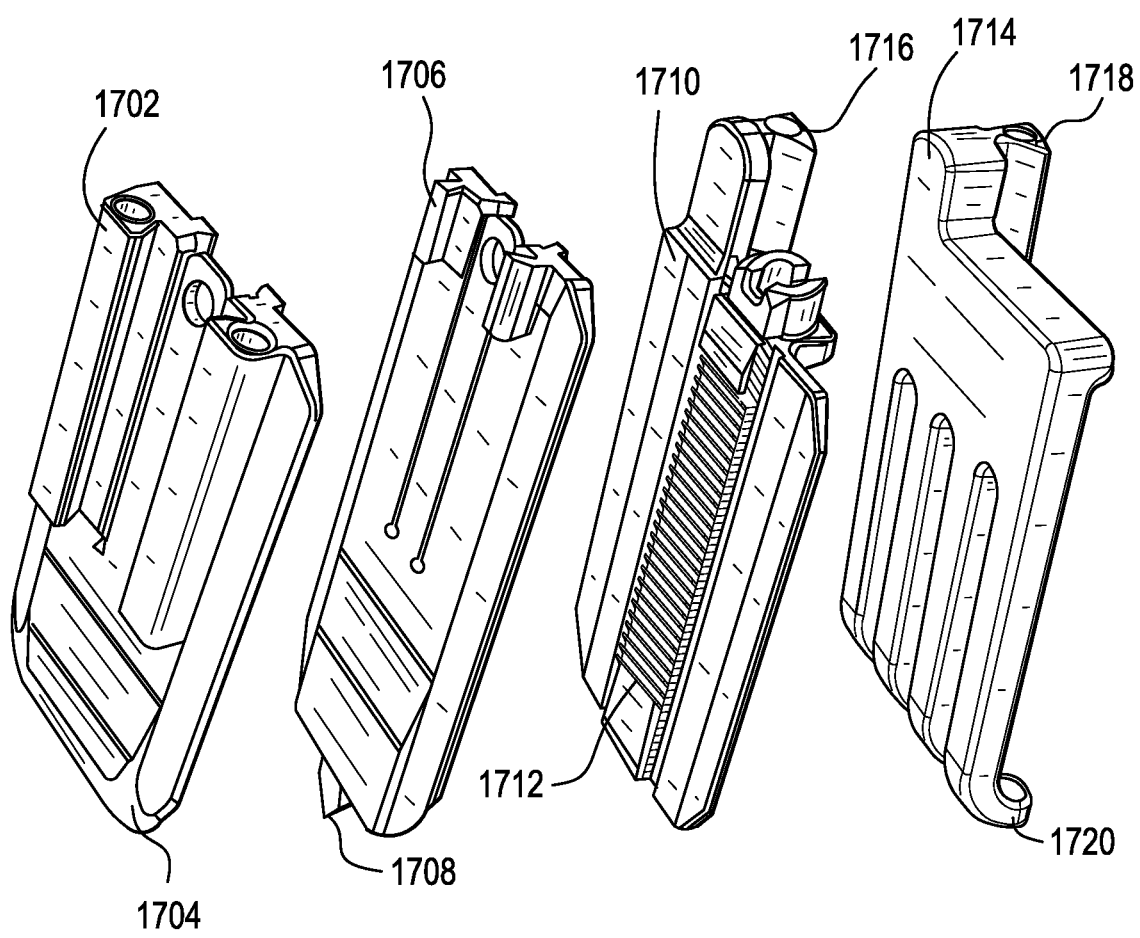
FIG. 17 is an exploded view of the tissue manipulating implement of FIG. 16.

FIGS. 16 and 17 illustrate various embodiments of planar tissue manipulating implements or blades that can be employed in various embodiments. The implement 1016 of FIG. 16, for example, can include a proximal portion 1602 configured to slide into any one of the slots 1306, 1308 of the arms 1302, 1304 of the tissue retractor assembly 1006. The implement 1016 can further include a planar body having a plurality of fingers 1604 extending along a length thereof. The fingers 1604 can include distal tips 1606 that extend away from the tissue manipulating implement 1016. Such features can be used, for example, to scrape tissue away from bone as the tissue manipulating implement 1016 is moved into position at a surgical site.

FIG. 17 illustrates a variety of alternative embodiments of generally planar tissue manipulating implements. These can include the implement 1702 having a straight distal edge 1704, as well as the implement 1706 having a pointed protrusion 1708 formed on a distal edge thereof. The implement 1710 can be configured to mate with an extension, e.g., another embodiment of a planar implement such as the implements 1702, 1706, to provide for an adjustable length tissue manipulating implement. A relative position of the implement 1710 and any extension coupled thereto can be maintained using a ratchet rack 1712 or other series of surface features and a pawl or other protrusion on the extension, as described above. The implement 1710 is also illustrated with a proximal portion 1716 for interfacing with a complementary slot formed on a modular tissue retractor assembly, as described above. Also illustrated is an alternative implement 1714, which can include a similar proximal portion 1718 for interfacing with a slot on a tissue retractor assembly arm. The implement 1714 can include a plurality of fingers 1720 extending along a length thereof, along with curved distal tips, as described above in connection with the implement 1016.

Figure 18A:
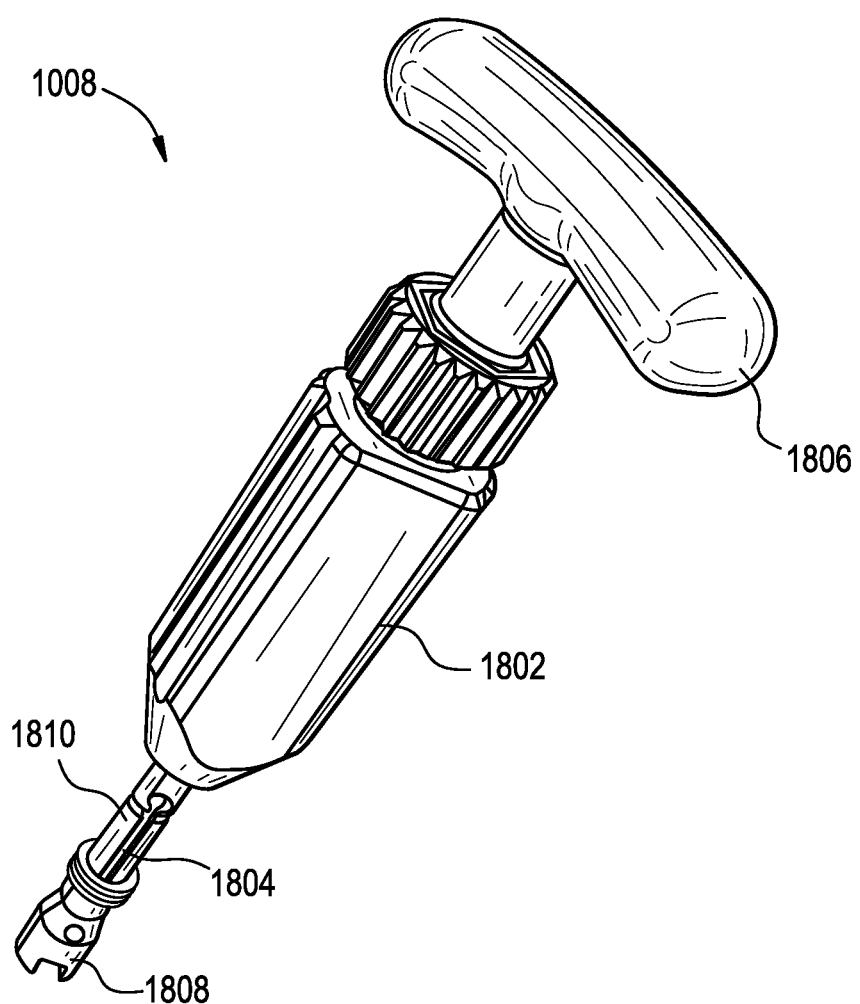
FIG. 18A is a perspective view of an actuating instrument of the assembly of FIG. 10.
Figure 18B:
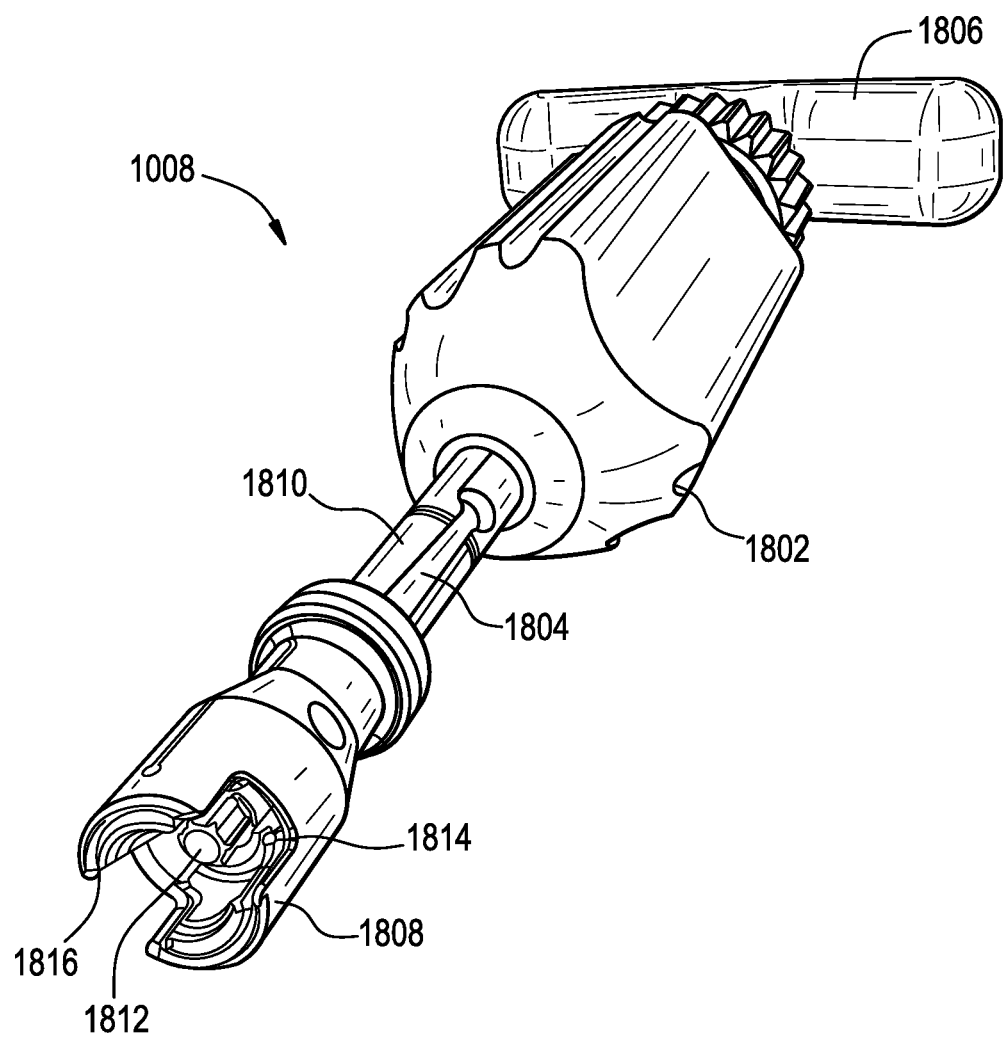
FIG. 18B is an alternative view of the actuating instrument of FIG. 18A.
Figure 19:
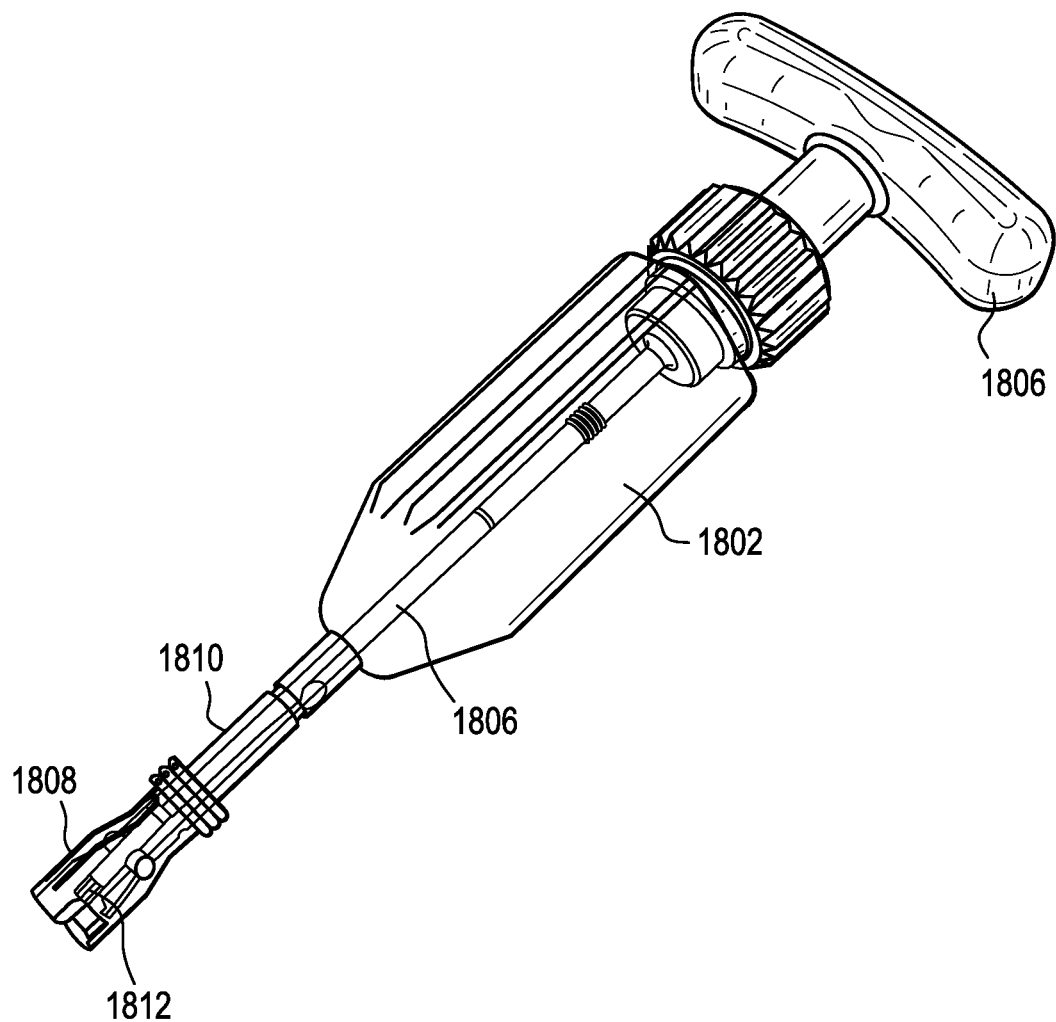
FIG. 19 is a partially-transparent perspective view of the actuating instrument of FIG. 18A.

FIGS. 18A-19 illustrate the driver 1008 in greater detail. In some embodiments, the driver 1008 can include a housing 1802 disposed about a driveshaft 1804 that couples to a handle 1806 at a proximal end thereof. A distal end 1812 of the driveshaft 1804 can be configured to interface with a proximal end of a lock 1010, 1012 of the tissue retractor assembly 1006 to impart an actuating torque thereto. The driver 1008 can also include a stabilizing shaft 1810 disposed coaxially about the driveshaft 1804 and coupled to the housing 1802 and an interface 1808. The interface 1808 can include opposed slots or cut-outs 1814, 1816 that can receive portions of one of the arms 1302, 1304 when the interface is disposed over one of the locks 1010, 1012 such that the distal end 1812 of the driveshaft 1804 engages the lock. A user can then counter brace against any tendency of the retractor assembly 1006 to rotate or otherwise move in response to turning the handle 1806 by holding the housing 1802 steady. More particularly, the rigid, non-rotational coupling between the housing 1802, the stabilizing shaft 1810, and the interface 1808, in combination with the interface 1808 being unable to rotate relative to the arms 1302, 1304 due to the slots 1814, 1816, can provide effective stabilization when a user holds the base 1802 while turning the handle 1806.

FIGS. 20A-29 illustrate still another embodiment of a surgical instrument assembly 2000 including a surgical support instrument 2002 coupled to an anchor 104 and a tissue retractor assembly 2003. The tissue retractor assembly 2003 is similar to those described above, including first and second opposed tissue manipulating implements 2006, 2008 that are polyaxially coupled to a body 2004 that slides along a length of the support instrument 2002. The tissue manipulating implements 2006, 2008 are illustrated as curved bodies with at least the implement 2006 including an extension 2010 to adjust a length thereof. Further, the extension 2010 can include a plurality of fingers 2012 extending from a distal end thereof that can be used, for example, to scrape tissue from bone as the implement 2006 and extension 2010 is positioned at a surgical site. As with embodiments described above, the polyaxial joints 2014, 2016 can be selectively lockable to introduce a drag force when moving the tissue manipulating implements 2006, 2008 or to completely prevent their movement relative to the body 2004 of the retractor assembly 2003.

Figure 21:
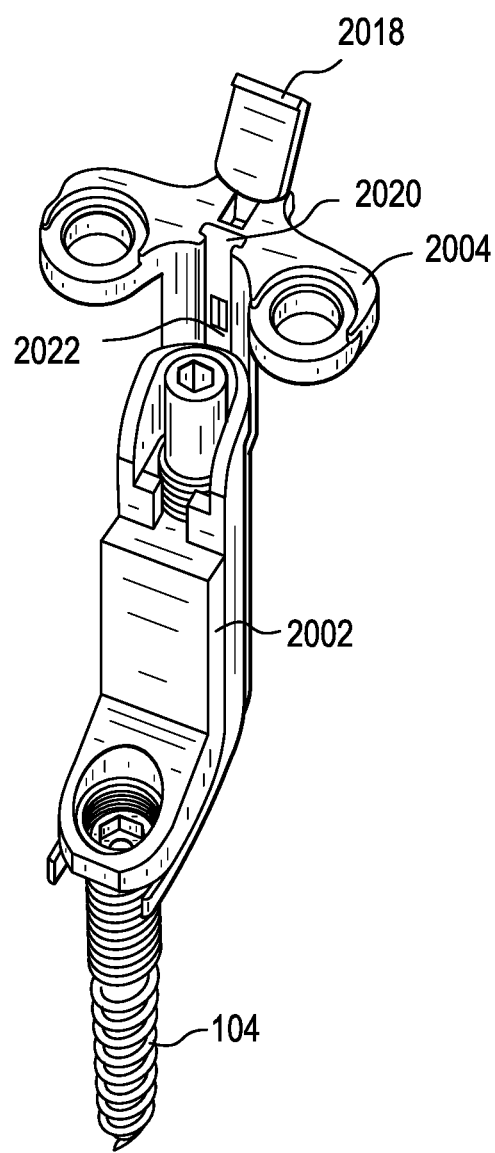
FIG. 21 is a detail view of a portion of the assembly of FIG. 20A.

As shown in the figures, the tissue retractor assembly 2003 can slidingly couple to the support instrument 2002 via a slot 2020 formed in the body 2004 that can receive a complementary-shaped ridge or protrusion 2022 formed along a length of the support instrument 2002. For example, the body 2004 of the tissue retractor assembly 2003 can be aligned over the support instrument 2002 and advanced downward or distally such that the ridge 2022 is received within the slot 2020, as shown in FIG. 21. In order to allow free sliding of the support instrument 2002 and the retractor assembly 2003, a lock lever 2018 can be moved about a pivot axis to clear a pawl 2202 from a ratchet rack 2204 formed on the support instrument 2002, as shown in FIG. 22A. When a desired position of the retractor assembly 2004 relative to the support instrument 2002 is reached (e.g., a height aligned with a skin surface of a patient or at some desired distance above the skin surface), the lock lever 2018 can be moved to engage the pawl 2202 with the ratchet rack 2204, thereby locking the two components relative to one another, as shown in FIG. 22B. Of course, in various embodiments the lock lever 2018 can be biased and/or the pawl and ratchet rack can have complementary shapes that allow for movement in one direction, e.g., downward or distally along a length of the support instrument 2002, while resisting movement in an opposite direction.

As shown in FIGS. 23A-29, tissue manipulating implements can be modularly coupled to the tissue retractor assembly 2003. For example, a driver 2300 can be coupled to a proximal end of the tissue manipulating implement 2006 as shown in FIGS. 23A and 23B. Note that a distal end of a driveshaft 2302 of the driver 2300 can interface with a lock 2306 of the tissue manipulating implement 2006, and a distal end of a stabilizing shaft 2304 can be received within a recess 2308 formed in a proximal portion of the implement 2006, such as a connecting arm that couples to the lock 2306. With the implement 2006 coupled to the driver 2300, the driver can position the implement such that a ball-shaped distal portion of the lock 2306 is received within a socket formed in the body 2004 of the tissue retractor assembly 2003, as shown in FIGS. 24 and 25. The tissue manipulating implement 2006 can be moved polyaxially relative to the body 2004, support instrument 2002, and anchor 104 using the driver 2300 or direct manipulation by the user. Such polyaxial movement is illustrated by arrows 2502 in FIG. 25. Further, a length of the tissue manipulating implement 2006 can be adjusted by translating the extension 2010 relative thereto in a proximal or distal direction, as indicated by arrows 2602 in FIG. 26.

In some embodiments, a user can employ the driver 2300 coupled to the tissue manipulating implement 2006 in place of a cobb or other surgical instrument for separating muscle or other tissue from bone. For example, a user could utilize the plurality of fingers or teeth 2012 at a distal end of the tissue manipulating implement or blade 2006 to scrape tissue from bone prior to coupling the implement to the body 2004. In still other embodiments, the implement 2006 can be utilized in a similar manner after coupling to the body 2004, but adjusting a position of retractor assembly 2003 and polyaxially moving the implement 2006 to separate tissue from bone.

When a desired position of the tissue manipulating implement 2006 is achieved, a user can rotate a handle of the driver 2300 as shown at arrow 2702 in FIG. 27 to actuate the lock 2306 as described above and set a position of the implement 2006. The driver 2300 can be decoupled from the implement 2006, coupled to the opposing implement 2008, and the process can be repeated, including polyaxial positioning of the implement, as shown by arrows 2902 in FIG. 29, and selective locking against polyaxial movement by actuating the driver, as shown by arrow 2904 of FIG. 29.

In the embodiments described above, movement of the tissue manipulating implements any of toward and away from one another, e.g., to accomplish tissue retraction, can be accomplished using, for example, a driver coupled to the tissue manipulating implement or direct manipulating by a user. FIGS. 30-39 illustrate alternative embodiments that utilize a forceps or plier-like design including a pair of opposed handles that can control movement of opposed tissue manipulating implements relative to one another.

Figure 30:
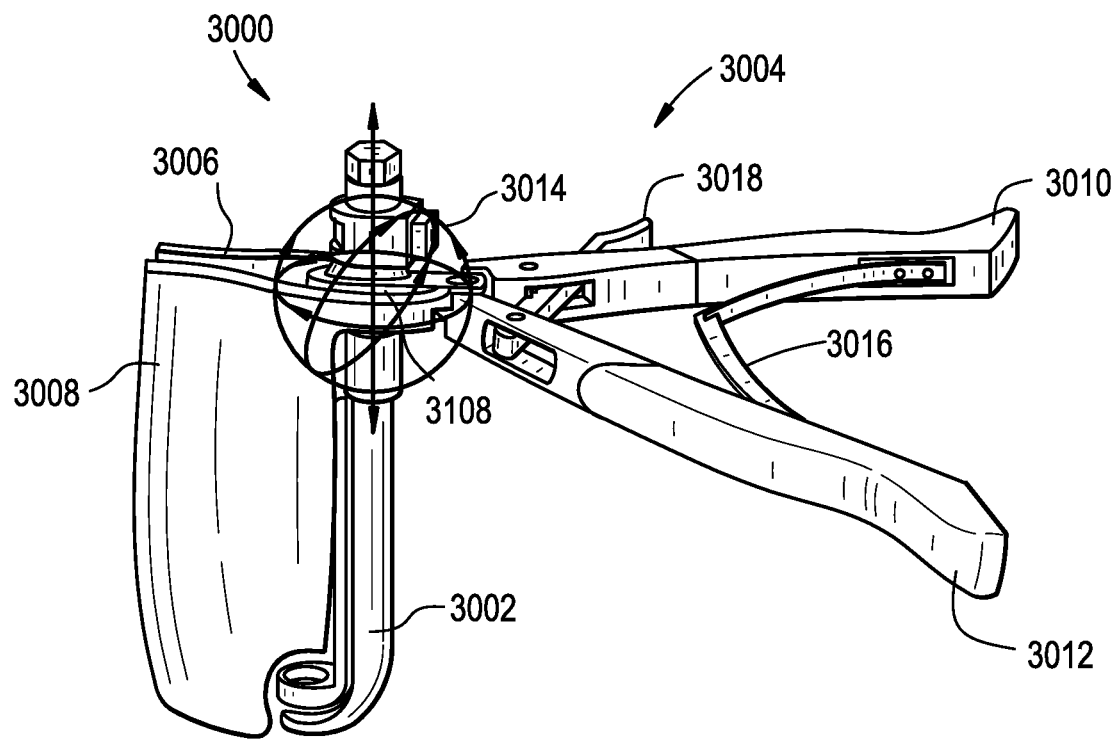
FIG. 30 is a side perspective view of one embodiment of a surgical instrument according to the teachings provided herein.

Turning to FIG. 30, for example, a surgical instrument assembly 3000 is illustrated that includes a support instrument 3002, similar to the instruments described above. A tissue retractor 3004 is coupled to the support instrument 3002 and includes first and second tissue manipulating implements 3006, 3008. The retractor 3004 also includes first and second handles 3010, 3012 disposed on an opposite side of the support instrument 3002 from the tissue manipulating implements 3006, 3008. The retractor 3004 can be coupled to the support instrument 3002 in a manner that permits the retractor to move polyaxially relative to the support instrument, as shown by arrows 3014. As explained in more detail below, movement of the opposed handles 3010, 3012 toward or away from one another can cause corresponding movement of the tissue manipulating implements 3006, 3008 toward or away from one another. In some embodiments, the handles 3010, 3012 can be biased toward to the illustrated open configuration by a spring 3016 or other biasing element. In some embodiments, an open configuration of the handles can correspond to a closed configuration of the tissue manipulating implements 3006, 3008 wherein the implements are near to one another. In such an embodiment, urging the handles 3010, 3012 toward one another against the biasing force of the spring 3016 can cause the tissue manipulating implements 3006, 3008 to pivot away from one another, e.g., to retract tissue forming the walls of an incision. Also shown in FIG. 30 is a lock 3018 that can be used to selectively maintain a position of the opposed handles 3010, 3012 (and thus the opposed tissue manipulating implements 3006, 3008) relative to one another.

Figure 31:
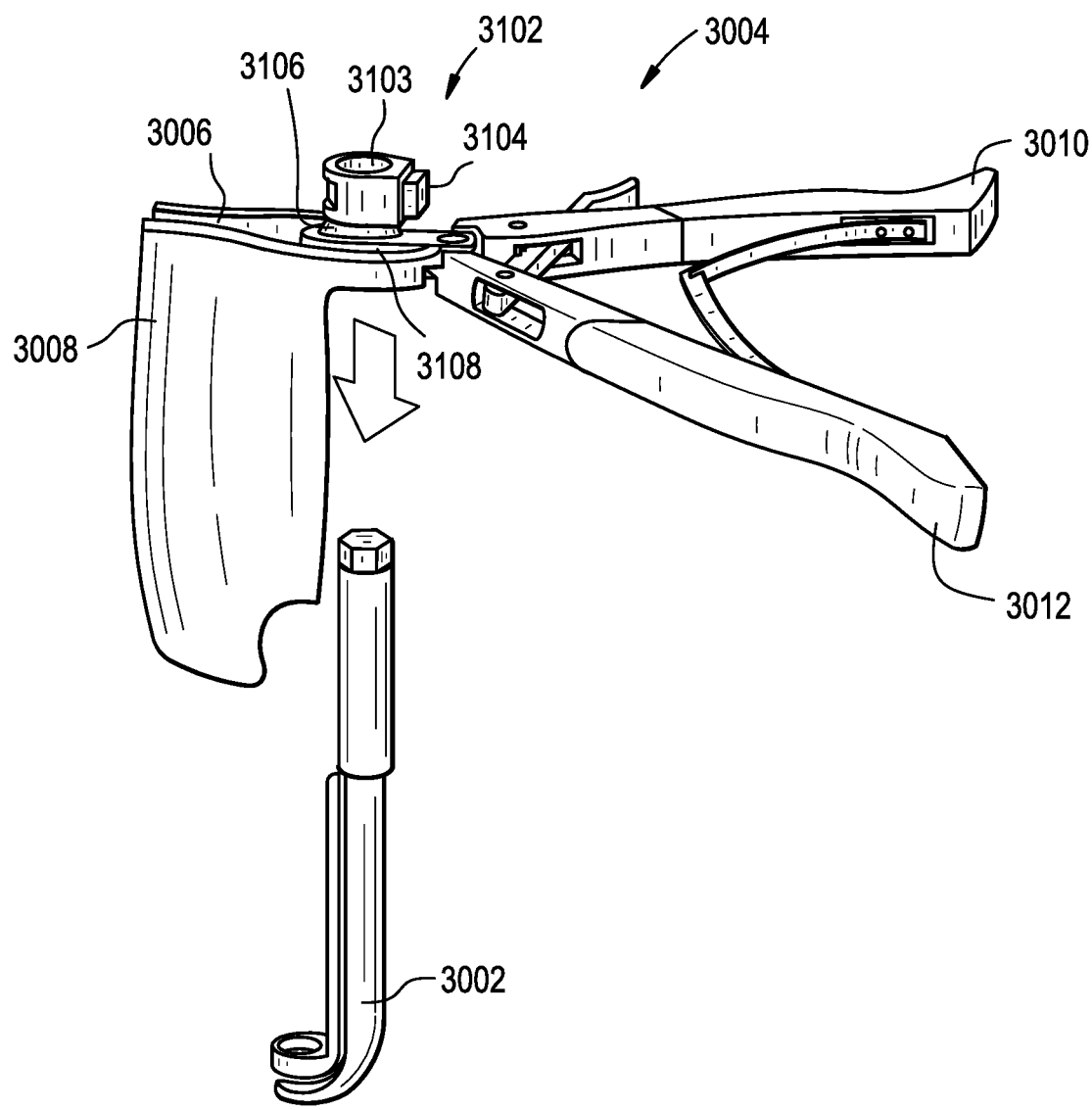
FIG. 31 is a side perspective view of the instrument of FIG. 30 coupling to an anchor extension.

FIG. 31 illustrates one embodiment of a method for coupling the retractor 3004 to the support instrument 3002. The retractor 3004 can include a joint 3102 having a lumen 3103 formed therethrough that can be sized to receive a proximal portion of the support instrument 3002. The joint 3102 can also include a locking element 3104, such as a spring-biased locking pin, protrusion, or other feature, that can engage a complementary recess or other feature formed in the support instrument 3002 to selectively lock a position of the retractor 3004 along a length of the support instrument. The joint 3102 can include a ball-shaped distal portion 3106 that can be seated within a socket 3108 of the retractor 3004, thereby providing for polyaxial movement of the tissue manipulating implements and the opposed handles relative to the joint 3102 and the support instrument 3002 coupled thereto. The polyaxial movement can be selectively locked in a variety of manners. For example, in some embodiments movement of the opposed handles 3010, 3012 can squeeze the ball-shaped distal portion 3106 of the joint 3102, thereby locking the retractor 3004 against movement relative to the joint 3102 and support instrument 3002. In other embodiments, however, a separately engageable locking mechanism for polyaxial movement can be included.

Figure 32:
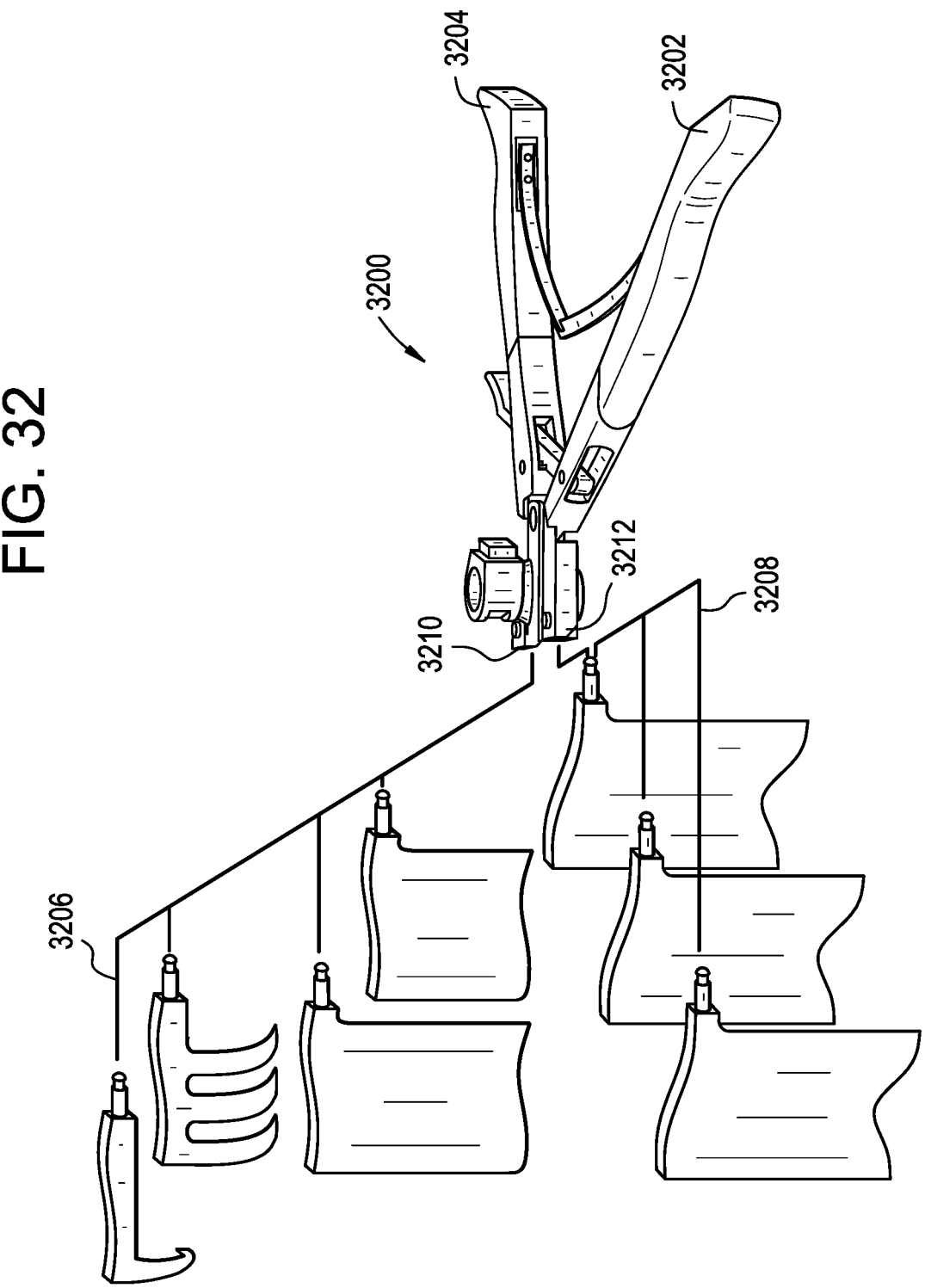
FIG. 32 is a side perspective view of a plurality of interchangeable tissue manipulating implements that can be coupled to the instrument of FIG. 30.

FIG. 32 illustrates an alternative embodiment in which a retractor 3200 with opposed actuating handles 3202, 3204 can be configured for modular connection with any of a plurality of tissue manipulating implements 3206, 3208. For example, a distal portion of the retractor 3200 can include recesses 3210, 3212 that can be configured to receive proximal ends of any of the various tissue manipulating implements 3206, 3208. Any of a variety of retention mechanisms can be utilized to secure the tissue manipulating implements 3206, 3208 to the retractor 3200, including locking pins, clips, magnets, etc. As described above, the various tissue manipulating implements 3206, 3208 can have any of a variety of shapes and sizes, and can be configured to retract soft tissue, scrape or separate soft tissue from bone, contact bone, etc.

Figure 33:
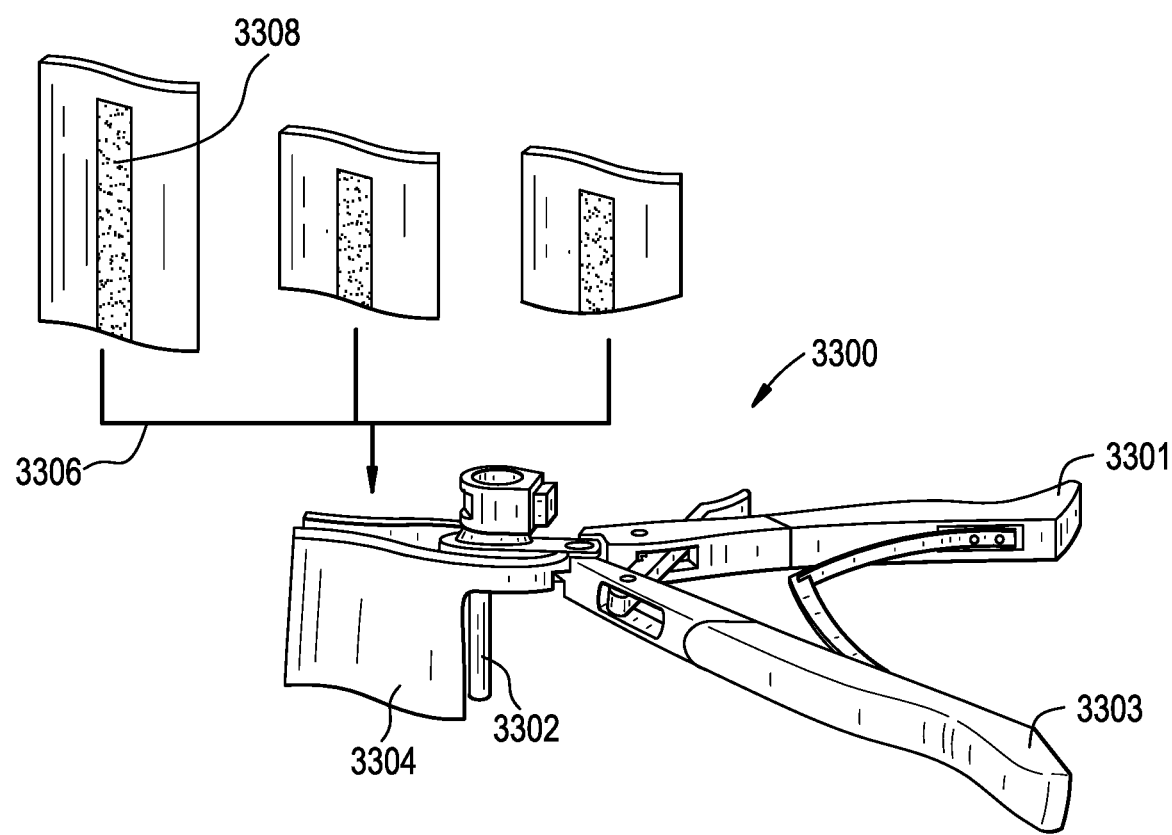
FIG. 33 is a side perspective view of an alternative plurality of interchangeable tissue manipulating implements that can be coupled to the instrument of FIG. 30.
Figure 36:
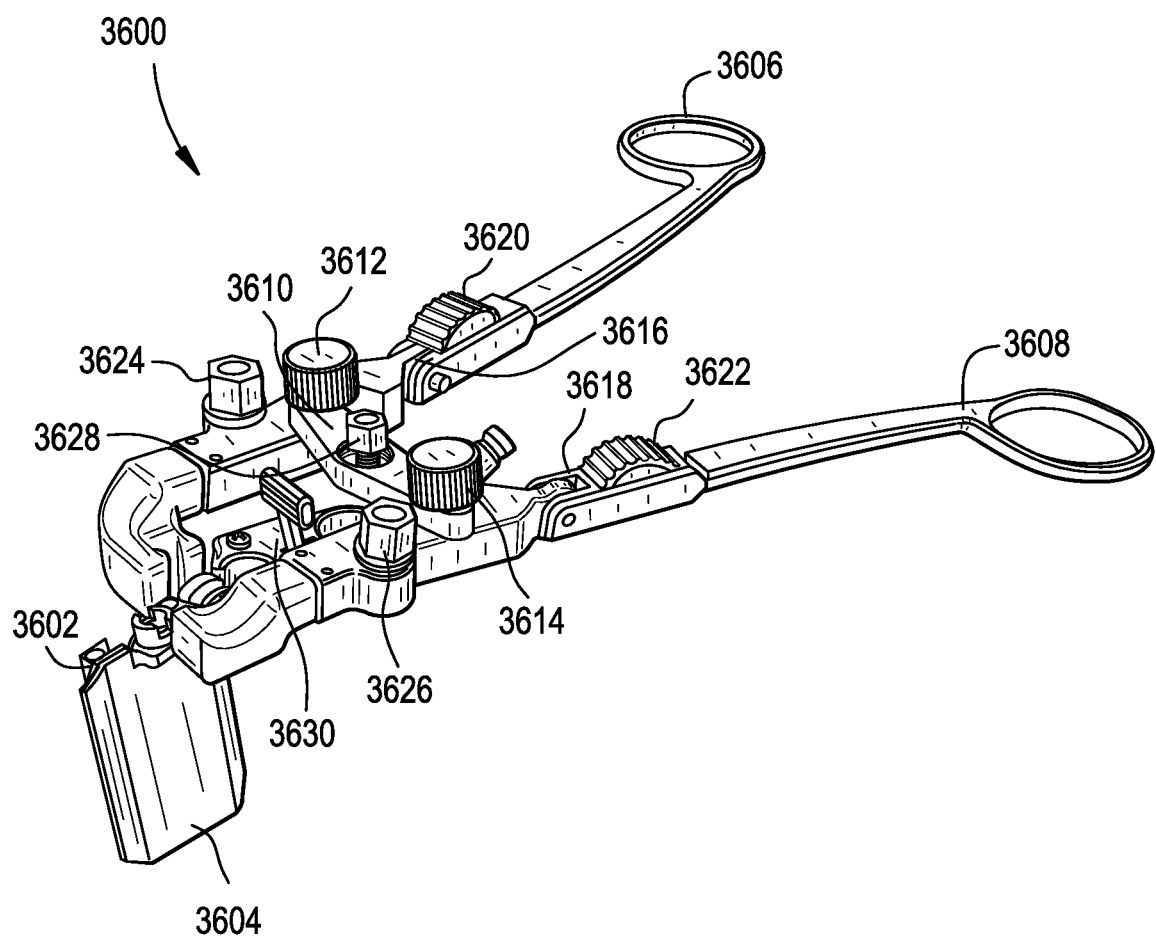
FIG. 36 is a front perspective view of another embodiment of a surgical instrument according to the teachings provided herein.

FIG. 33 illustrates another embodiment of a retractor 3300 that includes opposed tissue manipulating implements 3302, 3304 and opposed actuating handles 3301, 3303. The tissue manipulating implements 3302, 3304 can be configured to couple with any of a variety of extensions 3306 to provide adjustable length to the implements 3302, 3304. As described above, a relative position between an implement and an extension coupled thereto can be maintained in a variety of manners. For example, the extension 3306 can include a ratchet rack 3308 or other series of surface features formed thereon that can be engaged by a pawl, protrusion, or other surface feature formed on the tissue manipulating implement 3302, 3304.

FIGS. 34A-35 illustrate operation of the above-described retractor 3004 in greater detail. As shown in FIGS. 34A and 34B, moving the opposed handles 3010, 3012 toward one another in the direction of arrows 3402, 3404 can cause corresponding movement of the opposed tissue manipulating implements 3006, 3008 away from one another in the direction of arrows 3406, 3408. Accordingly, a user squeezing the opposed handles 3010, 3012 toward one another can cause the tissue manipulating implements 3006, 3008 to move apart, thereby retracting tissue abutting outer surfaces of the tissue manipulating implements. The lock 3018 can be engaged to maintain a position of the handles 3010, 3012 close to one another against the bias force of the spring 3016 or any compressive force applied to the tissue manipulating implements by retracted tissue.

When a user wishes to release any retracted tissue, the lock 3018 can be released by moving it in the direction of arrow 3502 shown in FIG. 35. This can allow the opposed handles 3010, 3012 to move in the direction of arrows 3504, 3506 away from one another. Such movement can cause corresponding movement of the tissue manipulating implements 3006, 3008 toward one another in the direction of arrows 3508, 3510. Such movement can return retracted tissue to its original position and return the tissue manipulating implements to a more streamlined configuration that can be used to insertion into, or withdrawal from, an incision.

FIGS. 36-39 illustrate an alternative embodiment of a retractor 3600 including opposed tissue manipulating implements 3602, 3604 and actuating handles 3606, 3608. The retractor 3600 can have a slightly different configuration from the retractor 3004 described above and can provide for additional movements of the tissue manipulating implements relative to one another. For example, in the illustrated embodiment the retractor 3600 can move the tissue manipulating implements 3602, 3604 any of toward and away from one another by corresponding movement of the actuating handles 3606, 3608, but can also allow for toeing of the tissue manipulating implements relative to one another using the rotating actuators 3624, 3626.

Figure 37:
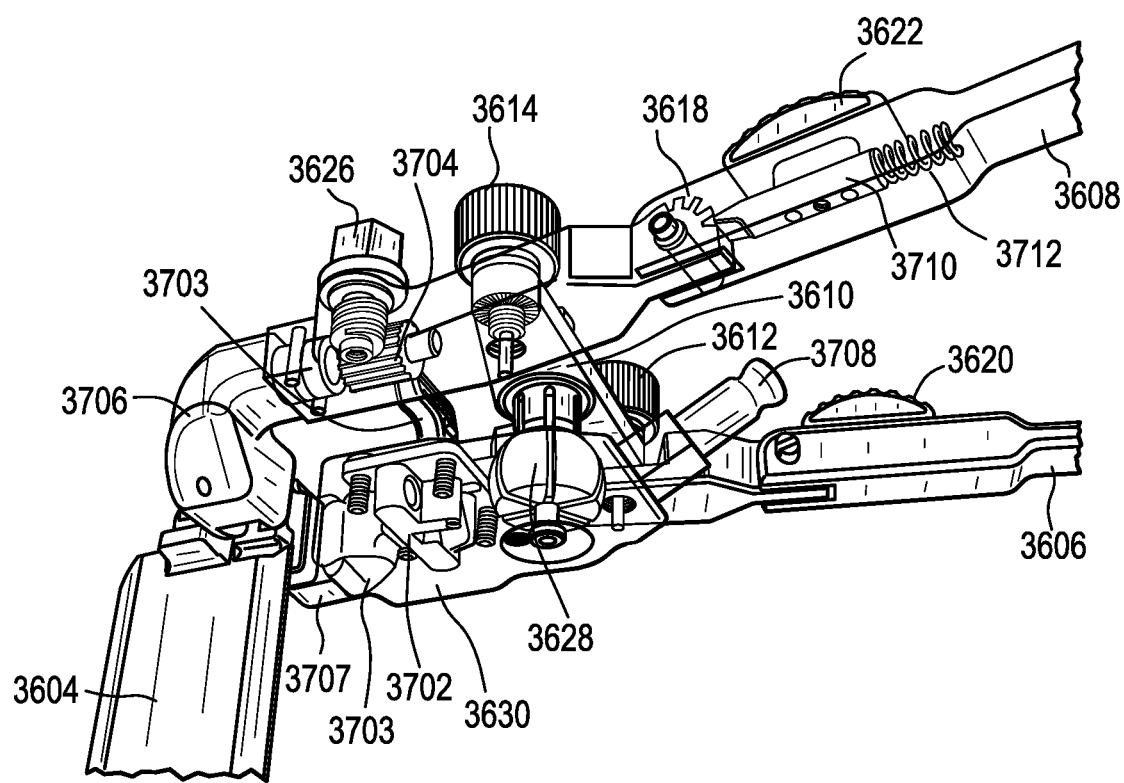
FIG. 37 is a partially transparent bottom perspective view of the instrument of FIG. 36.
Figure 38:
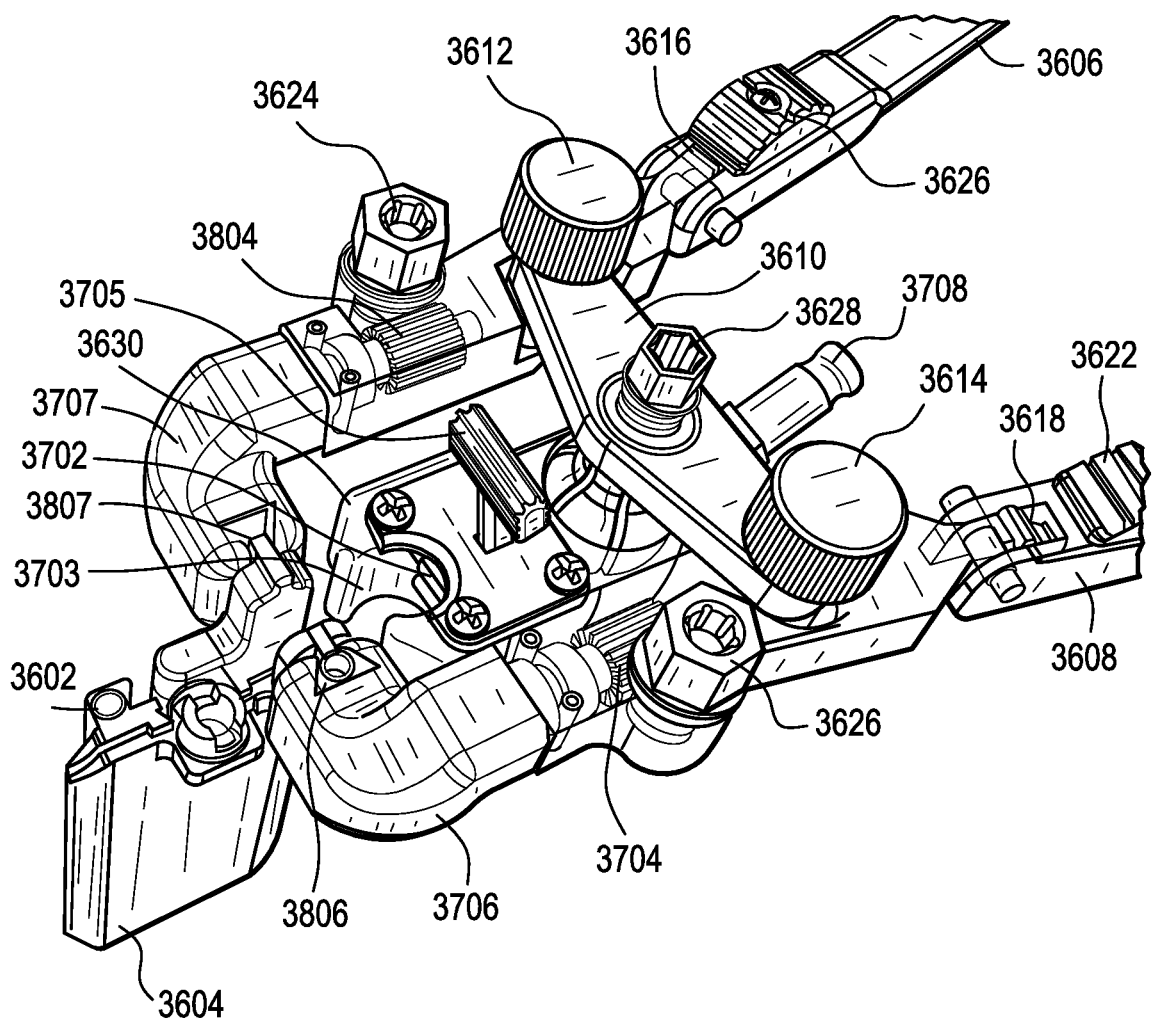
FIG. 38 is a partially transparent top perspective view of the instrument of FIG. 36.
Figure 39:
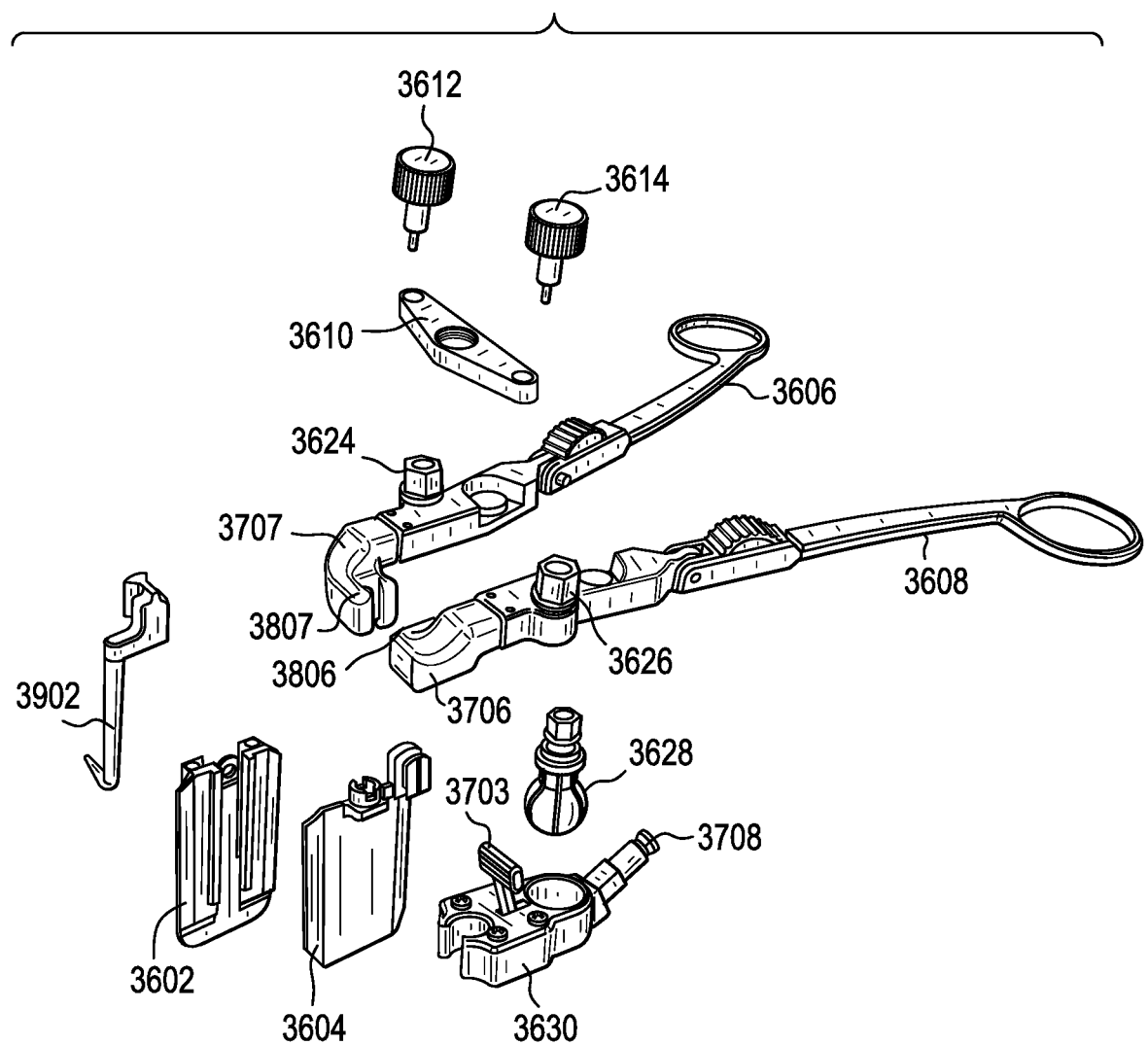
FIG. 39 is an exploded view of the instrument of FIG. 36.

As can be seen in the partially transparent views of FIGS. 37 and 38, the rotating actuators 3624, 3626 can include threads that mesh with gears 3704, 3804 to transfer rotation of the actuators into transverse rotation of the arms 3706, 3707 that couple to the tissue manipulating implements 3602, 3604 via slots 3806, 3807, as described above. Rotation of the arms 3706, 3707 can cause the coupled tissue manipulating implements 3602, 3604 to toe relative to one another such that distal ends thereof move any of toward and away from one another to a greater degree than proximal ends thereof such that the opposed tissue manipulating implements no longer extend parallel to one another.

In addition to toeing movement, the tissue manipulating implements 3602, 3604 can be moved any of toward and away from one another by movement of the opposed handles 3606, 3608. Each handle and associated tissue manipulating implement can pivot relative to a central body 3610. Further, a rotating lock 3612, 3614 can be provided to selectively lock a position of each handle and tissue manipulating implement relative to the body 3610. Further, a proximal portion of each handle 3606, 3608 can be pivoted relative to a distal portion thereof in order to, for example, reduce a footprint of the retractor 3600 when the handles are not in use or to angle the handles around surrounding instrumentation. A ratchet 3616, 3618 or other series of recesses or surface features can be formed around a curved proximal surface of a distal portion of each handle 3606, 3608 and the proximal portion of each handle can be pivotably coupled thereto. A pawl 3710 or other similar component in each arm can be biased by a spring 3712 to interface with the ratchet 3616, 3618. Moreover, a sliding lever 3620, 3622 can be coupled to the pawl in each handle to allow a user to selectively draw the pawl away from the ratchet and permit pivoting movement of the proximal portion of each handle relative to a distal portion thereof.

The retractor 3600 can be polyaxially coupled to a support instrument in a manner similar to the retractor 3004 described above. For example, a support coupler 3630 can be coupled to the body 3610 using a selectively lockable polyaxial joint 3628, e.g., a joint similar to the ball-and-socket locking joints described herein. The support coupler 3630 can include lumen or recess 3703 configured to couple with an elongate body of a support instrument, as well as a spring biased movable pawl or protrusion 3702 that can engage a complementary recess or other feature formed along a length of the support instrument to selectively lock a position of the retractor 3600 relative to the support instrument. In some embodiments, a lever 3705 can be provided to aid a user in selectively disengaging the locking feature 3702 to allow free sliding movement of the retractor 3600 relative to a support instrument. In addition to locking the support coupler 3630 at a desired position along a length of a support instrument using the protrusion 3702, the polyaxial joint 3628 can be selectively locked to prevent movement of the tissue manipulating implements 3602, 3604 and handles 3606, 3608 relative to the support coupler 3630. As with other embodiments described herein, any of a variety of modular tissue manipulating implements 3602, 3604, 3902 can be utilized with the retractor 3600.

Figure 40:
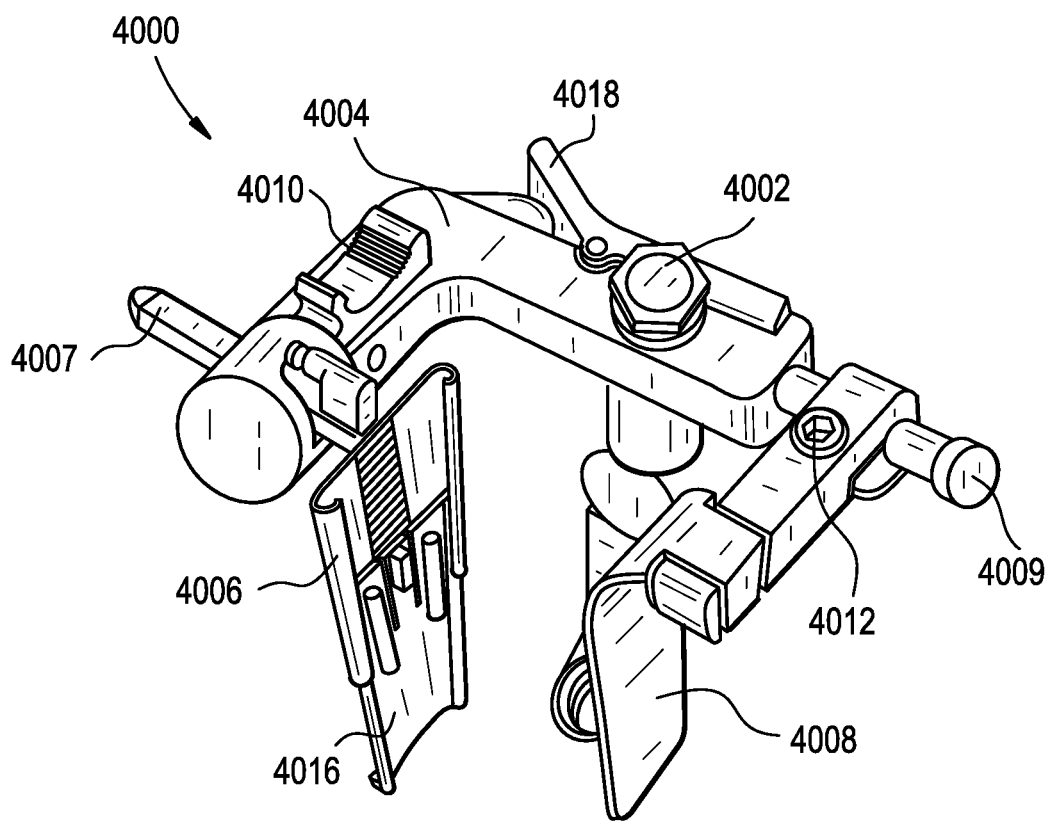
FIG. 40 is a front perspective view of one embodiment of a surgical instrument assembly according to the teachings provided herein.

FIGS. 40-61 illustrate still other embodiments of a tissue retractor assembly based on a concept of a modular scaffold that can be added to as desired and coupled to a support instrument that is coupled to a single implantable anchor. For example, FIG. 40 illustrates one example of such a retractor assembly 4000 that includes a base 4004 coupled to a support instrument 4002 that is coupled to an implantable anchor, such as a bone screw. The base 4004 can be selectively locked at a desired position along a length of the support instrument 4002 using, for example, a pivoting lever 4018 having a pawl or locking pin coupled to one end thereof that can engage a complementary feature on the support instrument 4002. A first tissue manipulating implement 4006 can be coupled to the base 4004 and a second tissue manipulating implement 4008 can be coupled to an opposite side of the base such that the two tissue manipulating implements are disposed opposite one another. A position of the tissue manipulating implement 4006 can be adjusted along a lateral adjustment shaft 4007 extending therefrom to allow the implement 4006 to translate toward or away from the opposed implement 4008. The implement 4006 can also be rotated relative to the implement 4008 and locked at a desired position using a lock 4010. The second implement 4008 can be coupled to an extension shaft 4009 extending from the base 4004. The implement can be positioned along a length of the shaft 4009 and rotated thereabout to a desired position, then a locking screw 4012 can be used to prevent further movement of the implement 4008 relative to the base 4004. As with the embodiments described above, a number of additional features are possible, including, for example, the use of an extension 4016 to adjust a length of either of the first and second tissue manipulating implements 4006, 4008.

Figure 41:
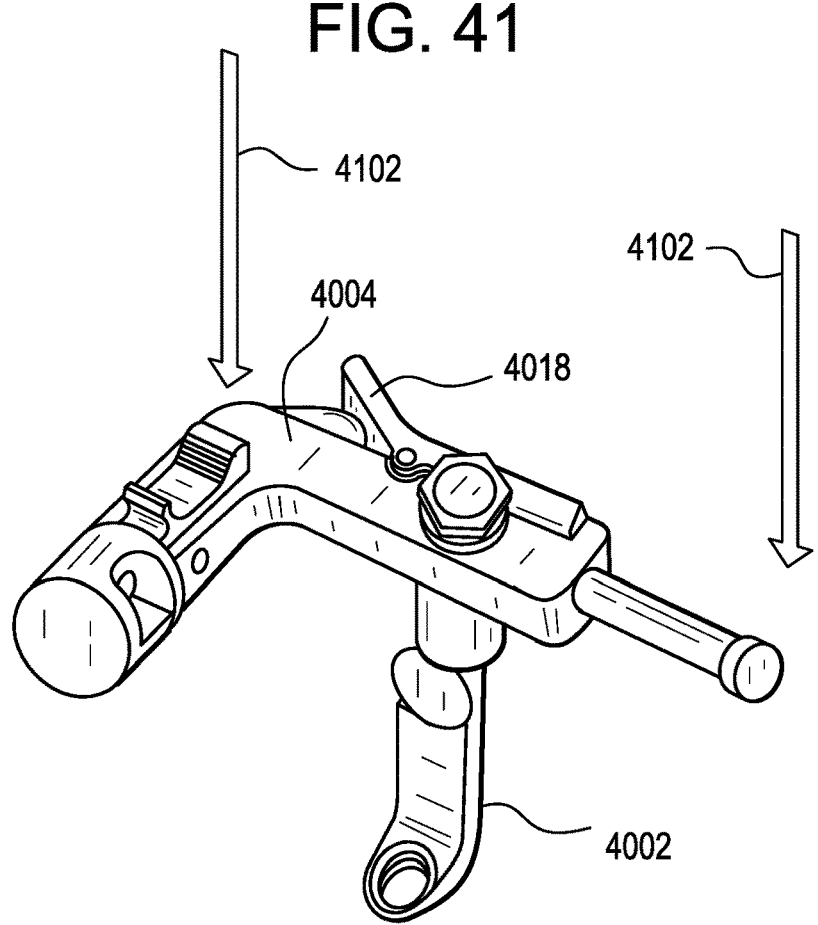
FIG. 41 is a front perspective view of a first component of the surgical instrument assembly of FIG. 40.
Figure 42:
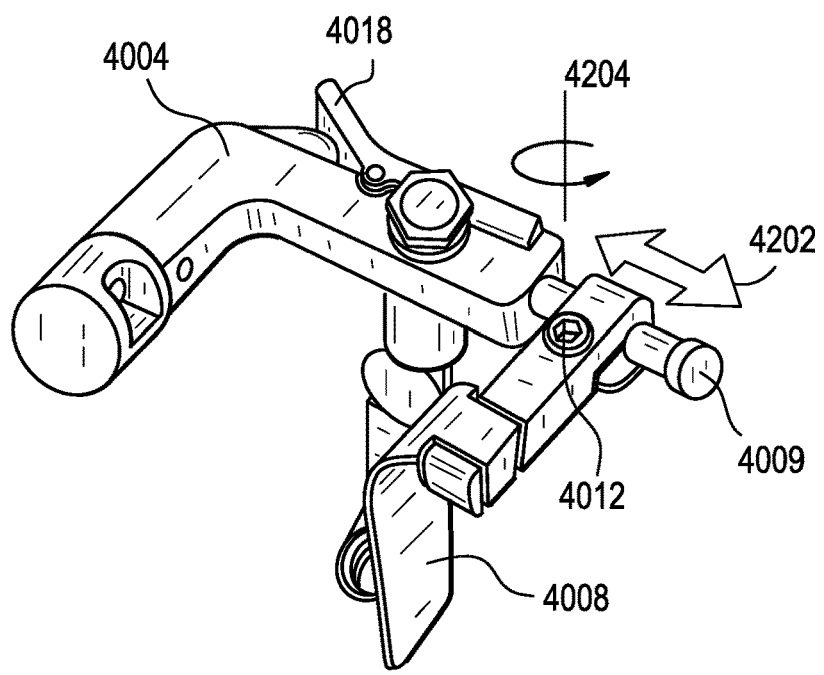
FIG. 42 is a front perspective view of a second component of the surgical instrument assembly of FIG. 40 coupling with the first component of FIG. 41.

FIGS. 41-50 illustrate one embodiment of a method for constructing the tissue retractor assembly 4000 shown in FIG. 40. As shown in FIG. 41, for example, the base 4004 can be coupled to the support instrument 4002 by passing the base down or distally in the direction of arrows 4102 such that a proximal portion of the support instrument 4002 is received within a lumen formed in the base. The lock 4018 can be utilized to set a desired position of the base 4004 along a length of the support instrument 4002. As shown in FIG. 42, the tissue manipulating implement 4008 can then be coupled to the shaft 4009 that extends from one side of the base 4004. The implement 4008 can be translated along a length of the shaft 4009 in the direction of arrows 4202, as well as rotated about the shaft. When a desired positon is reached, the locking screw 4012 can be rotated in the direction of arrow 4204 to lock a position of the implement 4008 relative to the shaft 4009.

Figure 43:
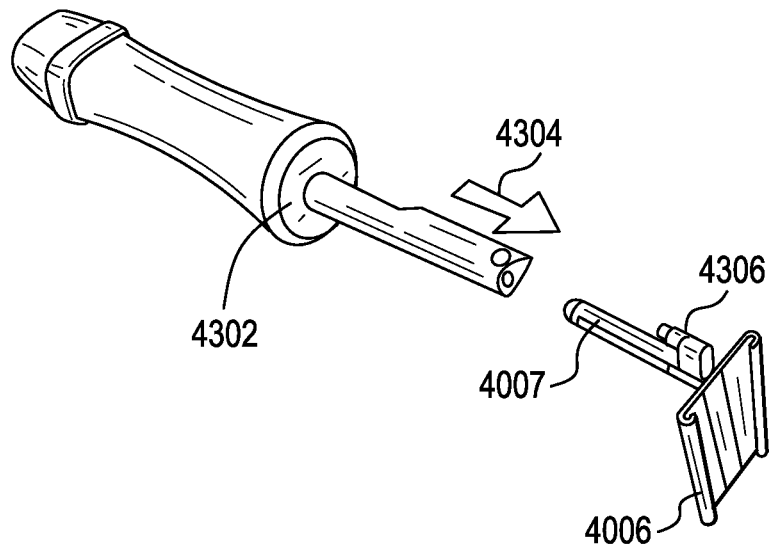
FIG. 43 is a front perspective view of a first component of one embodiment of a tissue manipulating implement.
Figure 44:
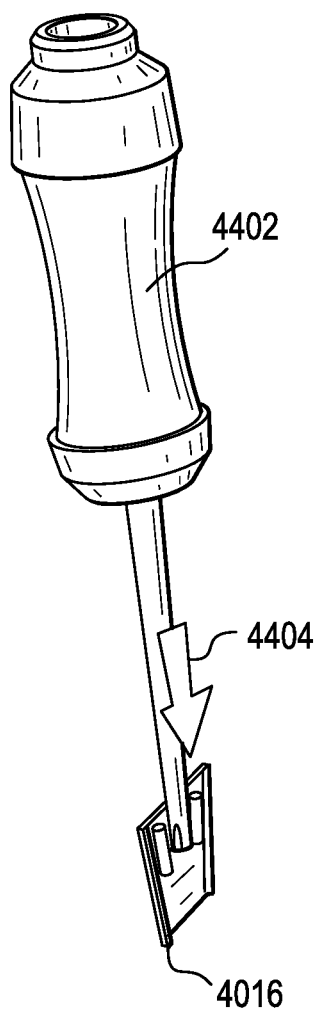
FIG. 44 is a front perspective view of a second component of the tissue manipulating implement of FIG. 43.
Figure 45:
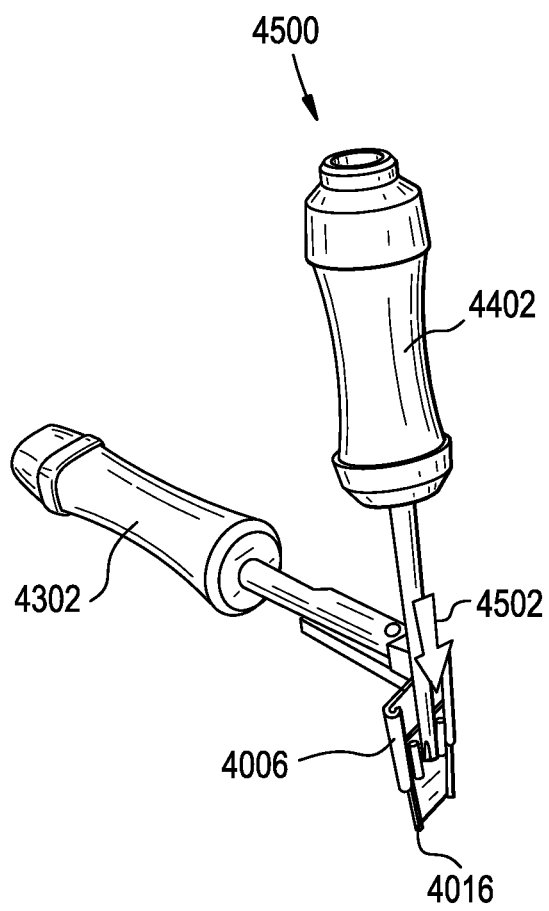
FIG. 45 is a front perspective view of the first component of FIG. 43 coupling with the second component of FIG. 44.

The tissue manipulating implement 4006 and its extension 4016 can be assembled in a different manner. As shown in FIG. 43, for example, the tissue manipulating implement 4006 and the lateral adjustment shaft 4007 extending therefrom can be coupled to an insertion instrument 4302 by advancing the instrument in the direction of the arrow 4304 such that a distal end of the instrument interfaces with (e.g. receives, extends into, or otherwise couples with) a mating post 4306 coupled to the shaft 4007. Separately, a second instrument 4402 can couple to the extension 4016 by advancing a distal end of the instrument in the direction of arrow 4404, as shown in FIG. 44. The implement 4006 and extension 4016 can be joined together by sliding the extension 4016 in the direction of arrow 4502 in FIG. 45 to create the tissue manipulating implement assembly 4500.

Figure 46:
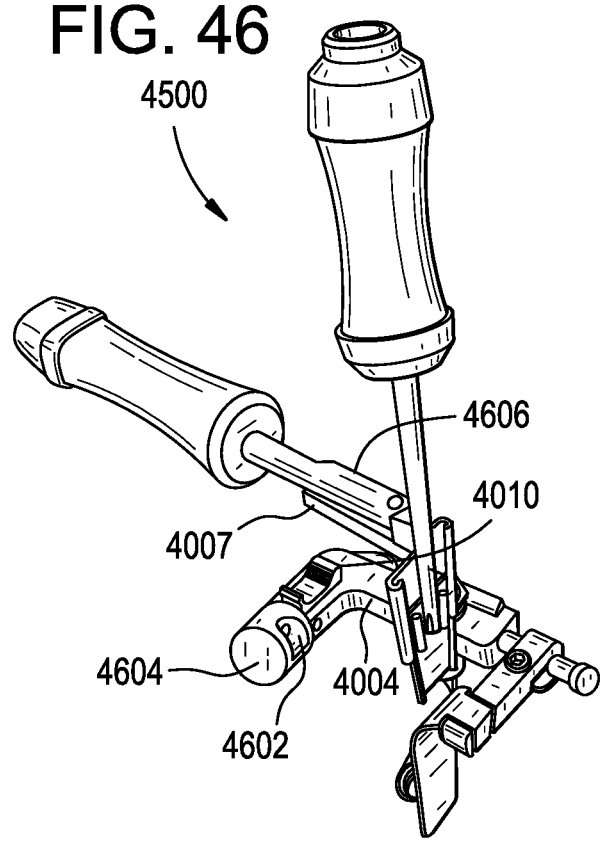
FIG. 46 is a front perspective view of the tissue manipulating implement of FIGS. 43-45 coupling to the assembly of FIG. 40.
Figure 47:
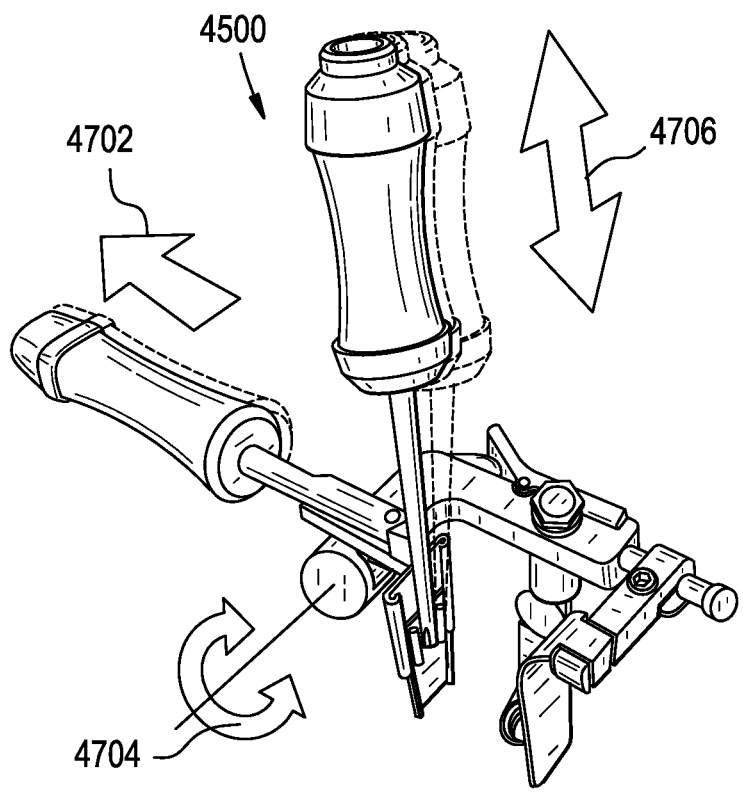
FIG. 47 is a front perspective view of the assembly of FIG. 46 illustrating various degrees of freedom of a tissue manipulating implement.

FIG. 46 illustrates one embodiment of a method for coupling the tissue manipulating implement assembly 4500 to the base 4004. Specifically, the lateral adjustment shaft 4007 of the assembly 4500 can be inserted through a through-hole 4602 formed in a rotating portion 4604 of the base 4004. As the shaft 4007 is inserted into the through-hole 4602, a ridge 4606 formed along a distal portion of the instrument 4302 can urge the lock 4010 against a biasing force away from the rotating portion 4604 of the base 4004, thereby freeing motion of the rotating portion relative to the base 4004. Accordingly, once inserted as shown in FIG. 47, a position of the tissue manipulating implement 4006 can be adjusted in multiple dimensions by moving the assembly 4500 relative to the base 4004 in the direction of any of the arrows 4702, 4704, 4706 in FIG. 47.

Figure 48:
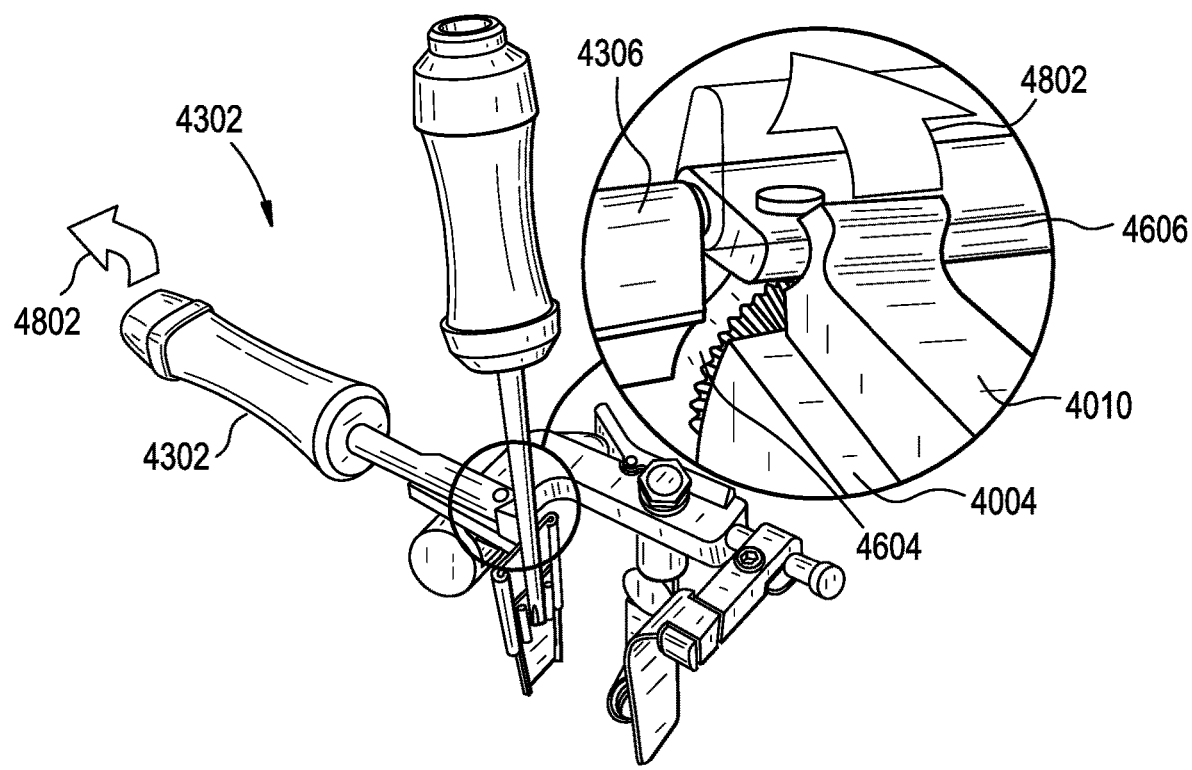
FIG. 48 is a detail view of the assembly of FIG. 46 illustrating one embodiment of a lock to selectively prohibit movement of a tissue manipulating implement.

Once a desired position of the implement 4006 is achieved, the instrument 4302 can be rotated in the direction of arrow 4804 in FIG. 48 to cause the ridge 4606 to move out of engagement with the lock 4010. The lock 4010 can then be urged into contact with the rotating portion 4604 of the base 4004 by a biasing force, thereby preventing further rotation of the portion 4604 relative to the base 4004. In some embodiments, the lock 4010 can also be configured to lock the lateral adjustment shaft 4007 against translation through the through-hole 4602, such that the lock 4010 can set a lateral position of the implement 4006 as well as an angle of rotation relative to the base 4004. In other embodiments, however, a separate lock can be employed to selectively permit or prevent translation of the shaft 4007 (and implement 4006 coupled thereto) through the through-hole 4602.

Figure 49:
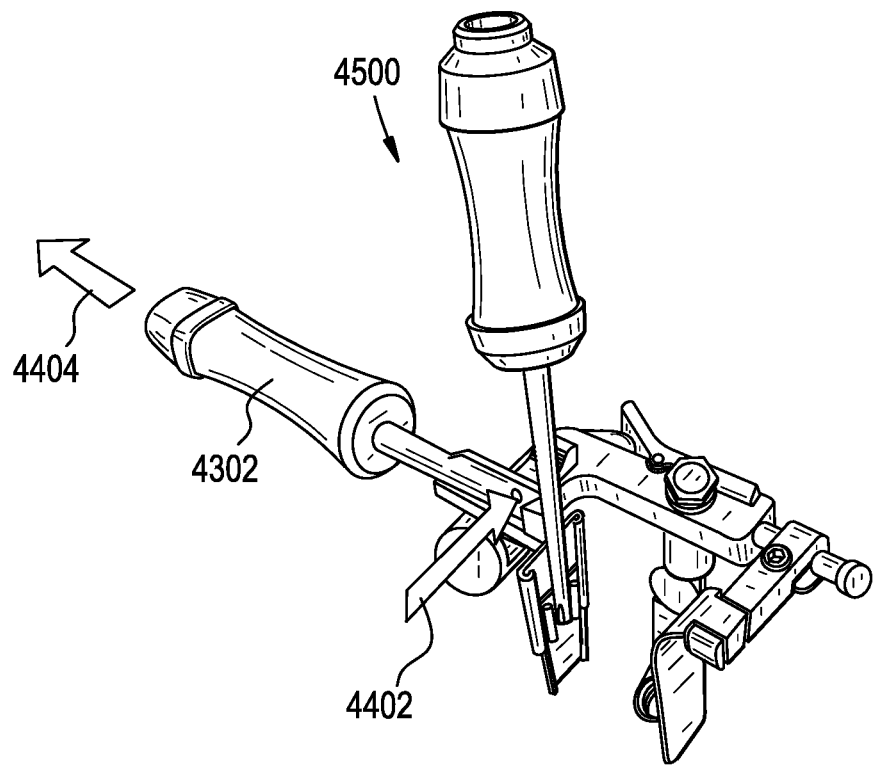
FIG. 49 is a front perspective view of the assembly of FIG. 47 illustrating removal of a first driver.
Figure 50:
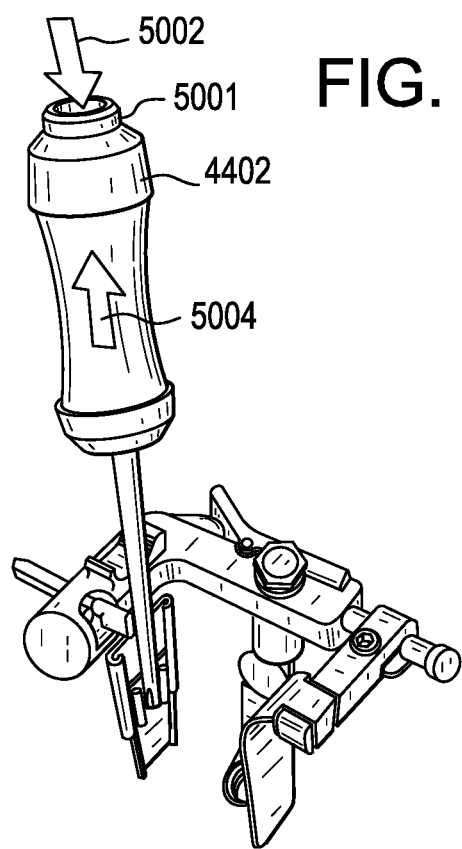
FIG. 50 is a front perspective view of the assembly of FIG. 47 illustrating removal of a second driver.
Figure 51:
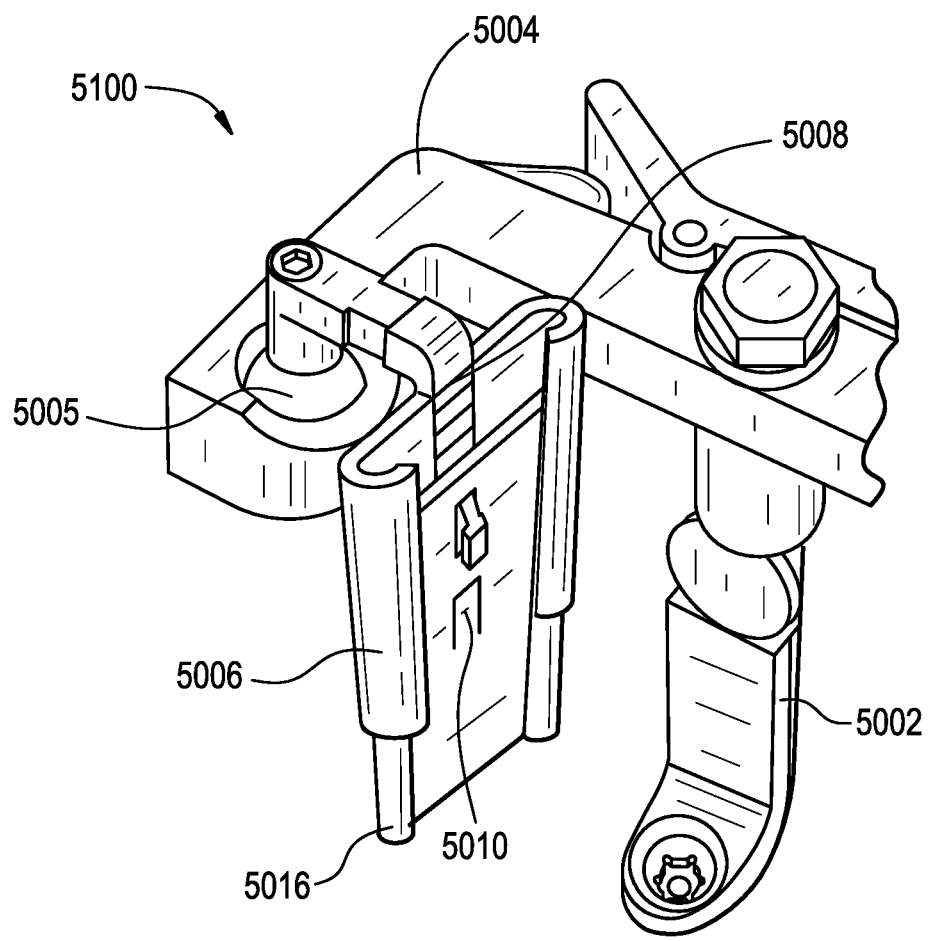
FIG. 51 is a detail view illustrating an alternative embodiment of a tissue manipulating implement coupling to the assembly of FIG. 40.

As shown in FIG. 49, the instrument 4302 can be separated from the implement 4006 by pressing a release button 4902 to free a distal end of the instrument from the mating post 4306 and withdrawing the instrument in the direction of arrow 4904. The instrument 4402 can be separated from the extension 4016 by, for example, depressing a release button 5001 in the direction of arrow 5002 and withdrawing the instrument 4402 in the direction of arrow 5004.

FIGS. 51-54 illustrate an alternative embodiment of a retractor assembly 5100 in which a support instrument 5002 coupled to an implantable anchor can be coupled to a modular scaffold base 5004 that includes a ball-and-socket polyaxial joint 5005 to permit polyaxial movement of a tissue manipulating implement 5006 relative to the base. As with embodiments described above, the tissue manipulating implement 5006 can include an extension 5016 coupled thereto that can translate relative to the implement to adjust an overall length thereof. A desired position of the extension 5016 relative to the implement 5006 can be maintained using a ratchet rack 5008 and spring pawl 5010 or other similar cooperating components.

FIGS. 52-54 illustrate one embodiment of a method for constructing the modular scaffold retractor assembly 5100. As described above, a modular scaffold base 5004 can be coupled to a support instrument 5002 that is itself coupled to an implantable anchor. The tissue manipulating implement 5006, which can include a ball-shaped proximal portion 5204 configured to be received within a socket 5202 formed in the base 5004, can be coupled to an instrument 5206.

Further, the extension 5016, which can be coupled to another instrument 5304, can be slidably coupled to the implement 5006 as shown by arrow 5208 in FIG. 52. The instruments 5206 and 5304 can then be used to guide the implement 5006 and extension 5016 toward the base 5004 in the direction of arrow 5302 to seat the ball-shaped portion 5204 in the socket 5202, as shown in FIG. 53. The tissue manipulating implement 5006 can then be moved polyaxially relative to the base 5004, as shown by the arrows 5402 in FIG. 54. Further, a position of the extension 5016 relative to the implement 5006 can be adjusted by moving the extension in the direction of arrows 5406 using instrument 5304. Once a desired position is achieved, the polyaxially joint 5004 can be locked using the instrument 5206, a position of the extension 5016 relative to the implement 5006 can be locked, and both instruments 5206,5304 can be separated from the retractor assembly 5100.

Figure 55:
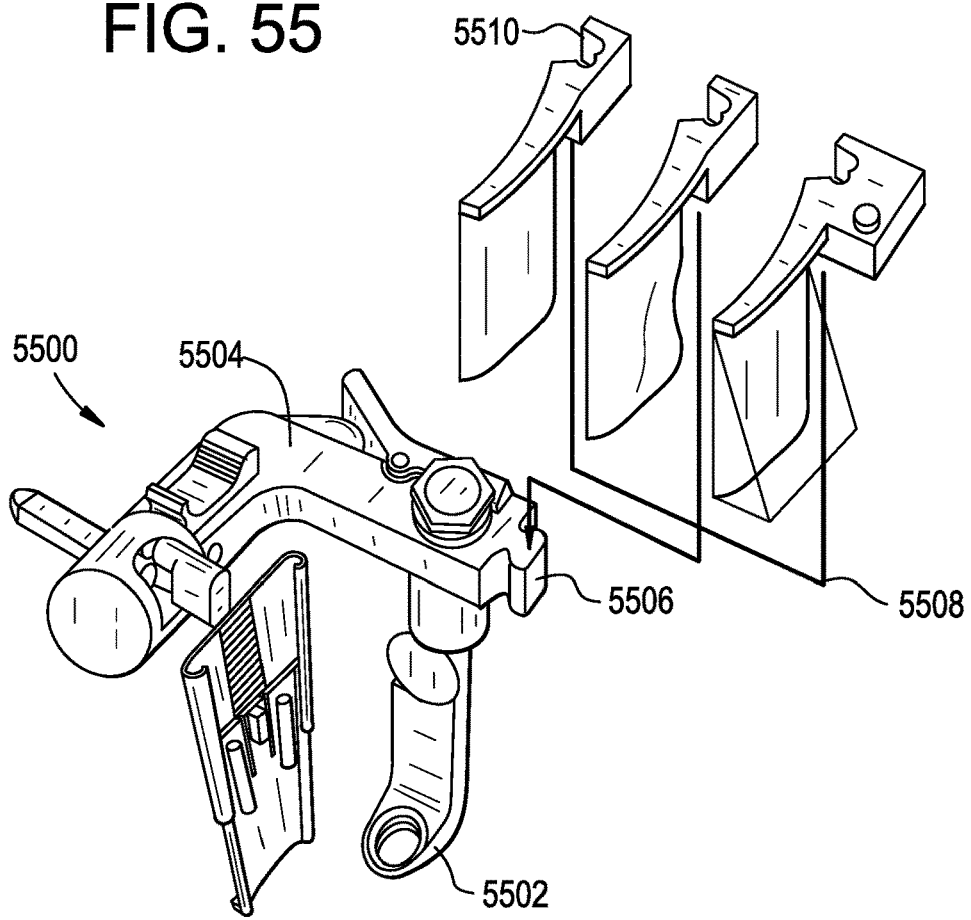
FIG. 55 is a detail view illustrating various interchangeable tissue manipulating implements that can be coupled to a surgical instrument assembly.
Figure 56:
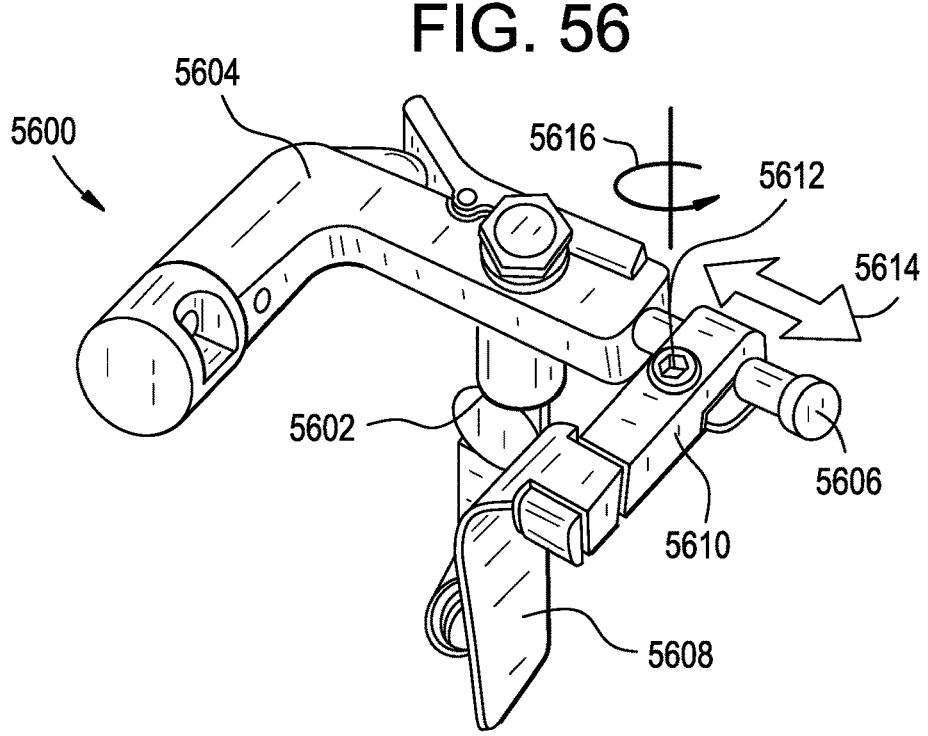
FIG. 56 is a detail view illustrating various degrees of freedom of a tissue manipulating implement of a surgical instrument assembly.
Figure 57:
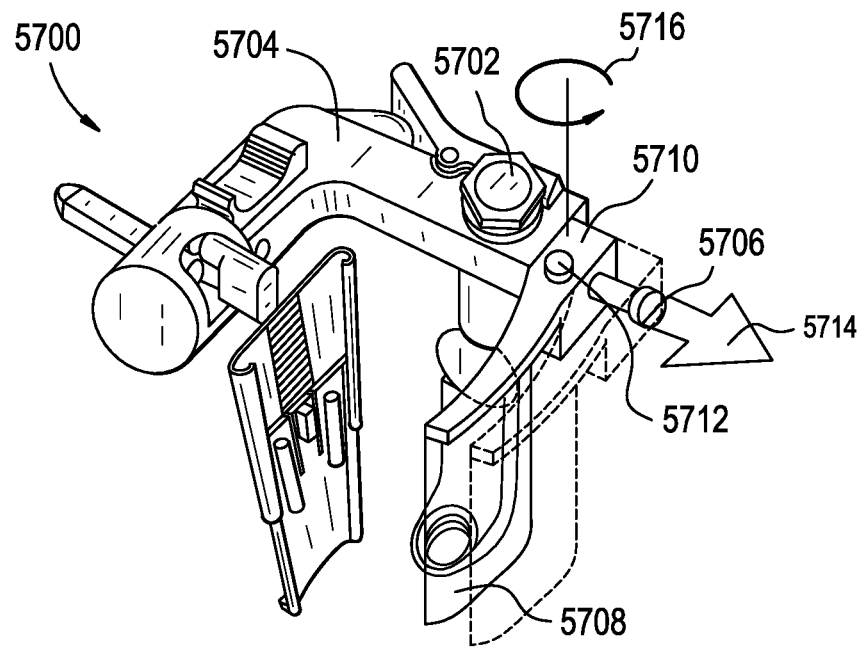
FIG. 57 is an alternative view of various degrees of freedom of a tissue manipulating implement of a surgical instrument assembly.

FIGS. 55-57 illustrate alternative embodiments for coupling the tissue manipulating implement 4008 that is disposed opposite the tissue manipulating implement 4006. For example, the retractor 5500 of FIG. 55 includes a base 5504 that can couple to a support instrument 5502 and can include a modular coupling 5506 that can be used to couple any of a variety of tissue manipulating implements 5508 to the base. For example, the modular coupling 5506 can include a protrusion extending from the base and each of the modular tissue manipulating implements 5508 can include a complementary-shaped recess 5510 formed therein to permit coupling with the base 5504. As described above, a number of variations on this type of coupling are also possible.

The retractor assembly 5600 of FIG. 56 is similar to the retractor 4000 of FIG. 40 and employs a shaft 5606 that extends from a base 5604 that is coupled to a support instrument 5602. The tissue manipulating implement 5608 is coupled to the shaft 5606 by a link 5610 that can be selectively tightened about the shaft 5606 by a locking screw 5612. Accordingly, when the screw 5612 is appropriately loosened, the implement 5608 and link 5610 can be translated along the shaft 5606 in the direction of arrows 5614 and/or rotated about the shaft until the locking screw 5612 is rotated in the direction of arrows 5616 to a sufficient degree to prevent movement between the link 5610 and the shaft 5606.

The retractor assembly 5700 of FIG. 57 illustrates still another embodiment in which a base 5704 coupled to a support instrument 5702 includes a shaft 5706 extending therefrom that includes a ratchet rack, gear teeth, or other series of surface features formed thereon. A tissue manipulating implement 5708 can include a proximal portion 5710 disposed around the shaft 5706 and can include an actuator 5712, such as a gear, etc. Rotation of the actuator 5712 in the direction of arrow 5716 can cause the tissue manipulating implement 5708 to advance laterally along the shaft 5706 in the direction of the arrow 5714. Such advancement can be utilized, for example, to retract tissue abutting against the tissue manipulating implement 5708.

Figure 58:
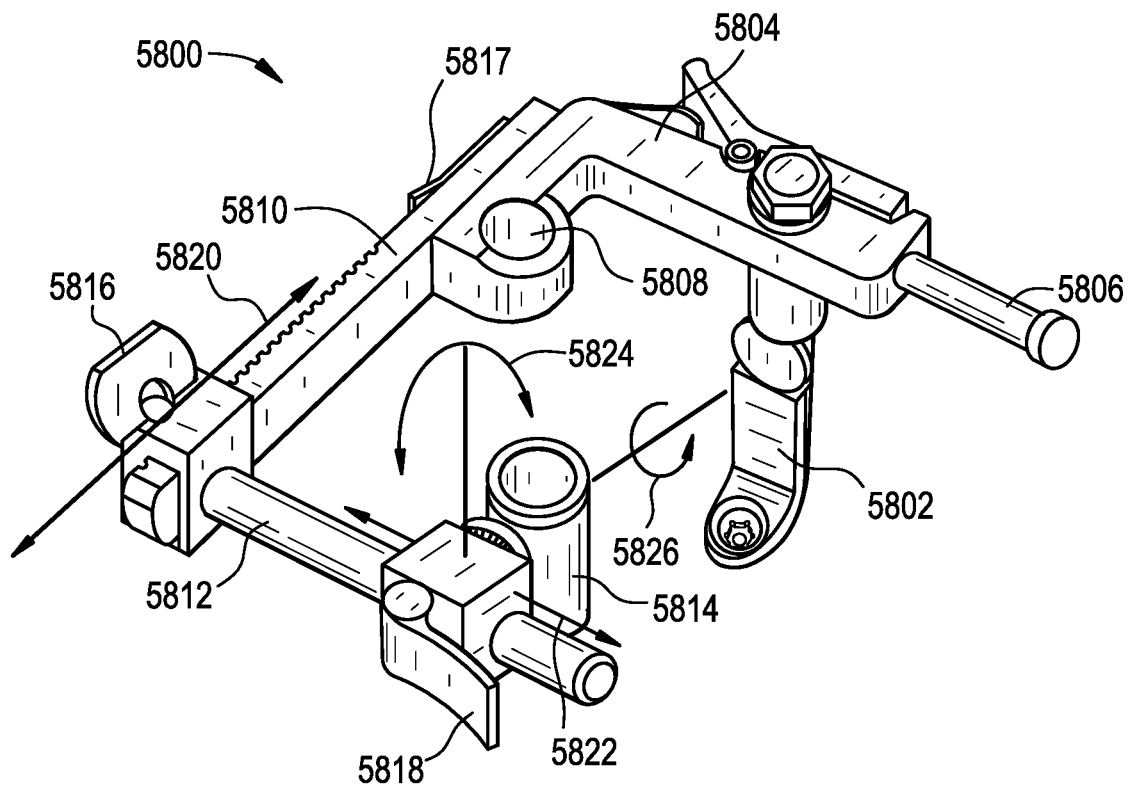
FIG. 58 is a front perspective view of one embodiment of a surgical instrument assembly that can perform vertebral distraction.

In some embodiments, a modular scaffold-based tissue retractor assembly can be further expanded to perform other operations, including, for example, vertebral distraction. FIGS. 58-61 illustrate one embodiment of a tissue retractor assembly 5800 that can be used for such a purpose. As shown in FIG. 58, the retractor assembly 5800 can include a base 5804 coupled to a support instrument 5802 that is coupled to an implanted anchor (not shown). As in the embodiments described above, the base 5804 can include a shaft 5806 extending from one end thereof for coupling with a tissue manipulating implement (not shown), as well as a socket 5808 for coupling with a second tissue manipulating implement (not shown).

Also coupled to the base 5804 is a distraction rack 5810, which can secure to the base 5804 using a lock 5817, such as a spring-biased locking pin or pawl. A post 5812 is coupled to the distraction rack 5810 and a screw extension receiver 5814 is coupled to the post. The post 5812 can be translated along a length of the distraction rack 5810 in the direction of arrows 5820 using a rotating actuator 5816 that can be coupled to, e.g., a gear that interfaces with gear teeth or other surface features formed along a length of the distraction rack. The screw extension receiver 5814 can be translated along the post 5812 in the direction of arrows 5822, rotated about the post in the direction of arrows 5824, and rotating about an axis transverse to the post in the direction of arrows 5826. Further, a cam 5818 or other lock can be included to lock any or all of the above-listed degrees of freedom of the receiver 5814.

Figure 59:
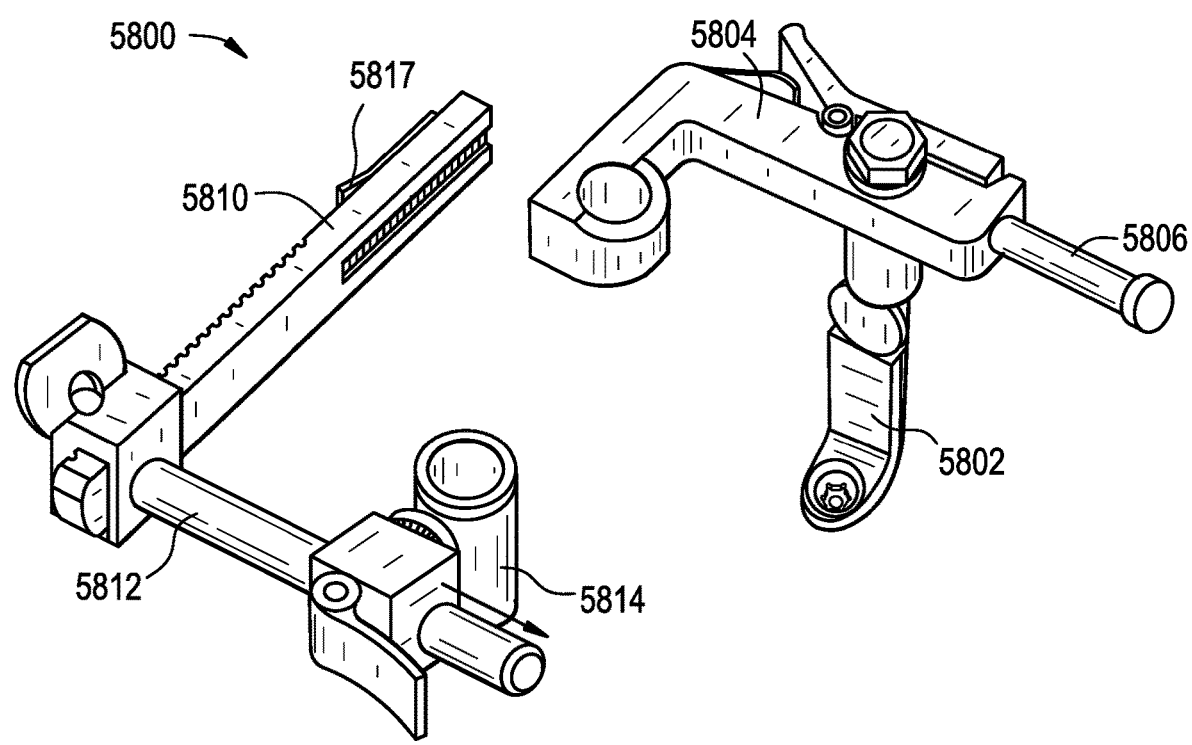
FIG. 59 is a detail view showing a first step in operating the surgical instrument assembly of FIG. 58.
Figure 60:
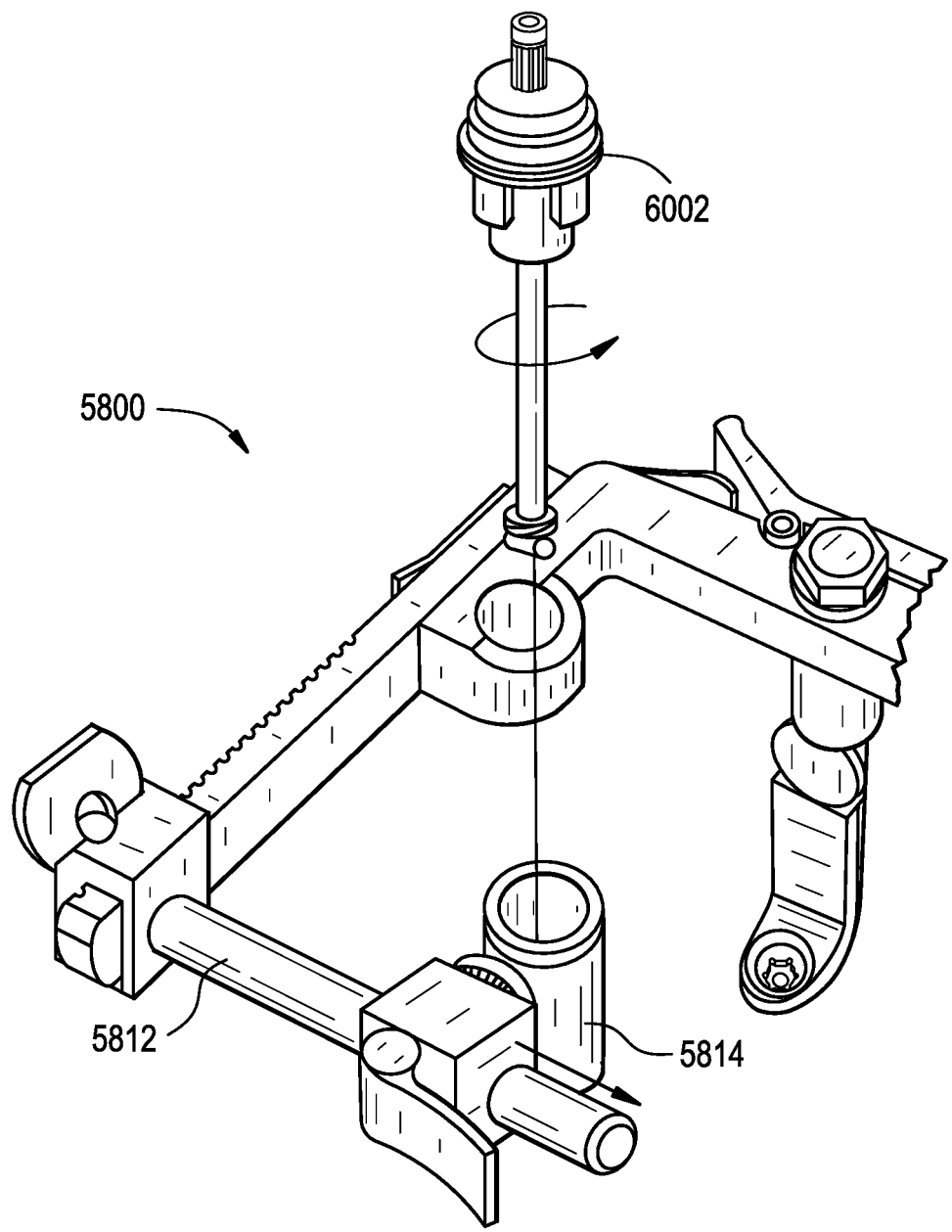
FIG. 60 is a detail view showing a second step in operating the surgical instrument assembly of FIG. 58.
Figure 61:
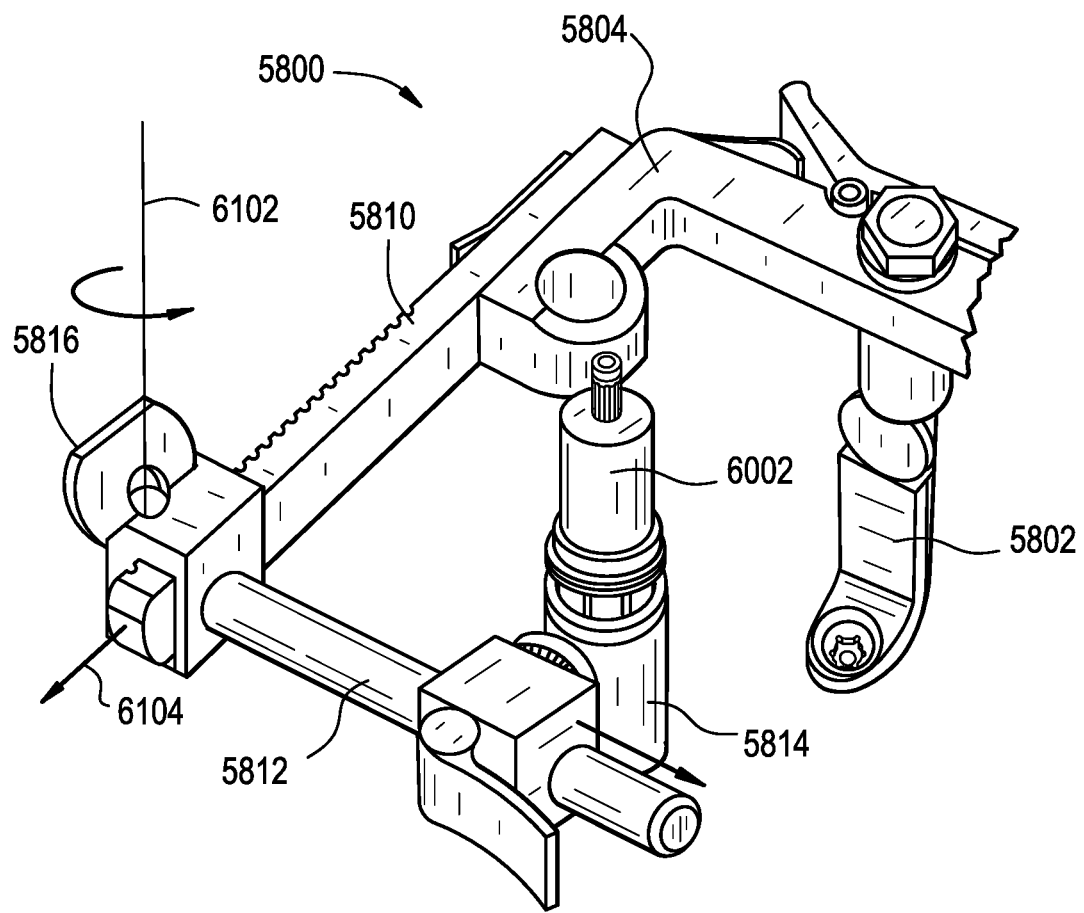
FIG. 61 is a detail view showing a third step in operating the surgical instrument assembly of FIG. 58.

An exemplary method of using the assembly 5800 for distraction is illustrated in FIGS. 59-61. As shown in FIG. 59, the method can include coupling the distraction rack 5810, post 5812, and receiver 5814 to the scaffold base 5804 that is coupled to a support instrument 5802. The support instrument 5802 can be coupled to an implantable anchor, such as a pedicle screw implanted in a patient's first vertebra. The support instrument can be locked to the anchor such that there is no relative movement between these two components. Similarly, the base 5804 can be locked against movement relative to the support instrument 5802. Further, the receiver 5814 can be positioned and locked against movement such that it is aligned with a second implantable anchor implanted in an adjacent vertebra of the patient.

FIG. 60 illustrates insertion of a shank extension instrument 6002 through the receiver 5814 to engage and lock on to the second implantable anchor. Once all components are locked to create a rigid construct, the actuator 5816 can be rotated in the direction of arrow 6102 to advance the post 5812 and receiver 5814 along the distraction rack 5810 in the direction of arrow 6104. Because the construct is locked against movement relative to each of the implanted anchors, movement of the post 5812 and receiver 5814 can cause corresponding movement of the shank extension 6002 and second implanted anchor, thereby distracting the adjacent vertebra and urging them away from one another.

FIGS. 62A-72 illustrate still other embodiments wherein tissue manipulating implements are coupled to polyaxial receiver heads that are coupled to implantable anchors. In such embodiments, the above described support instruments and tissue retractor assemblies can be eliminated, as tissue retraction can be accomplished using the tissue manipulating implements coupled directly to polyaxial receiver heads. Indeed, embodiments of receiver heads often include extension tabs to aid in various procedures that are broken off or otherwise removed from the receiver heads prior to finishing a procedure. Such tabs could serve as a mounting location for tissue manipulating implements to perform tissue retraction.

Figure 62A:
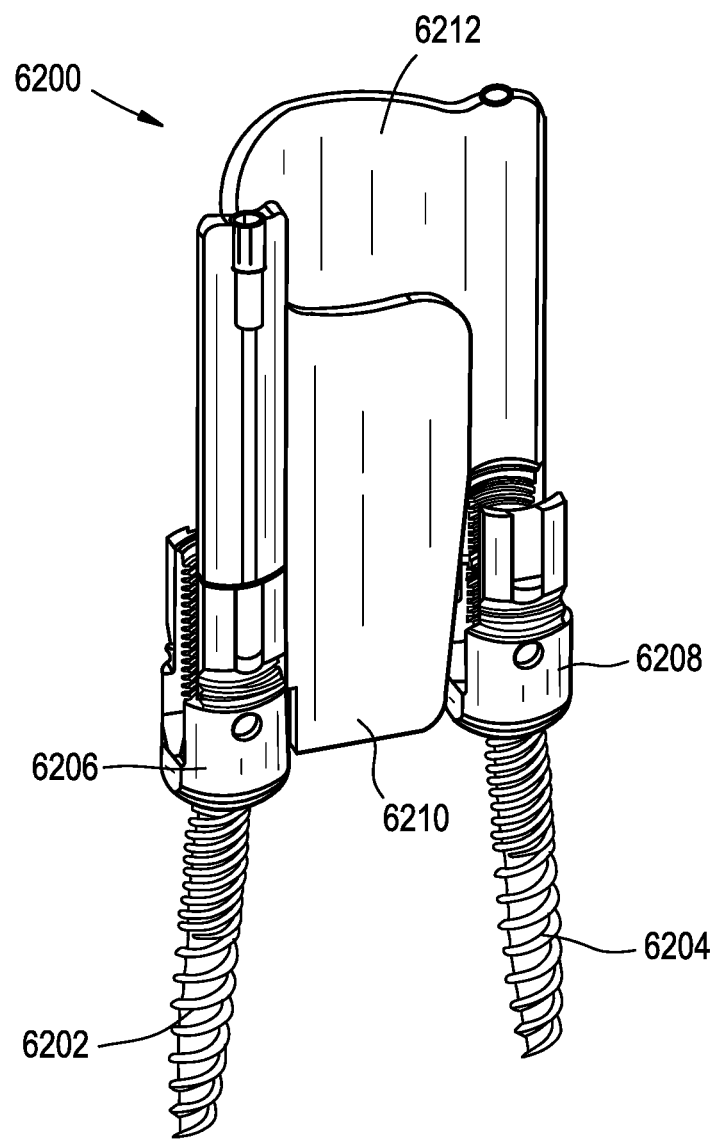
FIG. 62A is a side perspective view of one embodiment of a surgical instrument assembly including tissue manipulating implements coupled to polyaxial screw receiver heads.
Figure 62B:
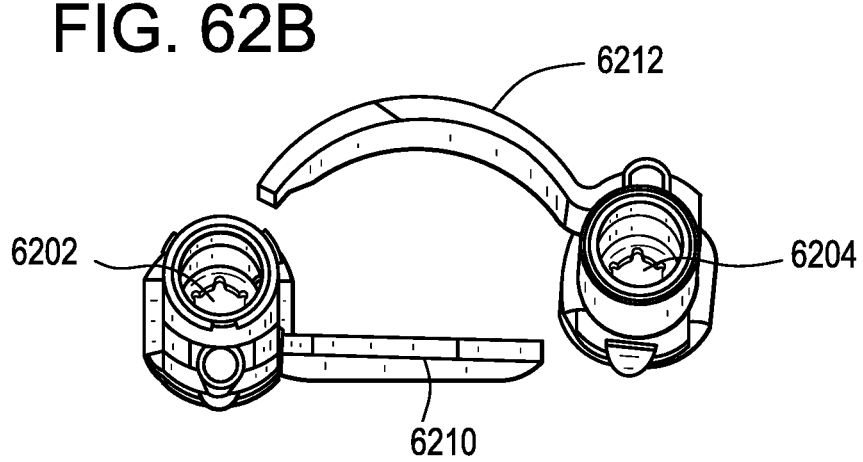
FIG. 62B is a top view of the assembly of FIG. 62A including anchor extensions coupled to the polyaxial screws.

FIGS. 62A and 62B illustrate one embodiment of an assembly 6200 that can include a first anchor 6202 and a second anchor 6204 that each can be coupled to a polyaxial receiver head 6206, 6208. Further, a first tissue manipulating implement 6210 can be coupled to the receiver head 6206 and a second tissue manipulating implement 6212 can be coupled to the receiver head 6208. The tissue manipulating implements can be arranged in a variety of manners but, in one embodiment in which the anchors 6202, 6204 are implanted along or parallel to a patient's spine or midline axis, the implement 6210 can be configured to perform lateral tissue retraction and the implement 6212 can be configured to perform medial tissue retraction.

Figure 63:
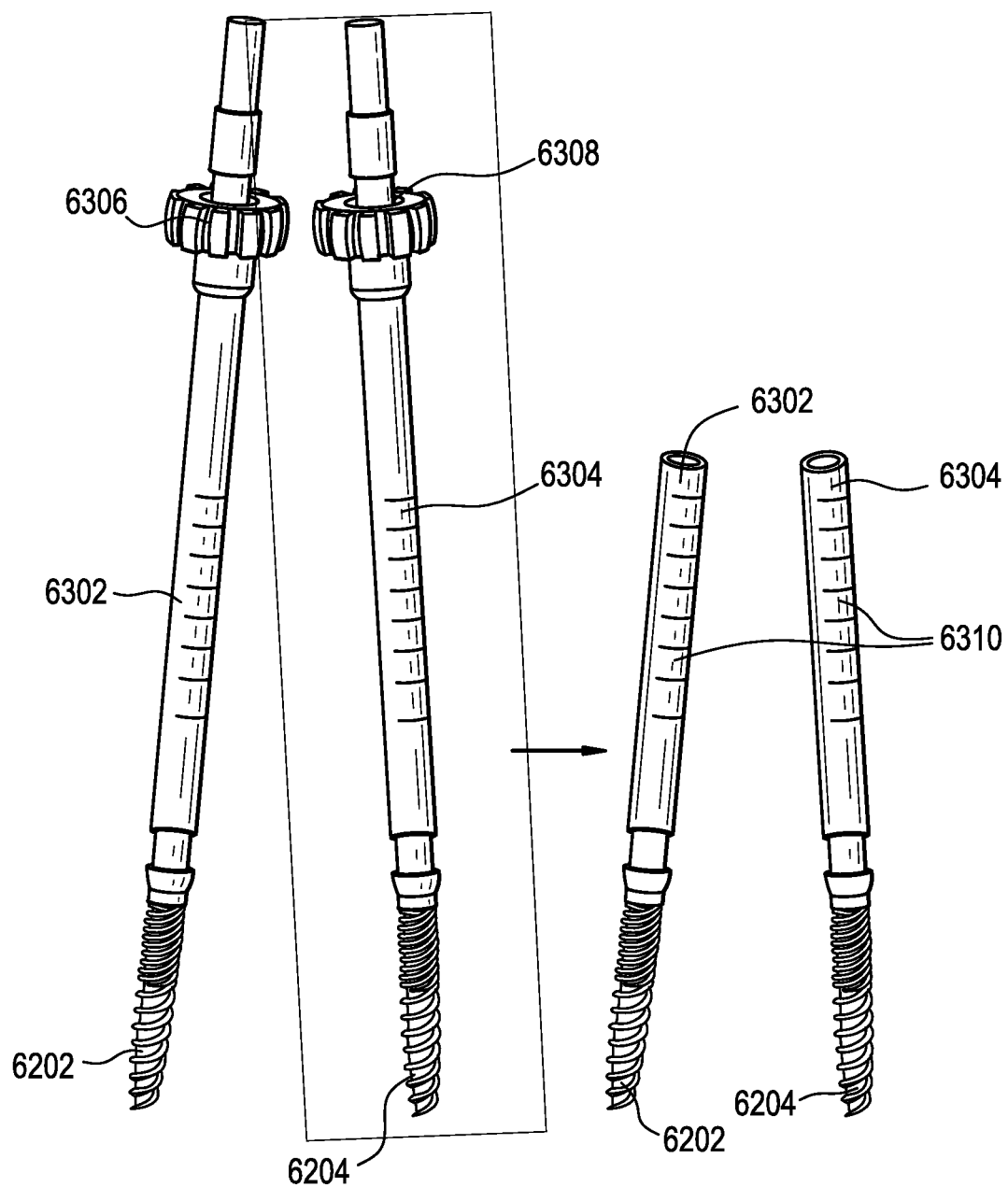
FIG. 63 is a side perspective view of one embodiment of a method for implanting anchors in a patient's bone.

An exemplary method for using the assembly 6200 described above is illustrated in FIGS. 63-72. As shown in FIG. 63, for example, the anchors 6202, 6204 can be implanted in a patient's vertebrae using extension tubes 6302, 6304 and drivers 6306, 6308. Following implantation, the drivers 6306, 6308 can be removed. Further, markings 6310 formed on the extensions 6302, 6304 can be utilized to measure a depth of tissue from the one surface that require retraction to facilitate further operations.

Figure 64:
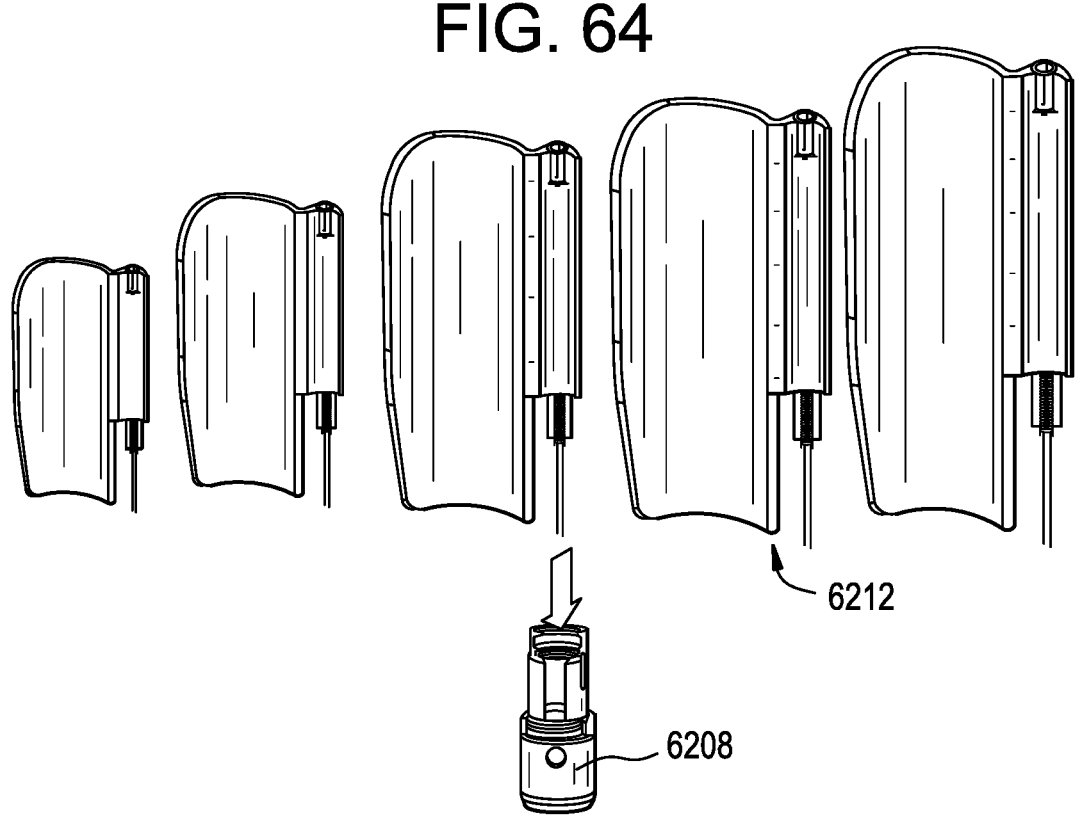
FIG. 64 is a side perspective view of a plurality of interchangeable tissue manipulating implements that can couple to a polyaxial screw receiver head.
Figure 65:
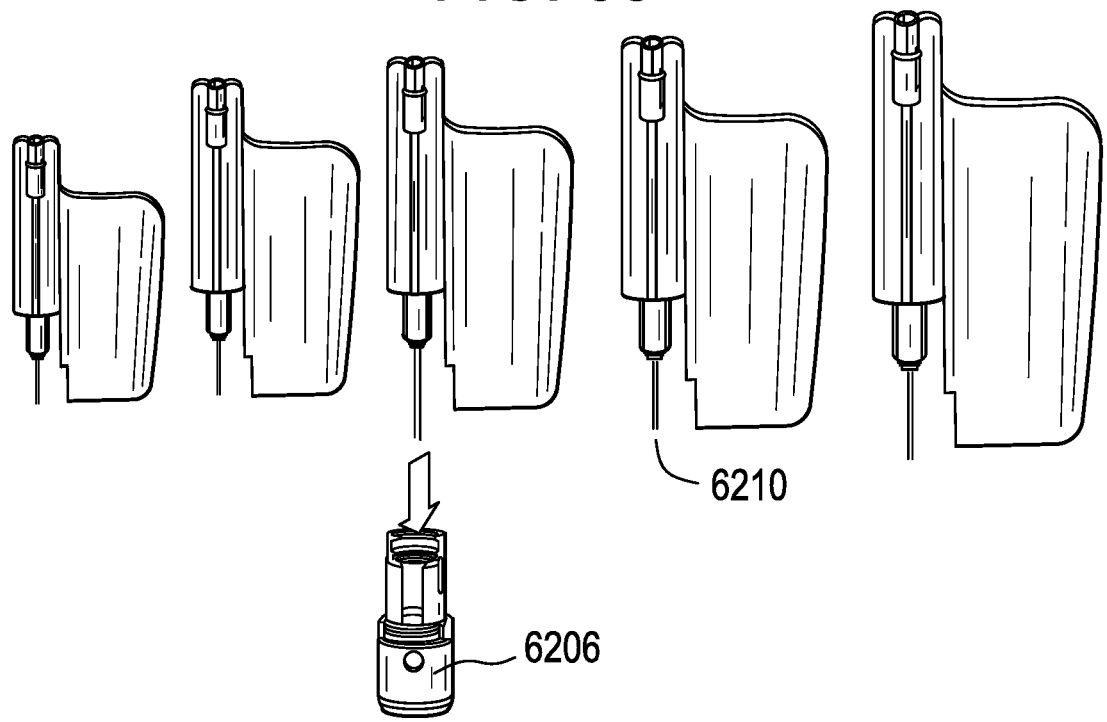
FIG. 65 is an alternative, opposite side perspective view of the tissue manipulating implements and polyaxial screw receiver head of FIG. 64.

Appropriately sized tissue manipulating implements 6210 and 6212 can be selected for each of the receiver heads 6206, 6208, as shown in FIGS. 64 and 65. As noted above, any of a variety of sizes and shapes of tissue manipulation implements can be interchanged as desired based on factors such as depth of tissue, type of tissue, etc. After selecting appropriate tissue manipulation implements 6210, 6212, the implements can be coupled to the receiver heads 6206, 6208 that are to be coupled to the implanted anchors 6202, 6204. For example, a first tissue manipulation implement 6210 can be coupled to an extension tab 6704 of a receiver head 6206 using a locking screw 6702 and a second tissue manipulation implement 6212 can be coupled to an extension tab 6606 of a receiver head 6208 by turning a locking screw 6602 in the direction of arrow 6604, as shown in FIGS. 66 and 67.

Figure 68:
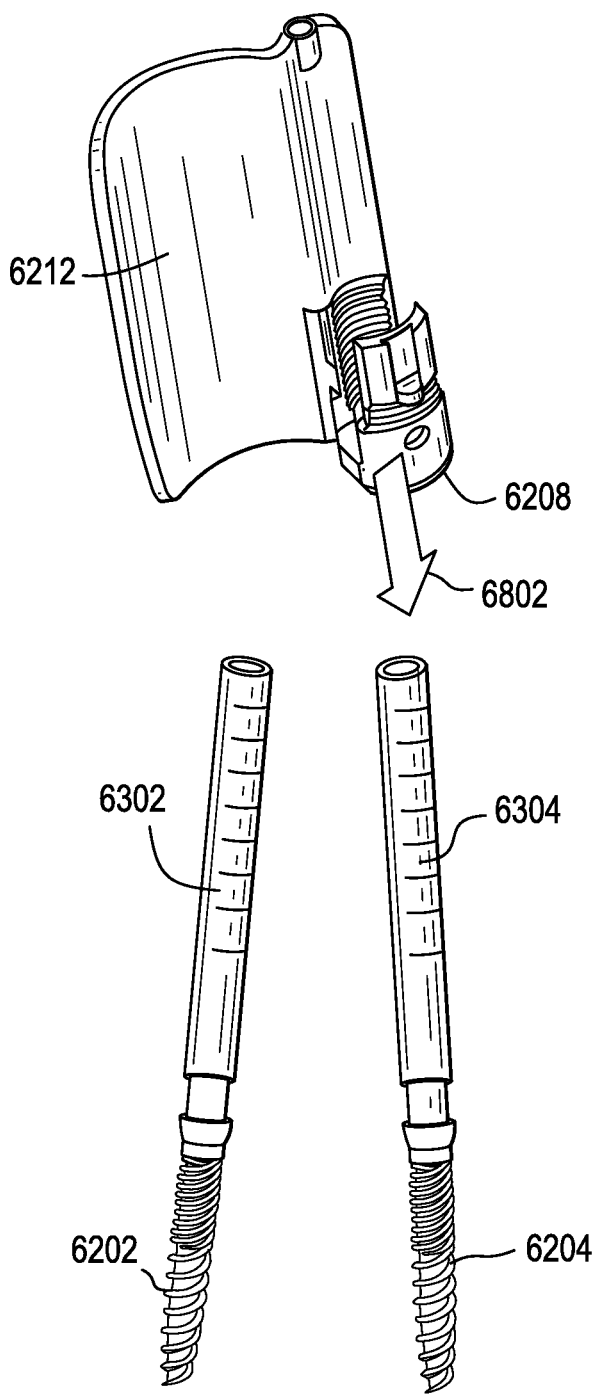
FIG. 68 is a side perspective view of one embodiment of a method for coupling a first tissue manipulating implement and first receiver head to an implanted anchor.
Figure 69:
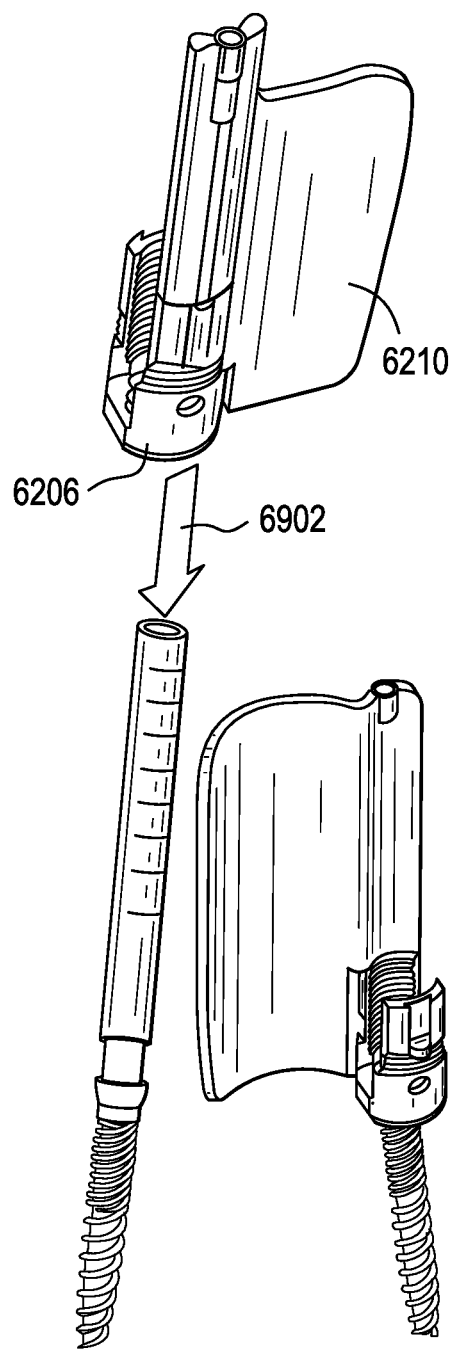
FIG. 69 is a side perspective view of one embodiment of a method for coupling a second tissue manipulating implement and second receiver head to an implanted anchor.
Figure 70:
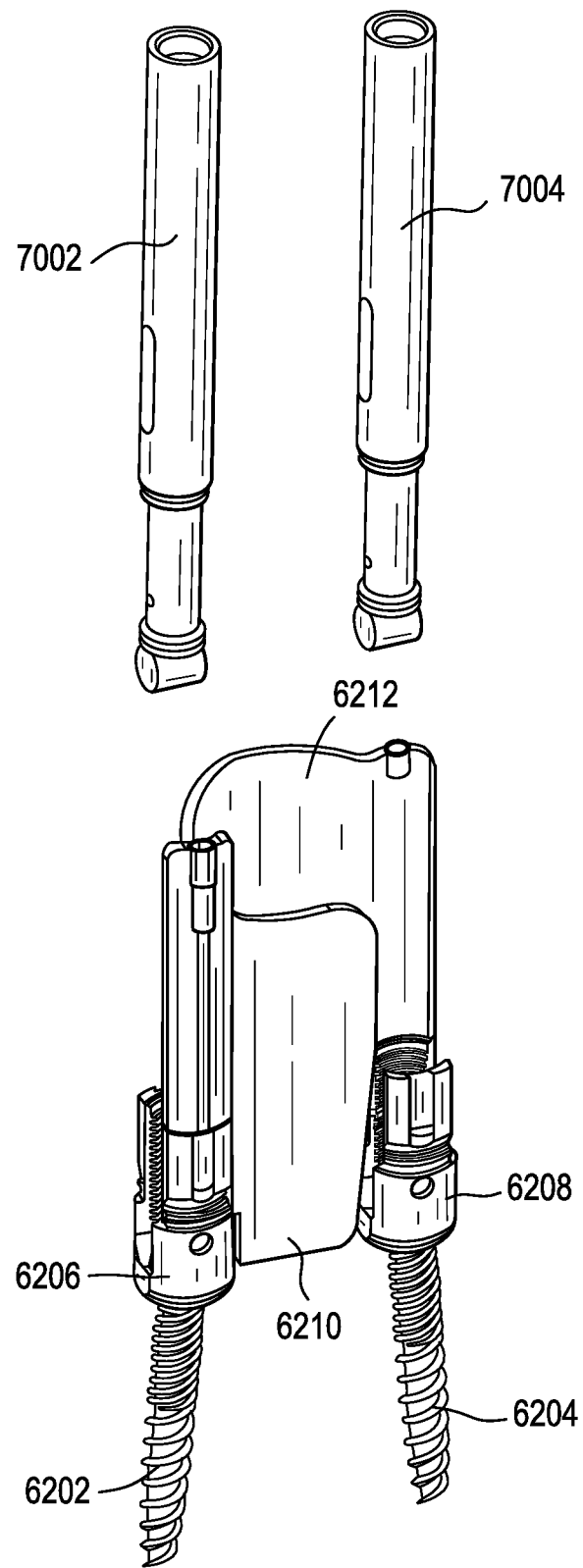
FIG. 70 is a side perspective view of one embodiment of a method for interfacing the receiver heads with polyaxial lockout posts.
Figure 71A:
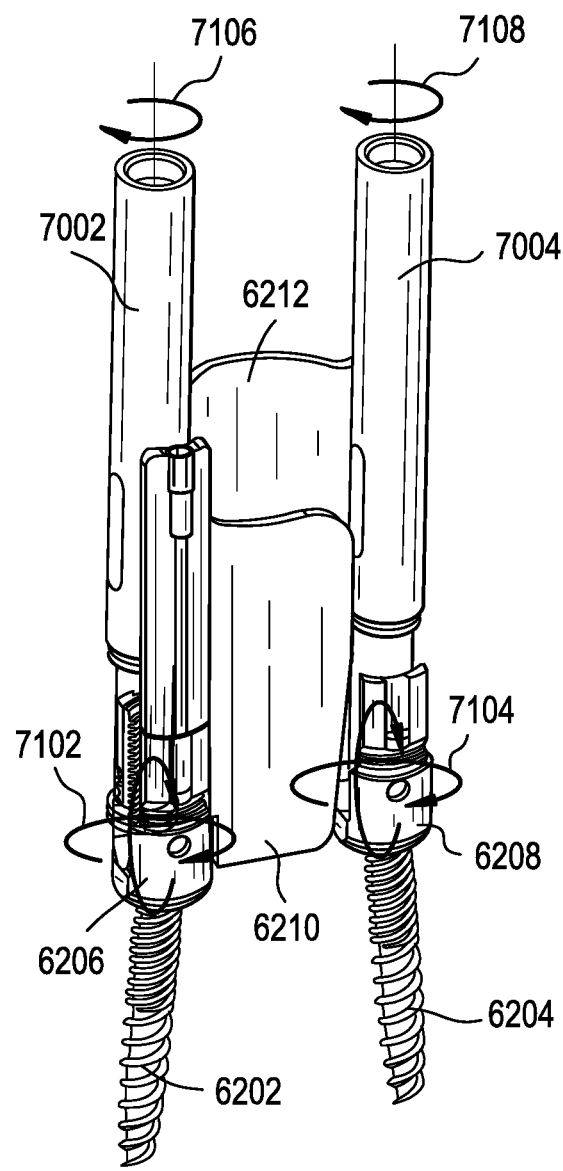
FIG. 71A is a side perspective view of various degrees of freedom of the polyaxial receiver heads and tissue manipulating implements.
Figure 71B:
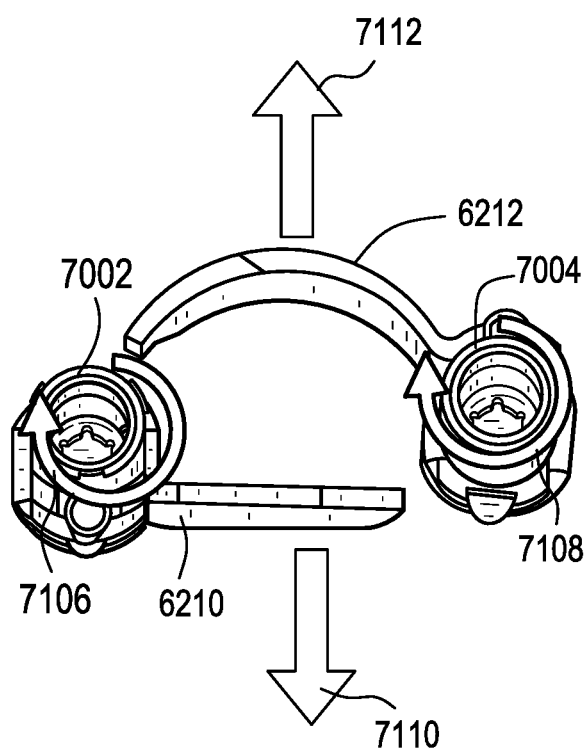
FIG. 71B is an alternative top view of various degrees of freedom of the polyaxial receiver heads and tissue manipulating implements.

The receiver heads 6206, 6208 with tissue manipulating implements 6210, 6212 coupled thereto can then be coupled to the implanted anchors 6202, 6204 and the extension posts 6302, 6304 can be removed, as shown in FIGS. 68 and 69. Polyaxial lockout posts 7002, 7004 can then be inserted as shown in FIG. 70 to provide levers for manipulating the orientation of the receiver heads 6206, 6208 and tissue manipulating implements 6210, 6212 coupled thereto. For example, a user can grasp the lockout posts 7002, 7004 to move the receiver heads 6206, 6208 and tissue manipulation implements 6210, 6212 polyaxially relative to the implanted anchors 6202, 6204, as shown by arrows 7102, 7104 in FIG. 71A. Such movement can also include moving lateral and medial tissue manipulation implements 6210, 6212 away from one another to perform medial-lateral tissue retraction, as shown by arrows 7110, 7112 in FIG. 71B. When a desired position is reached (e.g., including desired tissue retraction), the lockout posts 7002, 7004 can be rotated in the direction of arrows 7106, 7108 in FIGS. 71A and 71B to lock the receiver heads 6206, 6208 and tissue manipulation implements coupled thereto against movement relative to the implanted anchors 6202, 6204.

Figure 72:
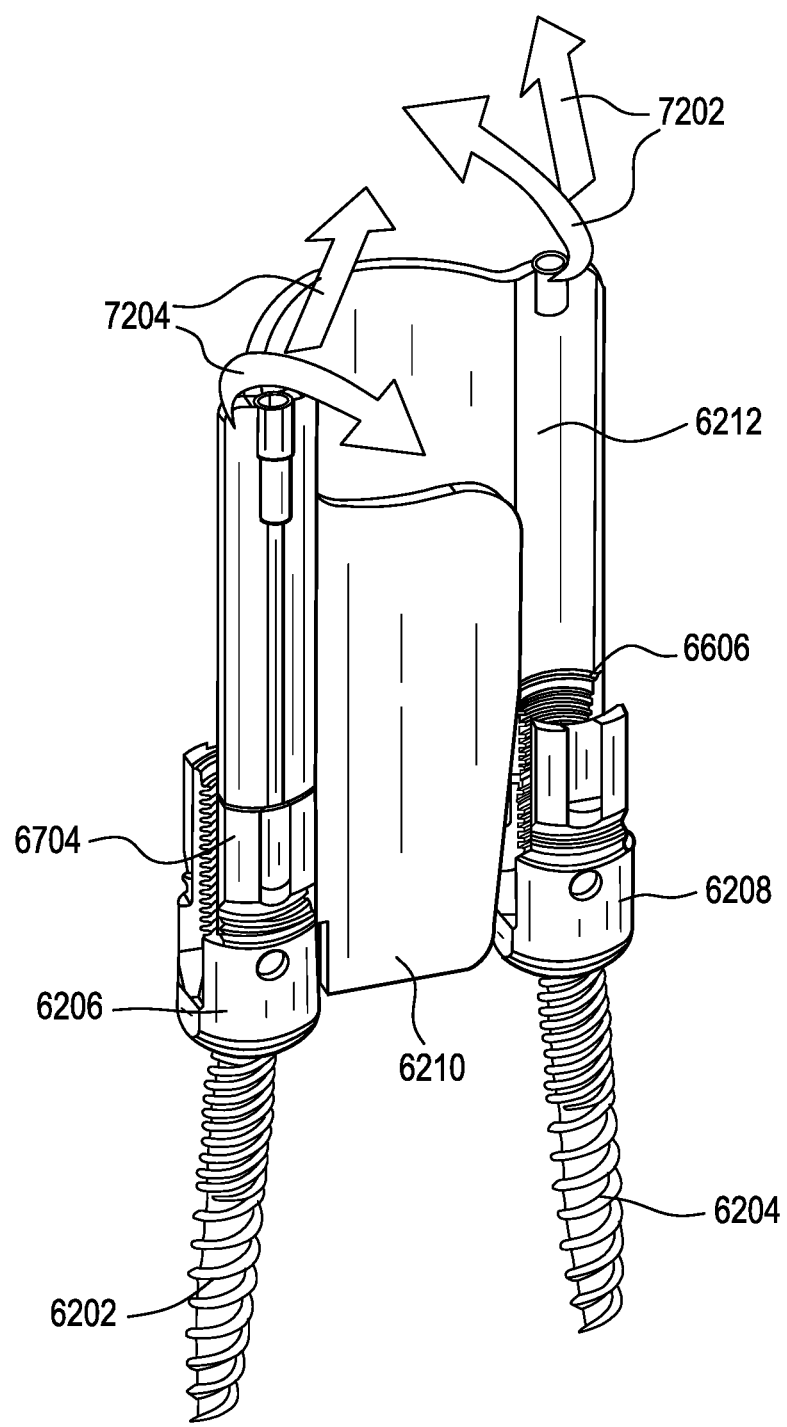
FIG. 72 is a side perspective view of one embodiment of a method for removing tissue manipulating implements after use.

Following completion of a spinal procedure, extension tabs of polyaxial screw receiver heads are often broken off or otherwise removed to leave a lower profile implant in the patient. As shown in FIG. 72, in some embodiments the tissue manipulation implements 6210, 6212 coupled to the extension tabs 6606, 6704 can be utilized to break the extension tabs free from the receiver heads 6206, 6208. For example, a proximal portion of the tissue manipulation implements 6210, 6212 can be grasped and bent in the direction of arrows 7202, 7204 to break the tissue manipulation implements and extension tabs coupled thereto away from the receiver heads.

Figure 73:
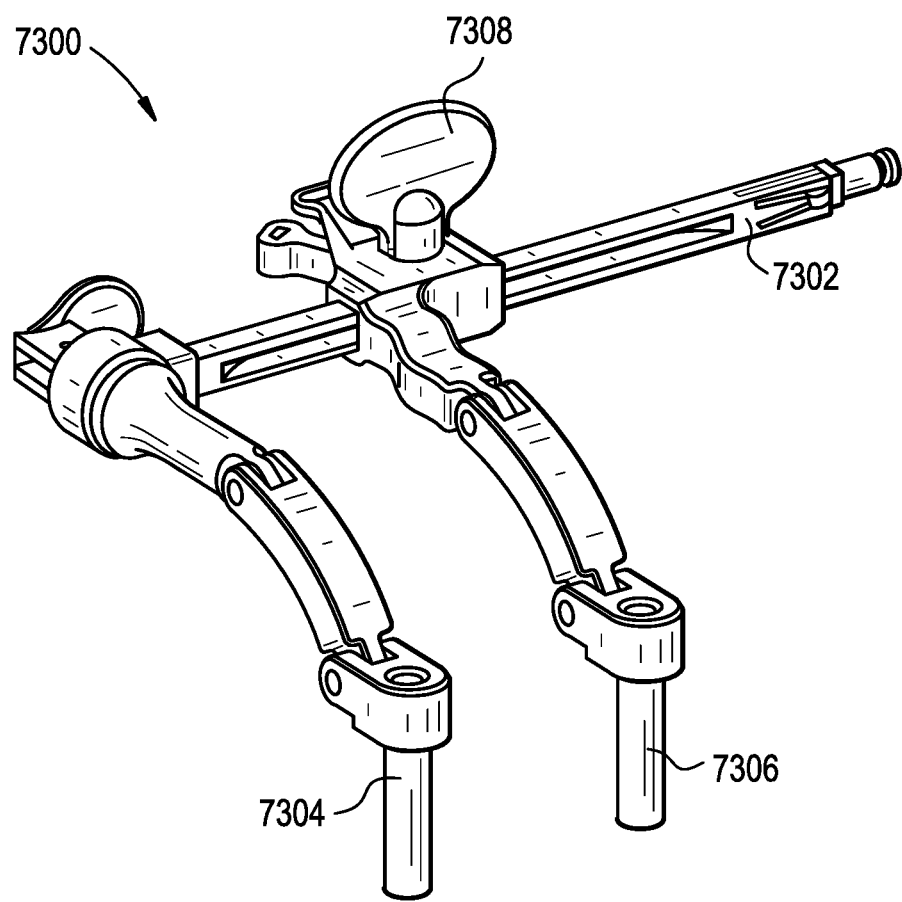
FIG. 73 is a side perspective view of one embodiment of a spinal distraction instrument according to the teachings provided herein.

FIGS. 73-78B illustrate various embodiments of instruments for distracting adjacent vertebrae and their use with the support instruments and retractor assemblies described herein. For example, FIG. 73 illustrates one embodiment of a distractor 7300 that includes a rack 7302 and two interfaces 7304, 7306 for coupling with any of an anchor or an instrument coupled to an anchor. The interface 7304 can be anchored to one end of the rack 7302 and the interface 7306 can be coupled to the rack 7302 via a pawl, cog, gear, or other feature that can interface with a series of teeth, recesses, or other features formed along a length of the rack. A thumbwheel 7308 can be coupled to the cog or gear to control movement of the interface 7306 along the rack 7302.

Figure 74A:
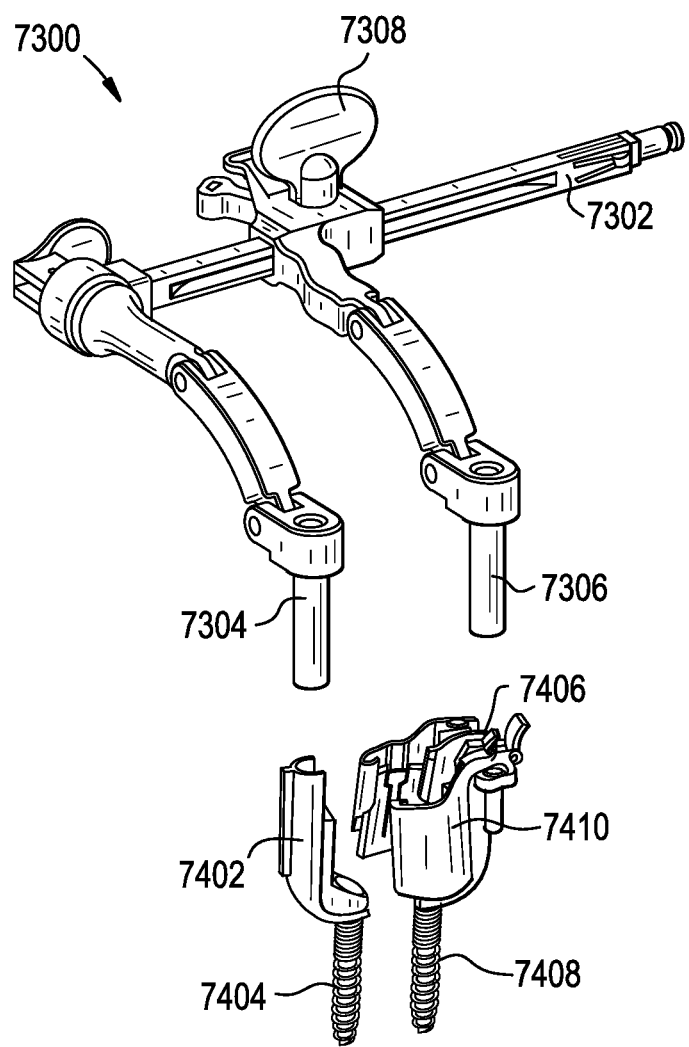
FIG. 74A is a side perspective view of the distraction instrument of FIG. 73 coupling with other surgical instruments described herein.
Figure 74B:
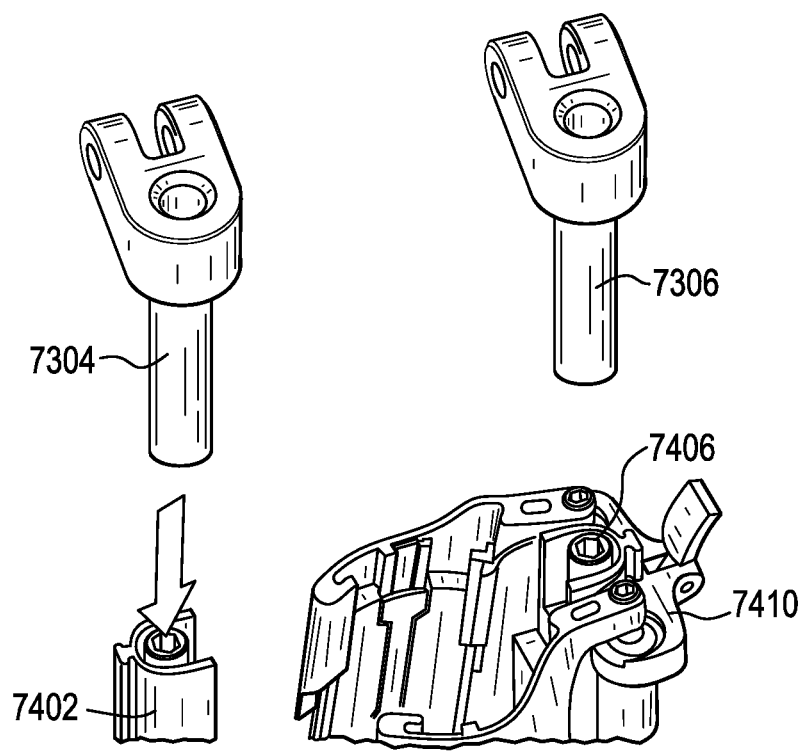
FIG. 74B is a detail view of distal ends of the distraction instrument of FIG. 73 approaching the other surgical instruments shown in FIG. 74A.
Figure 75:
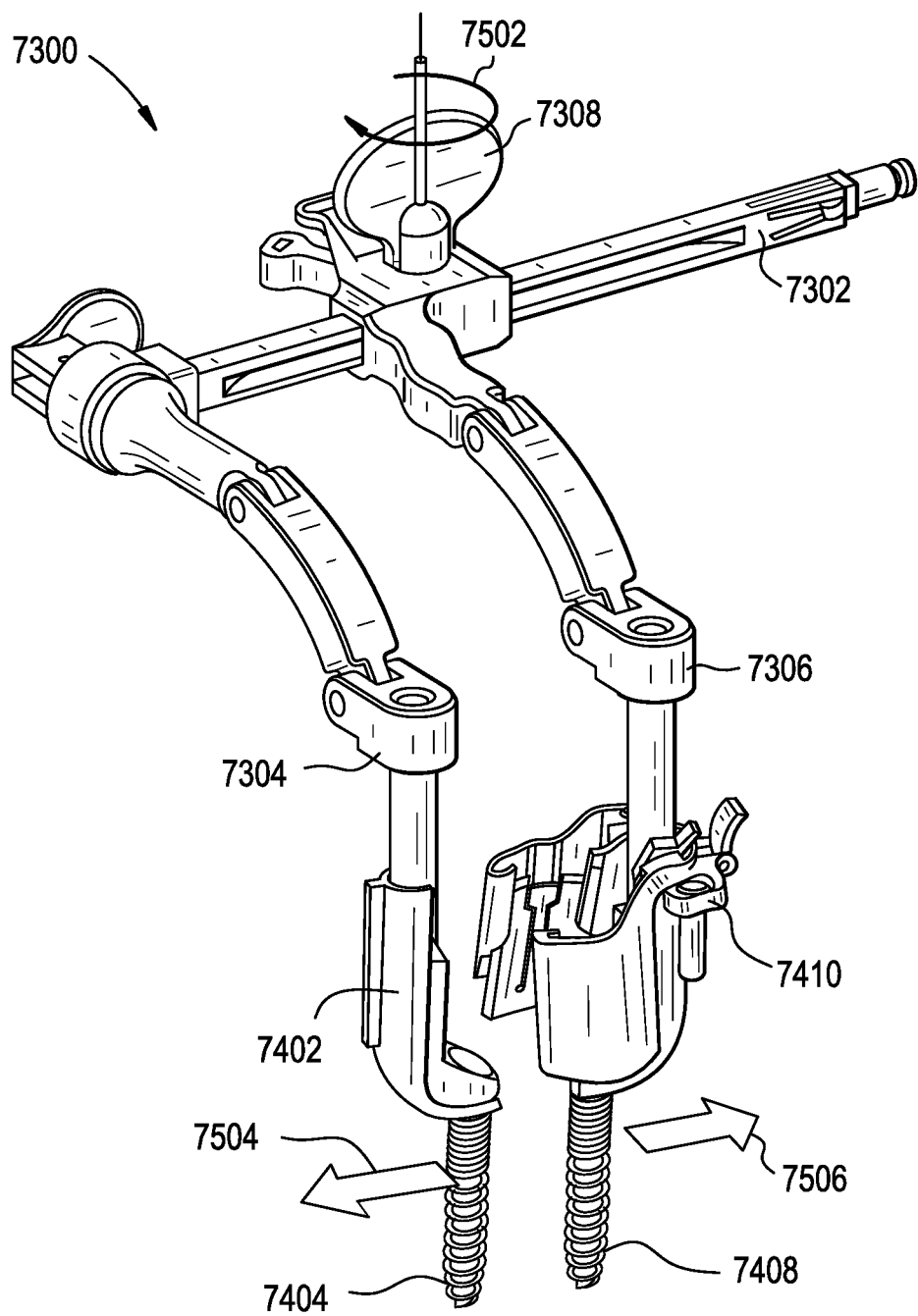
FIG. 75 is a side perspective view of the spinal distraction instrument of FIG. 73 applying a distraction force to the other surgical instruments shown in FIG. 74A.
Figure 76:
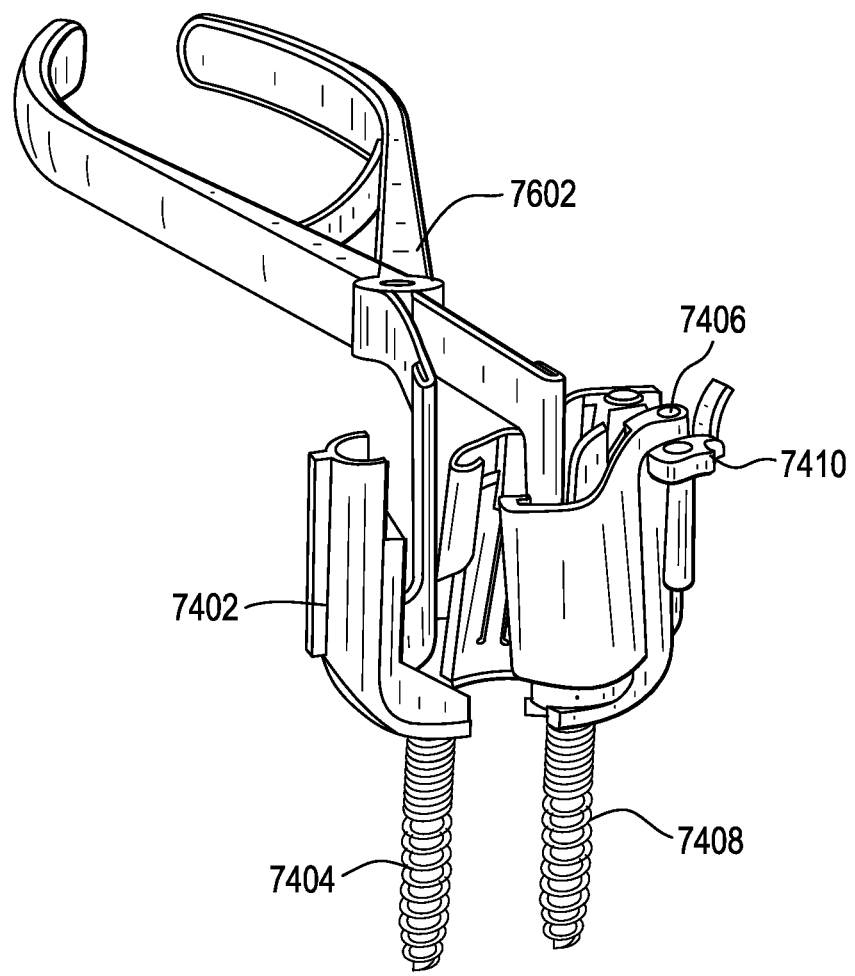
FIG. 76 is a side perspective view of another embodiment of a spinal distraction instrument according to the teachings provided herein.
Figure 77:
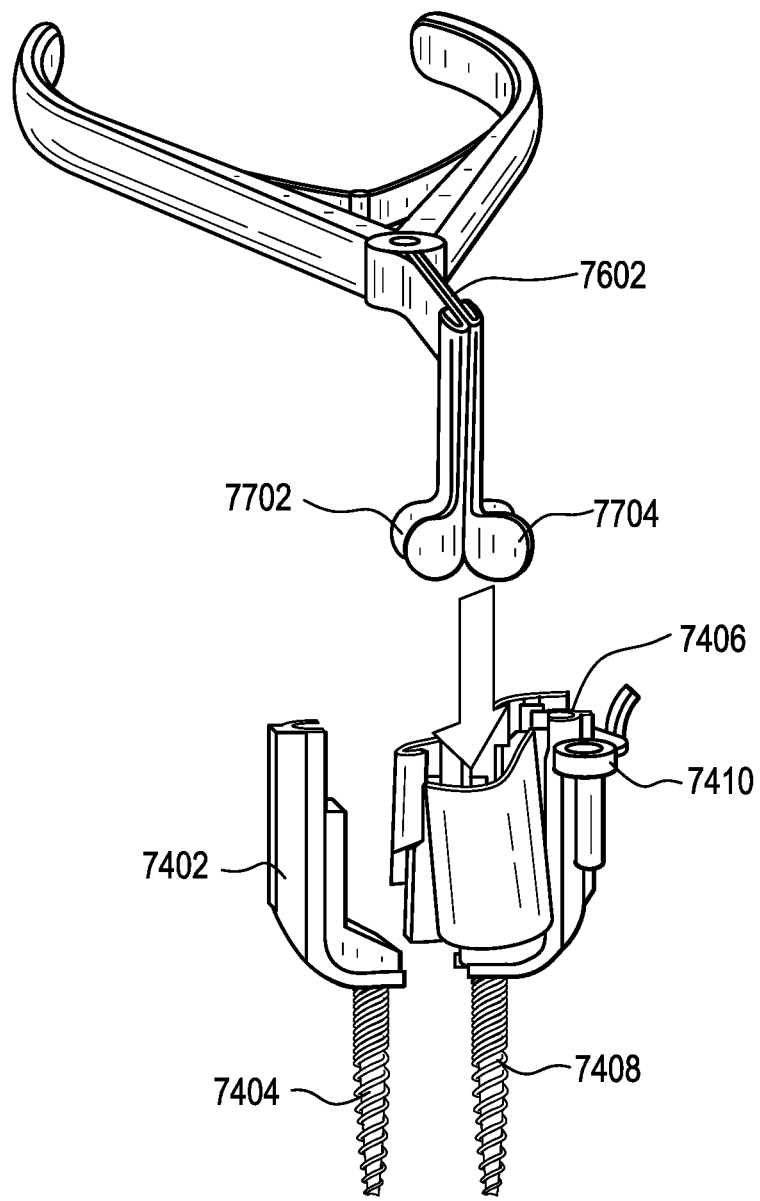
FIG. 77 is a side perspective view of the distraction instrument of FIG. 76 coupling with other surgical instruments described herein.
Figure 78A:
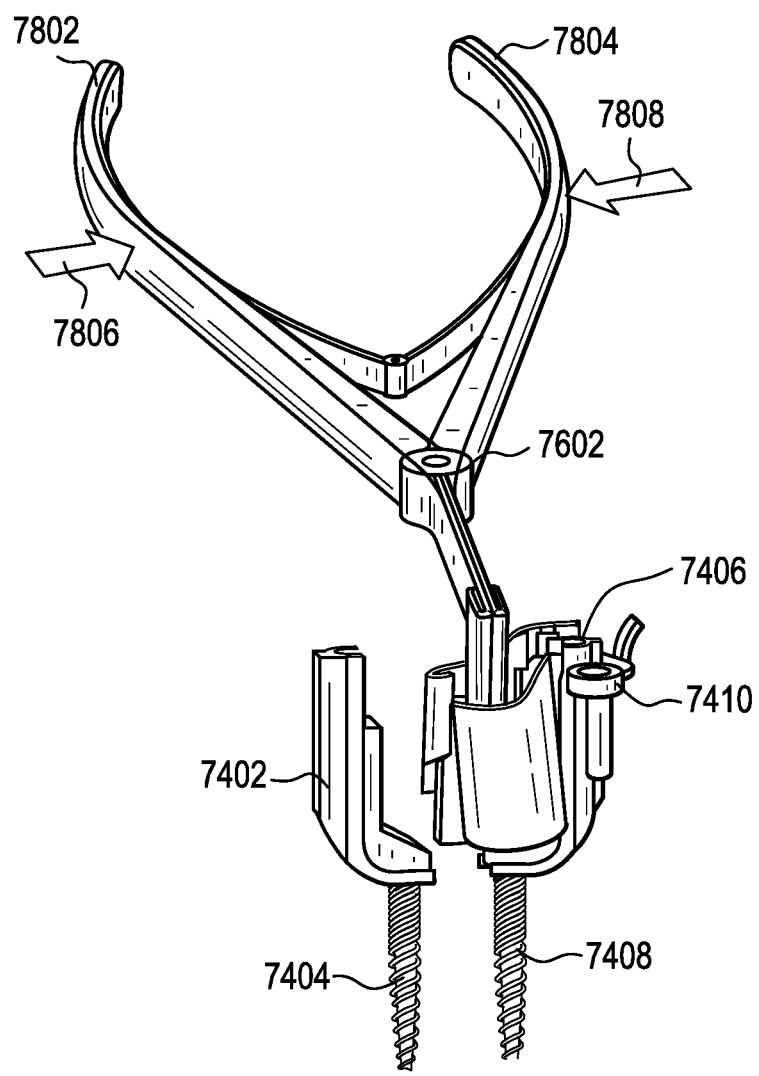
FIG. 78A is a side perspective view of the distraction instrument of FIG. 76 being actuated.
Figure 78B:
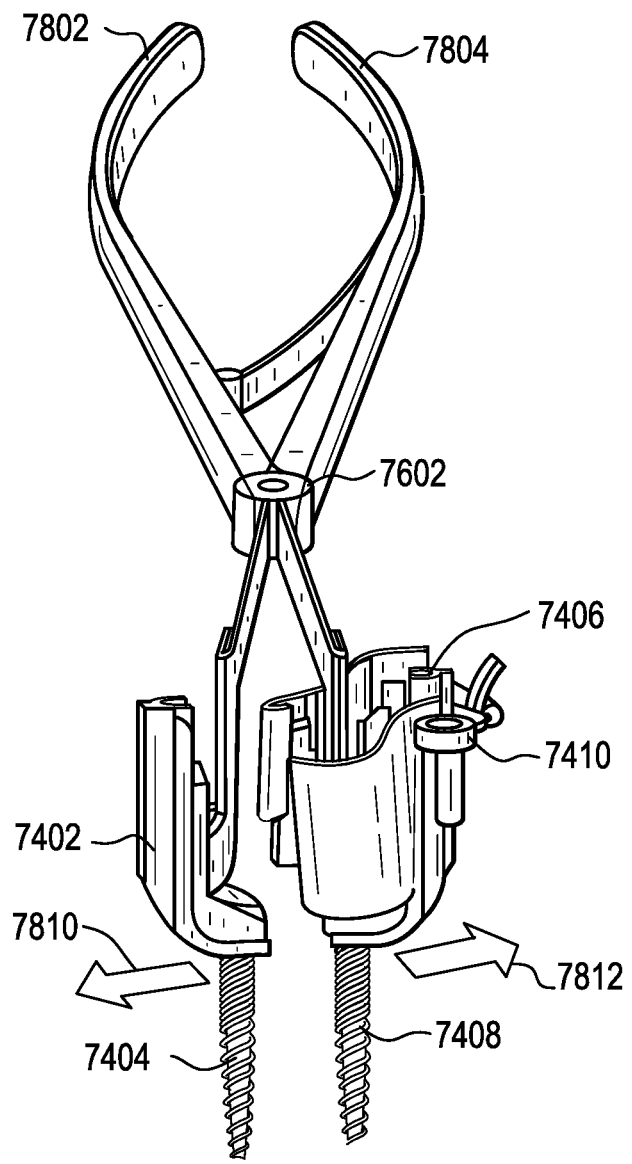
FIG. 78B is a side perspective view of the distraction instrument of FIG. 76 applying a distraction force to the other surgical instruments of FIG. 77.

As shown in FIGS. 74A-75, the interfaces 7304, 7306 can be coupled to anchors implanted in adjacent vertebrae and the thumbwheel 7308 can be rotated to distract the vertebrae by moving the interfaces away from one another along the rack 7302. In the illustrated embodiment, the interfaces can couple to the anchors implanted in the adjacent vertebrae via an extension tower and/or support instrument as described herein that can be coupled to the implanted anchors and locked against movement relative thereto. Accordingly, as shown in FIGS. 74B and 75, the interface 7304 can couple to a proximal end of an extension tower 7402 that is coupled to an anchor 7404 implanted in a first vertebra and the interface 7306 can couple to a proximal end of a support instrument 7406 that is coupled to a second anchor 7408 implanted in a second vertebra. As shown in FIG. 74B, the interfaces 7304, 7306 can include distal ends configured to couple with features formed on proximal ends of the extension tower 7402 and support instrument 7406. Also note that a retractor assembly 7410 is coupled to the support instrument 7406 to provide, e.g., medial-lateral tissue retraction during the procedure.

Once the distraction instrument 7300 is coupled to the anchors 7404, 7408 implanted in adjacent vertebrae via the extension tower 7402 and support instrument 7406, and the tower and support instrument are locked against movement relative to the anchors, the thumbwheel 7308 or other distraction actuator can be rotated as shown by arrow 7502 in FIG. 75. This can cause the interface 7306 to move away from interface 7304 along the rack 7302, thereby causing corresponding distraction of the anchors 7404, 7408 and the adjacent vertebrae they are implanted into, as shown by arrows 7504, 7506.

In an alternative embodiment illustrated in FIGS. 76-78B, a forceps-like distractor 7602 can be utilized instead of the distractor 7300 described above. Furthermore, the distractor 7602 can include interfaces 7702, 7704 that can be configured to abut against the extension tower 7402 and support instrument 7406 laterally at a position along a length thereof, rather than interfacing with a proximal end thereof, as described above. The method of operation can be similar to that described above, wherein the extension tower 7402 and support instrument 7406 can be locked to prevent movement relative to the implanted anchors 7404, 7408. The interfaces 7702, 7704 can then be inserted into the working channel provided between the opposed tissue manipulating implements of the retractor assembly 7410 and opposed handles 7802, 7804 of the distractor 7602 can be urged toward one another, as shown by the arrows 7806, 7808 of FIG. 78A. This can cause the interfaces 7702, 7704 to move apart from one another, contact the tower 7402 and support instrument 7406, and urge the two components away from one another, as shown by arrows 7810, 7812 of FIG. 78B. Given the rigid implantation of the anchors 7404, 7408 in adjacent vertebrae (not shown), the vertebrae can be drawn away from one another in the same manner.

Figure 79:
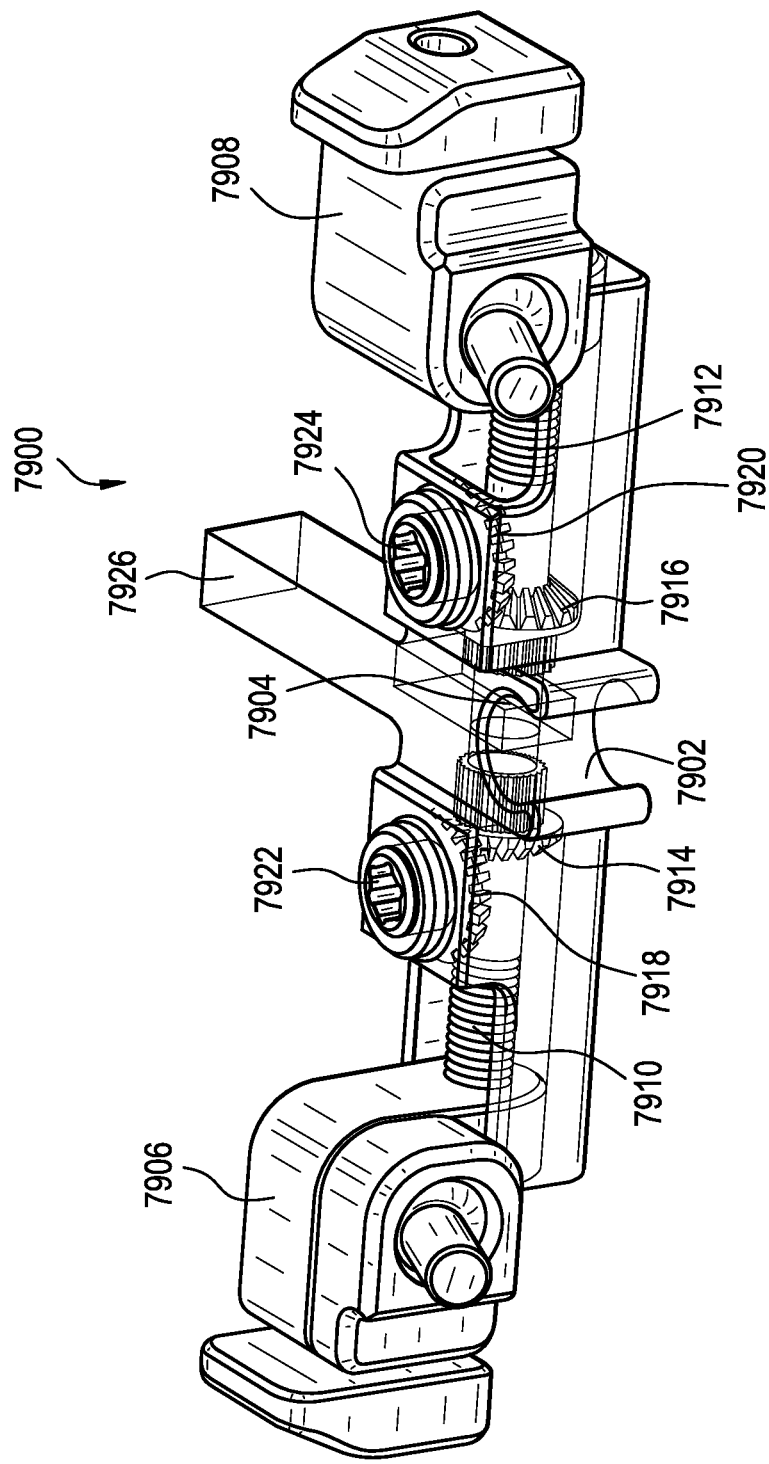
FIG. 79 is a partially transparent perspective view of another embodiment of a retractor.
Figure 80:
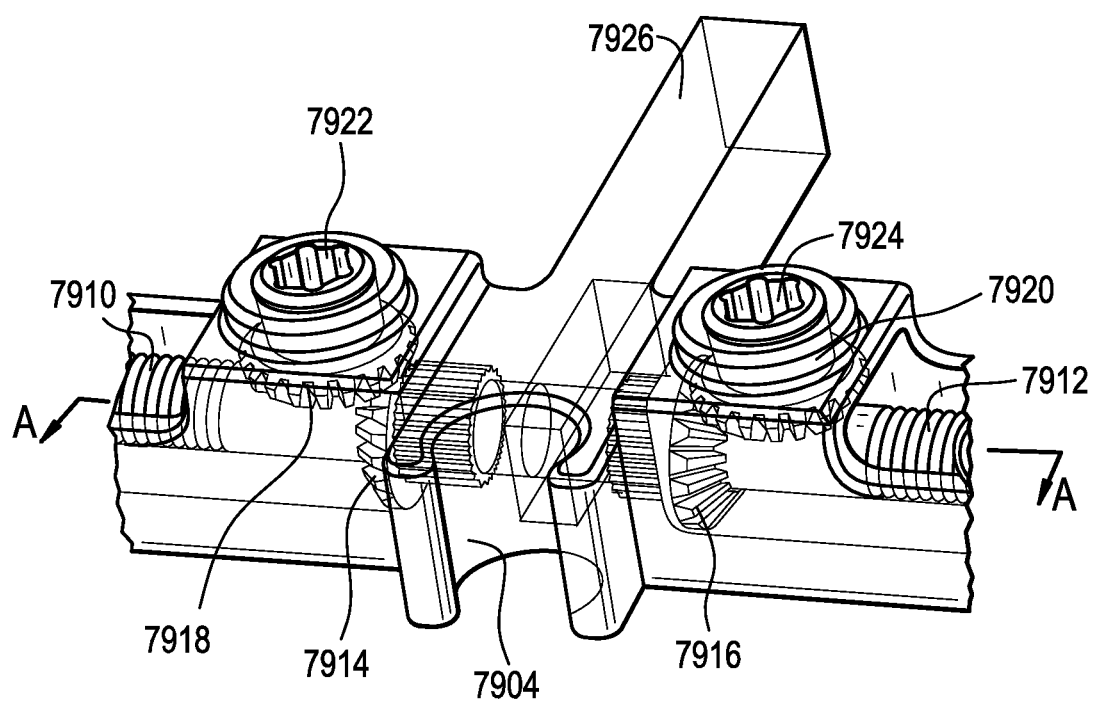
FIG. 80 is a partially transparent detail view of a portion of the retractor of FIG. 79.
Figure 81:
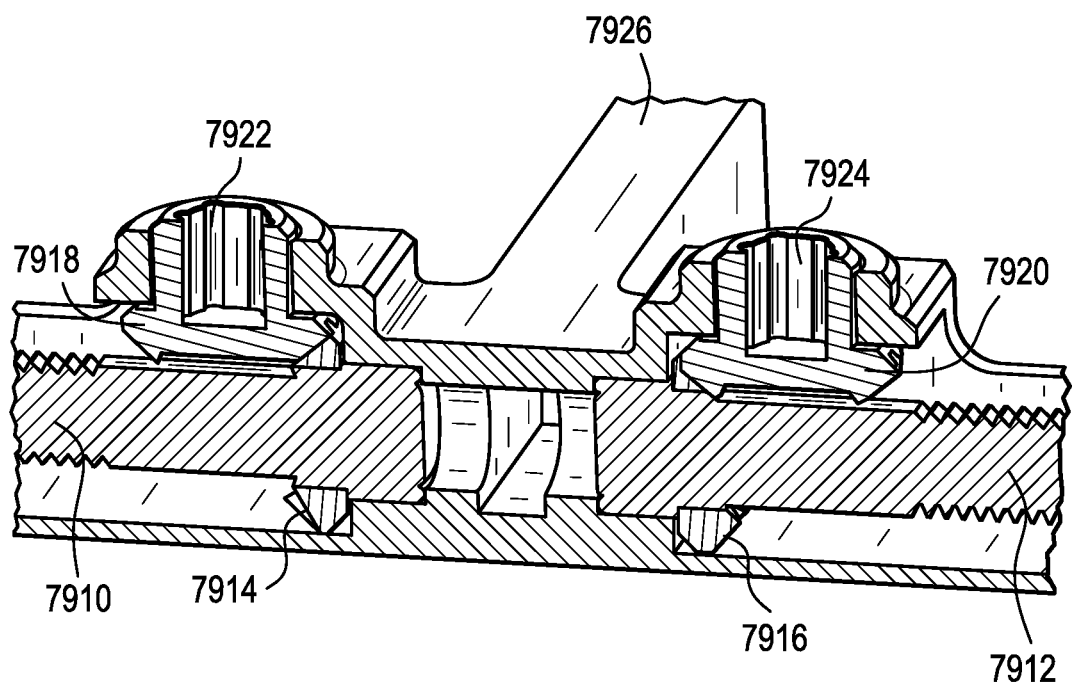
FIG. 81 is a cross-sectional view of the portion of the retractor shown in FIG. 80 taken along the line A-A in FIG. 80.

FIGS. 79-101E illustrate further embodiments of surgical instrument assemblies. For example, FIGS. 79-81 illustrate an embodiment of a surgical retractor 7900 that includes alternative mechanisms for controlling movement of retractor arms, and tissue manipulating implements coupled thereto. The retractor 7900 can be configured to couple to a support instrument, such as the instrument 102 described above, in a similar manner as the retractor 106 described above, e.g., using a recess 7902 and a spring-biased protrusion or pawl 7904. Rather than the fixed polyaxial joints 212, 214, however, the retractor 7900 can include polyaxial joints 7906, 7908 that are configured to translate toward or away from the recess 7902 using, e.g., a lead screw mechanism. In such a configuration, the joints 7906, 7908, as well as any tissue manipulating implements coupled thereto, can be moved toward or away from one another (e.g., medially or laterally relative to a patient) to increase or decrease a space between tissue manipulating implements.

In the illustrated embodiment, each joint 7906, 7908 is threadedly coupled to a respective rod 7910, 7912 such that rotation of the rod effects translation of the respective joint along a length of the rod. A gear 7914, 7916 disposed about each respective rod 7910, 7912 can interact with a drive gear 7918, 7920 that is coupled to or formed integrally with a drive feature 7922, 7924. A user can rotate the drive feature 7922, 7924 to cause translation of the respective joint 7906, 7908 along a length of the retractor body 7926. In the illustrated embodiment, positions of each joint 7906, 7908 can be controlled independently of one another using the two drive features 7922, 7924. The above-described joint translation mechanisms are shown in greater detail in the partially-transparent detail view of FIG. 80 and the cross-sectional detail view of FIG. 81.

Figure 82:
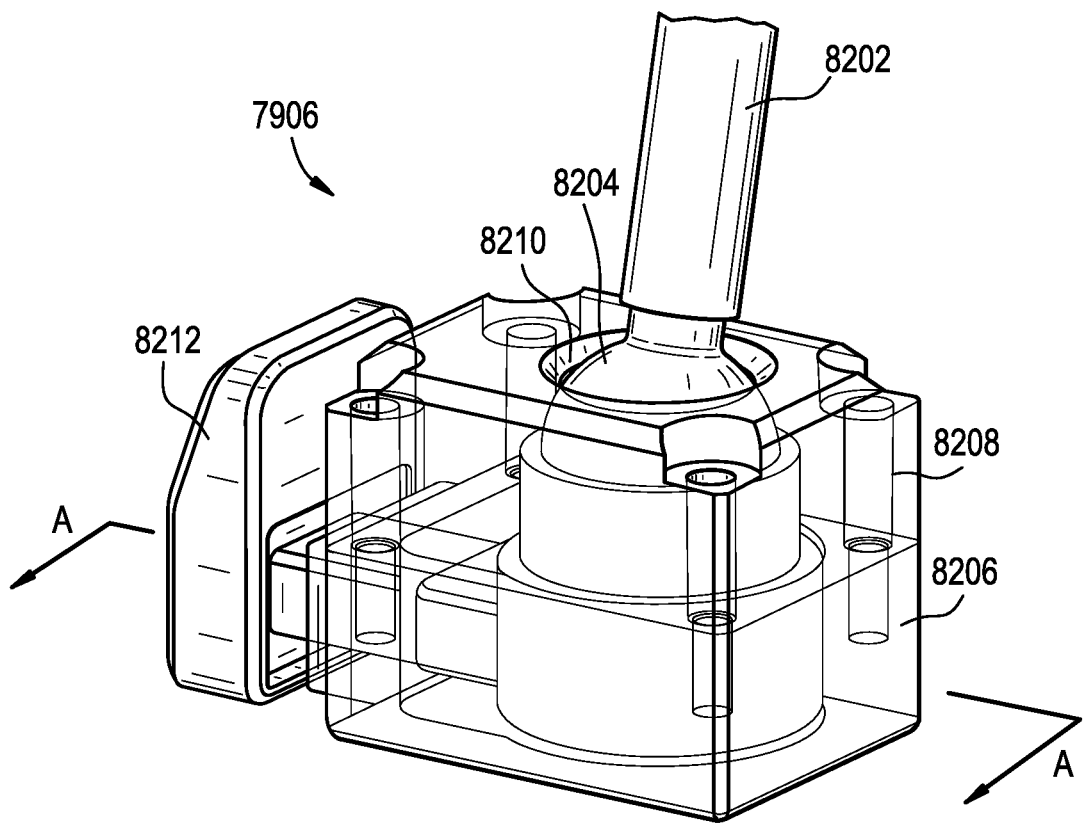
FIG. 82 is a partially transparent detail view of a polyaxial locking mechanism of the retractor of FIG. 79.

The joints 7906, 7908 of the retractor 7900 also include an alternative embodiment of a polyaxial movement mechanism. FIG. 82, for example, illustrates a partially transparent detail view of the joint 7906. The joint can include an arm 8202 having a ball 8204 (that can be incompressible) formed at one end thereof and an opposite end configured for attachment to a tissue manipulating implement (e.g., either directly or through another arm or other linkage). The ball 8204 can be captured between a base 8206 and a cap 8208 such that the ball cannot be removed or passed through a hole 8210 formed in the cap. The joint mechanism can be biased to lock the ball 8202 from moving relative to the base 8206 and cap 8208, and a release button 8212 can be configured to free the ball when depressed inward toward the base and cap. Such an arrangement can provide an advantage in that actuation of a single button or lever can control locking of the ball 8204 and arm 8202. Further, the button 8212 can be biased such that no actuation is needed to tighten or lock the ball and a single input from a user (e.g., inward depression of the button) can selectively free the ball for polyaxial movement.

Figure 83:
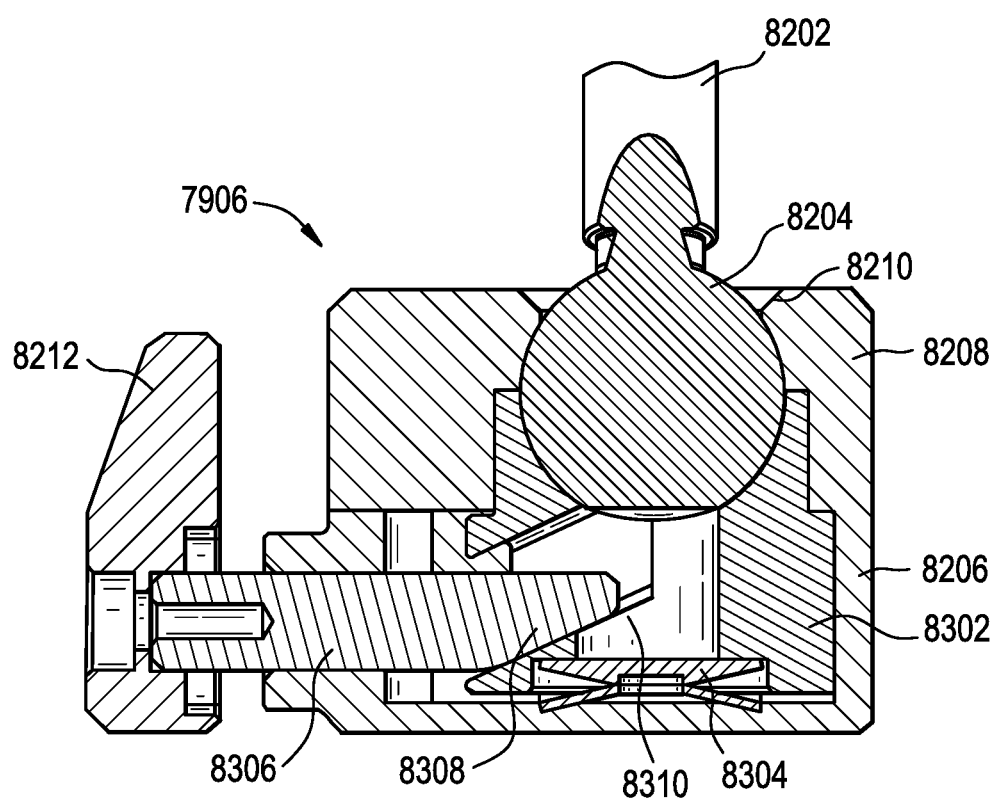
FIG. 83 is a cross-sectional view of the polyaxial locking mechanism of FIG. 82 taken along the line A-A in FIG. 82.

The cross-sectional view of FIG. 83 illustrates one embodiment of a mechanism for effecting the behavior of the button 8212 and joint 7906 described above. A compression member 8302 can be disposed within a recess formed by the base 8206 and cap 8208 and includes a surface that is complementary to the ball 8204. The compression member 8302 can be configured to translate up and down in the plane of the figure and can be biased upward in the plane of the figure by a biasing element 8304, such as a spring, Belleville washer, etc. The button 8212 can be coupled to a tongue 8306 having an angled end 8308 that engages a ramp 8310 formed on the compression member 8302. As the button 8212 is depressed into the base 8206 (i.e., to the right in the plane of the figure) the angled surfaces 8308, 8310 can interact to cause the compression member 8302 to move away from the ball 8204 (i.e., down in the plane of the figure), thereby freeing the ball to articulate relative to the compression member, cap, and base of the joint 7906. Upon release of the button 8212, the biasing element 8304 will urge the compression member 8302 toward the ball 8204, thereby locking its position relative thereto and causing the button 8212 to move outward from the base 8206 to its starting position.

Figure 84:
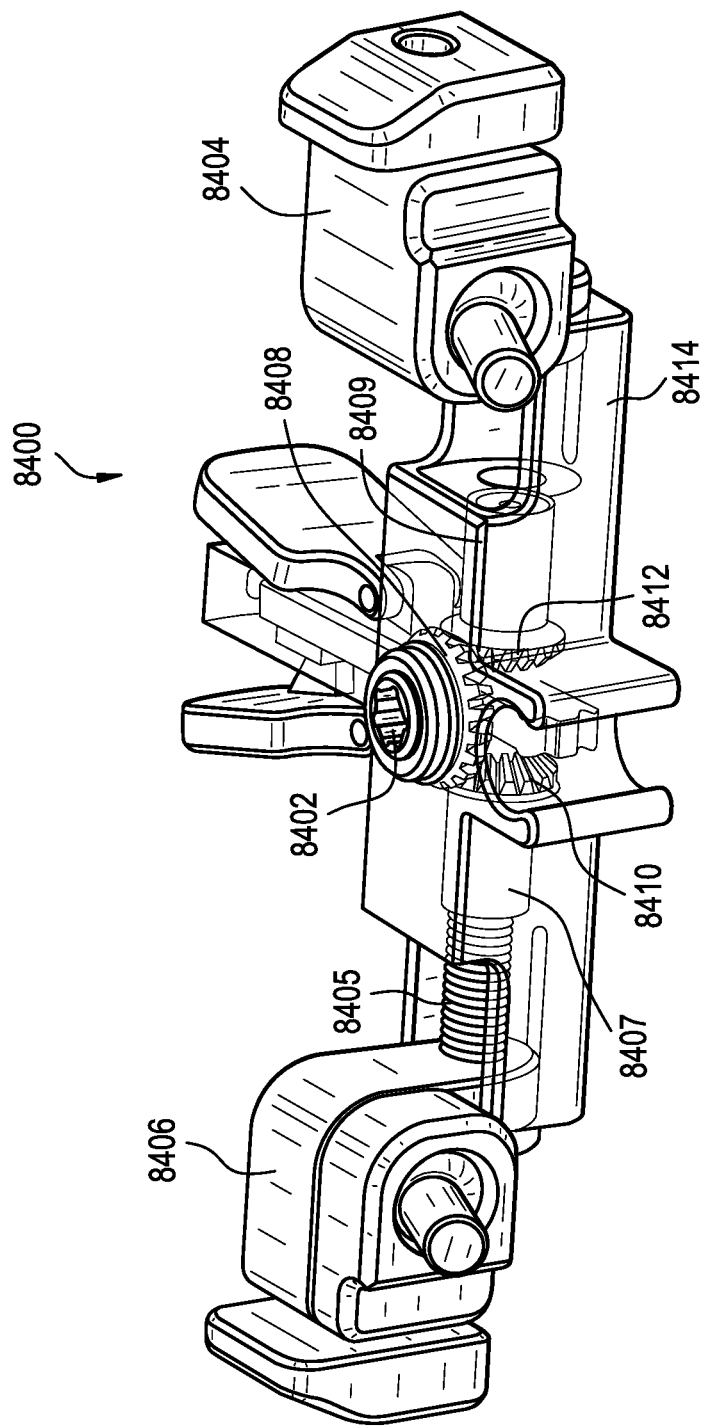
FIG. 84 is a partially transparent perspective view of another embodiment of a retractor.
Figure 85:
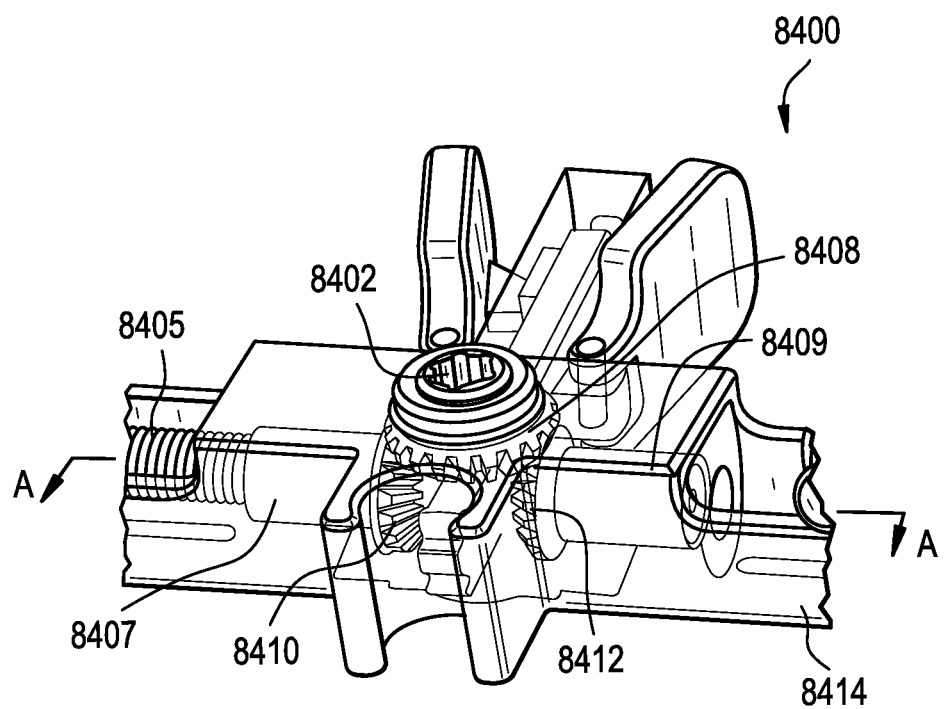
FIG. 85 is a partially transparent detail view of a portion of the retractor of FIG. 84.
Figure 86:
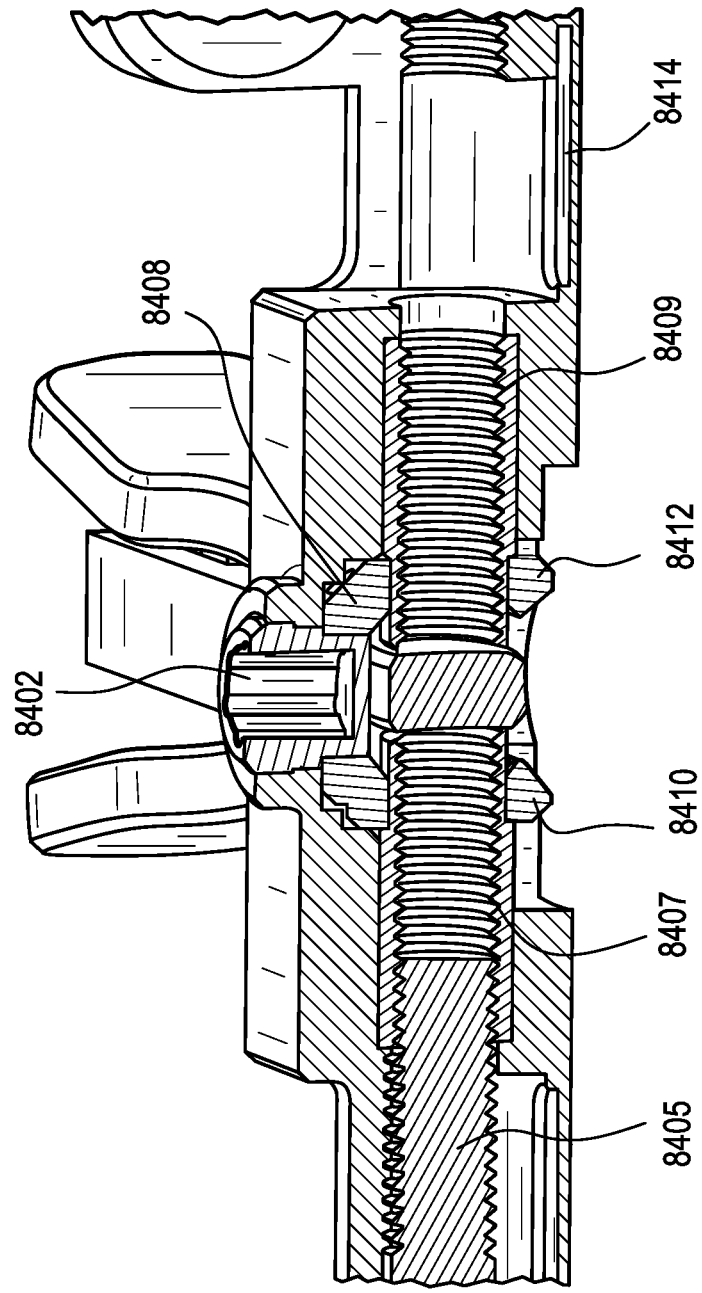
FIG. 86 is a cross-sectional view of the portion of the retractor shown in FIG. 85 taken along the line A-A in FIG. 85.

FIGS. 84-86 illustrate another embodiment of a retractor 8400 that is similar to the retractor 7900 but utilizes a single drive feature 8402 to move both joints 8404, 8406 toward or away from a center thereof. Each joint 8404, 8406 includes a threaded shaft extending therefrom (only the shaft 8405 extending from joint 8406 is shown in the figure). These threaded shafts are received within threaded sockets 8407, 8409 that are coupled to gears 8410, 8412. The gears 8410, 8412 mesh with gear 8408 that is coupled to the single drive feature 8402 such that turning the drive feature can cause rotation of the sockets 8407, 8409 and translation of the joints 8404, 8406 relative to the retractor body 8414. One advantage of the movement mechanisms of the retractors 7900 and 8400 is that there is no need for a separate mechanism to control positional lockout of the joints or to control directionality of the movement of any attachments coupled thereto. The lead screw mechanisms can effectively hold the joints in place when not being actuated and movement direction can be changed by reversing direction of rotation of the drive feature(s).

Figure 87:
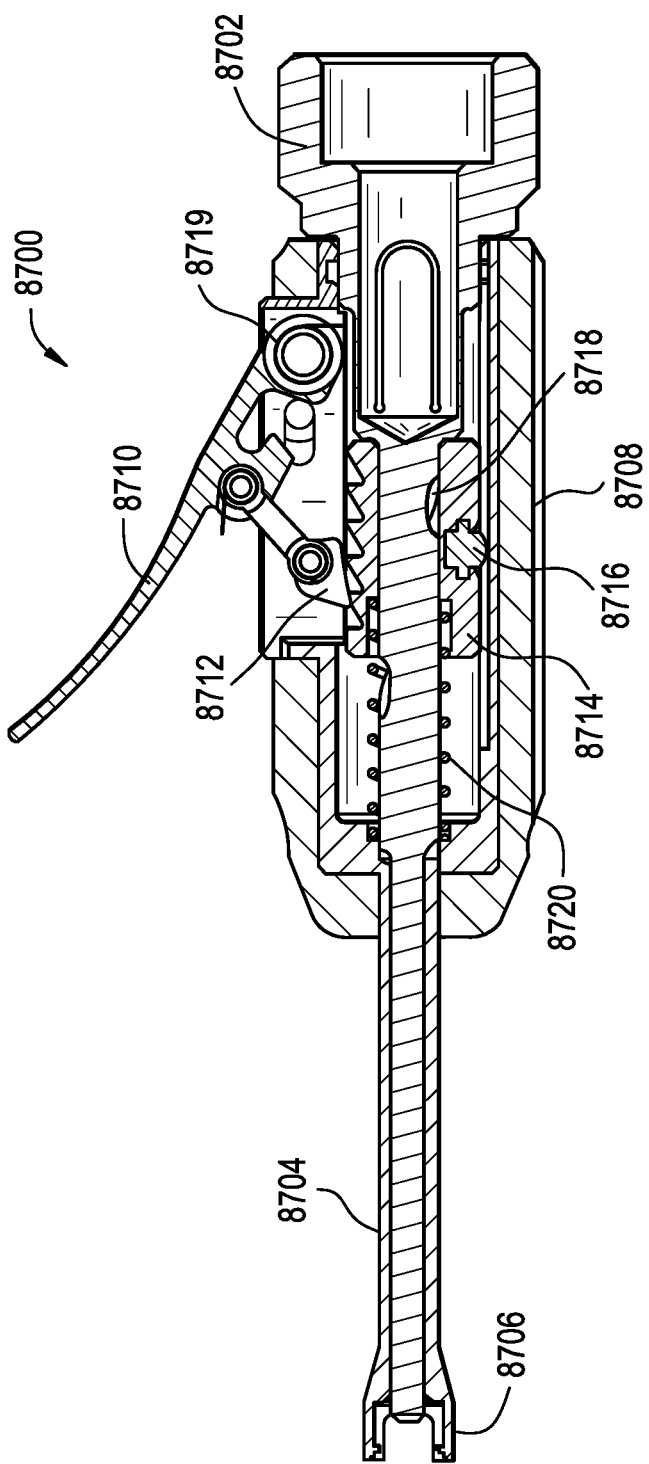
FIG. 87 is a cross-sectional view of another embodiment of an actuating instrument.

FIGS. 87-92B illustrate various embodiments of actuating instruments or drivers that can be used with the retractors and surgical assemblies described herein. FIG. 87 illustrates one embodiment of an actuating instrument 8700 that can be used to lockout a polyaxial joint, such as the joint 212 of the retractor 106 described above. The instrument can function similarly to the driver 1008 described above to rotate the lock 216 of the joint 212, for example. Similar to the driver 1008, the driver 8700 can include a driveshaft 8702 with a distal end configured to be received within a drive feature of the lock 216, and the driveshaft can be disposed within a stabilizing shaft 8704 having a distal end interface 8706 with slots that can receive a portion of the retractor body to provide counterrotating torque when the driveshaft 8702 is rotated. A housing 8708 toward a proximal end of the instrument can include a trigger 8710 that can be depressed to rotate the driveshaft 8702, thereby promoting one-handed use of the instrument 8700. In particular, pulling the trigger 8710 toward the housing 8708 can cause a pawl 8712 to engage a rack 8714 and advance the rack distally relative to the housing 8708 while locking its rotational position. A pin 8716 coupled to the rack 8714 and received within a spiral groove 8718 formed in the driveshaft 8702 can advance distally with the rack. Distal advancement of the rack without rotation can cause rotation of the driveshaft 8702 as the pin rides distally within the spiral groove 8718. Once fully depressed, the trigger 8710 can be released and a biasing element 8719 can urge the trigger away from the housing 8708. This can withdraw the pawl 8712 from the rack 8714, thereby freeing its rotational position and allowing it to return proximally in response to force from the biasing element 8720. As a result, on the return (i.e., proximal-moving) stroke of the rack, the rack can rotate about the stationary driveshaft 8702 and return to a proximal-most position where the trigger can be depressed again to rotate the driveshaft during an advancing (i.e., distal-moving) stroke of the rack. Accordingly, a user can rapidly rotate the driveshaft 8702 by repeatedly depressing and releasing the trigger 8710. This can be especially helpful for initial coarse adjustment or tensioning of the driveshaft 8702. Additional fine adjustment or tensioning can be accomplished by directly rotating a proximal end of the driveshaft 8702 that can protrude proximally from the housing 8708.

Figure 88:
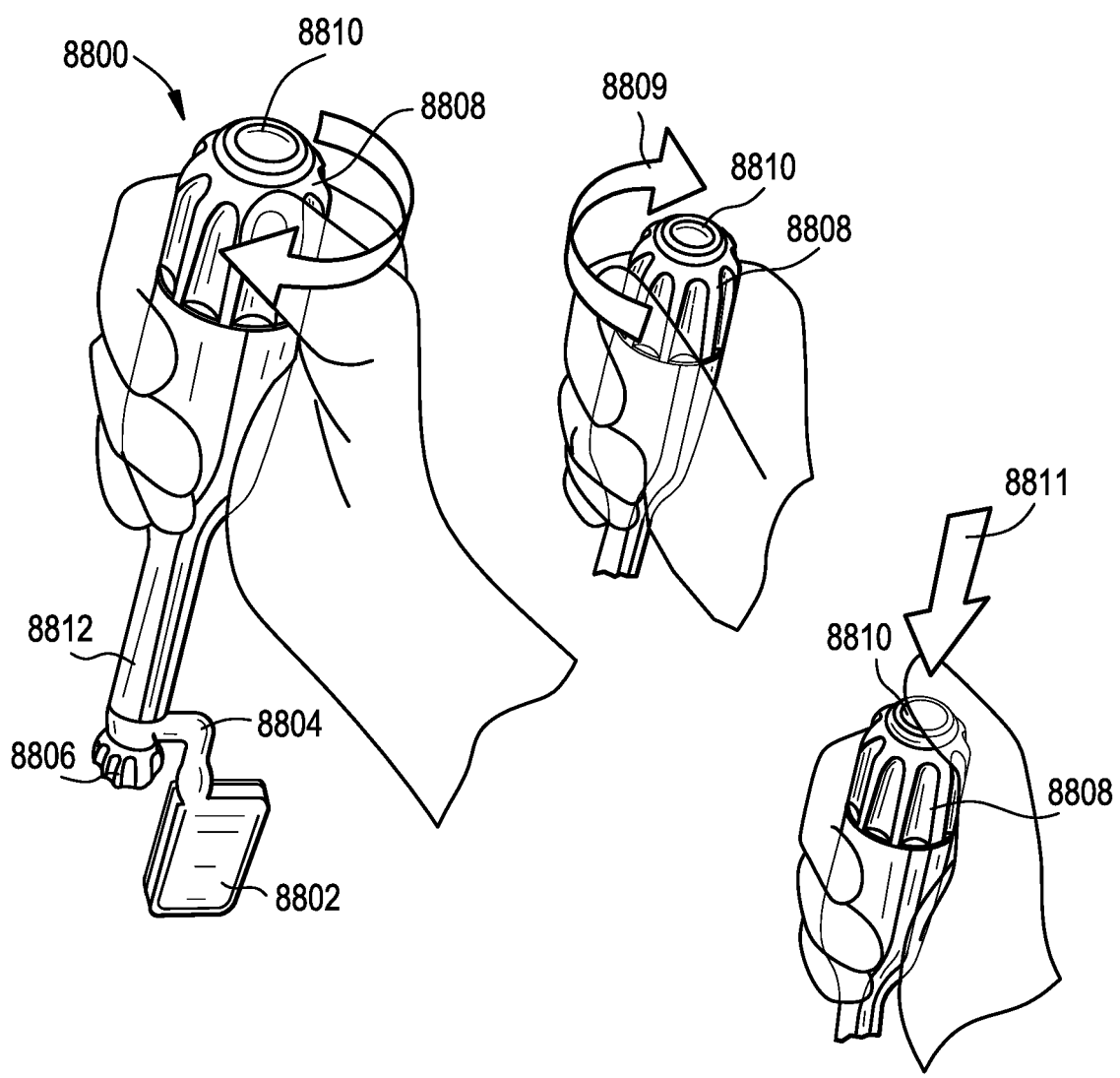
FIG. 88 is a perspective view of another embodiment of an actuating instrument.

FIGS. 88-92B illustrate various embodiments of instruments that can be used to couple tissue manipulating implements to a retractor body. FIG. 88, for example, illustrates one embodiment of an instrument 8800 that can be utilized with one hand to couple to a tissue manipulating implement, position the implement relative to a retractor using a polyaxial joint coupled thereto, lockout the position of the implement via the polyaxial joint, and decouple therefrom. In the illustrated embodiment, a tissue manipulating implement 8802 is coupled to an arm 8804 and an expandable ball 8806 that can be received within a socket in a retractor body, as described above. This assembly is in turn coupled to the actuating instrument 8800 to allow a user to couple the tissue manipulating implement assembly to a retractor and polyaxially move it into a desired position. Once in position, the user can rotate the knob 8808 to expand the ball 8806 and lock the position of the tissue manipulating implement relative to the retractor body (as shown by arrow 8809). Once positioned and locked, the user can depress the button 8810 (as shown by arrow 8811) to detach the instrument 8800 from the tissue manipulating implement assembly. Also shown in the figure is that the instrument 8800 includes a smooth distal stem 8812 that can be grasped by a user's second hand when additional force is needed, e.g., when cobbing or using the tissue manipulating implement to scrape or separate tissue from bone, etc.

Figure 89:
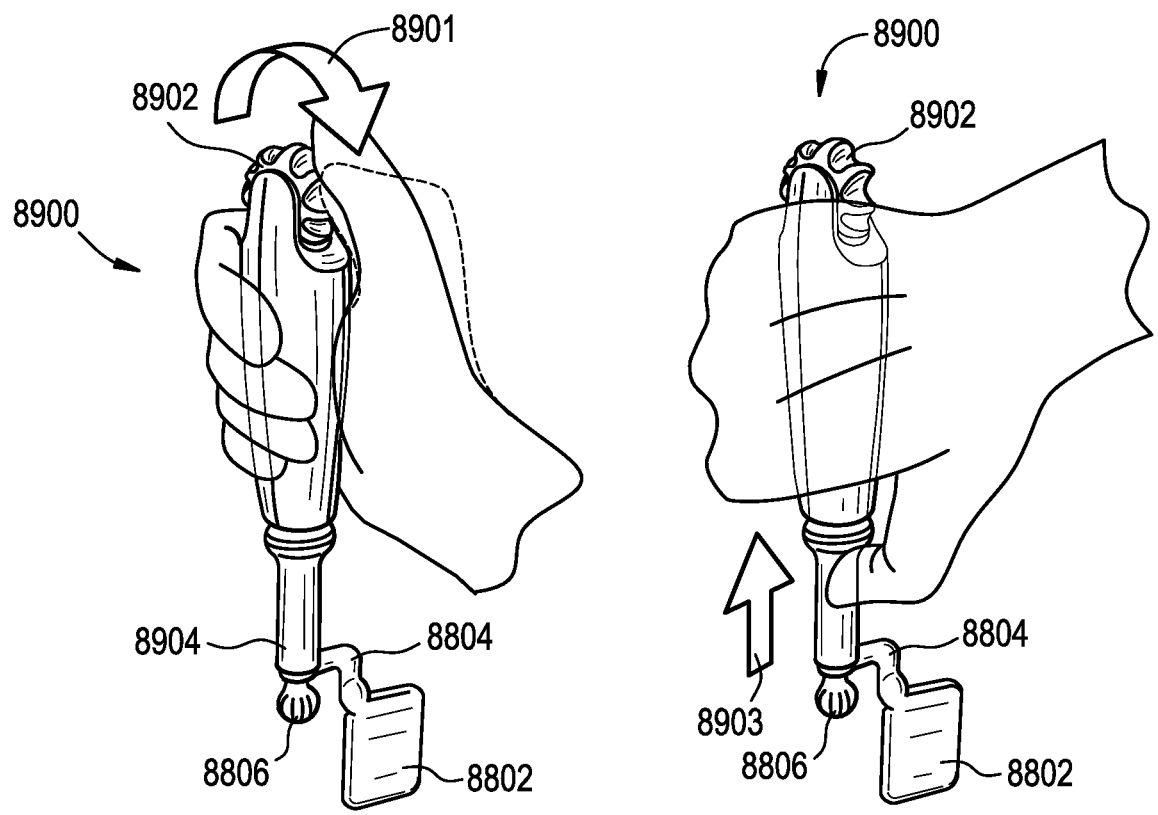
FIG. 89 is a perspective view of another embodiment of an actuating instrument.

FIG. 89 illustrates another embodiment of an actuating instrument 8900. The instrument 8900 is similar to the instrument 8800, but includes a differently oriented lockout actuator and detachment actuator. The illustrated embodiment includes a thumbwheel 8902 oriented to rotate about an axis perpendicular to a longitudinal axis of the instrument 8900 (as shown by arrow 8901), rather than the parallel rotation axis orientation of the instrument 8800. Further, separating the instrument 8900 from the tissue manipulating implement assembly can be accomplished by pulling back a sheath and separating the instrument (as shown by arrow 8903). The instrument 8900 similarly includes a smooth distal stem 8904 to facilitate an extra hand when, e.g., cobbing during a surgical procedure.

Figure 90:
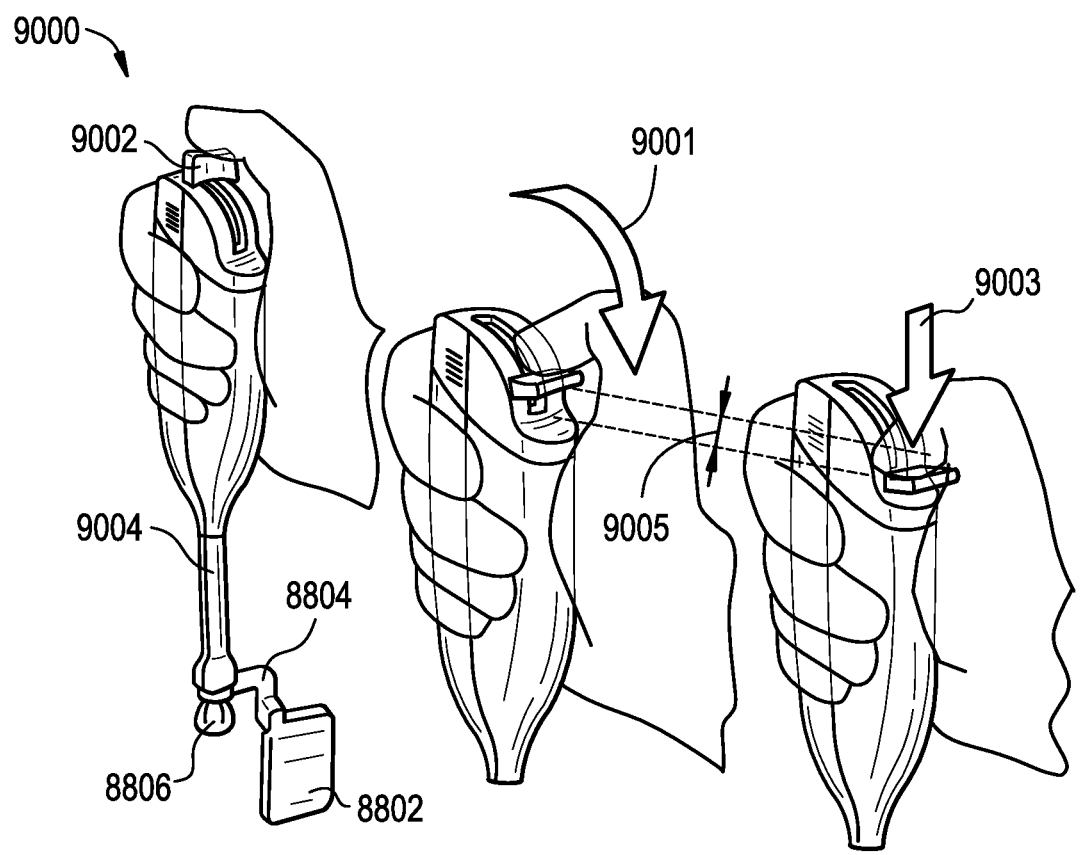
FIG. 90 is a perspective view of another embodiment of an actuating instrument.
Figure 92A:
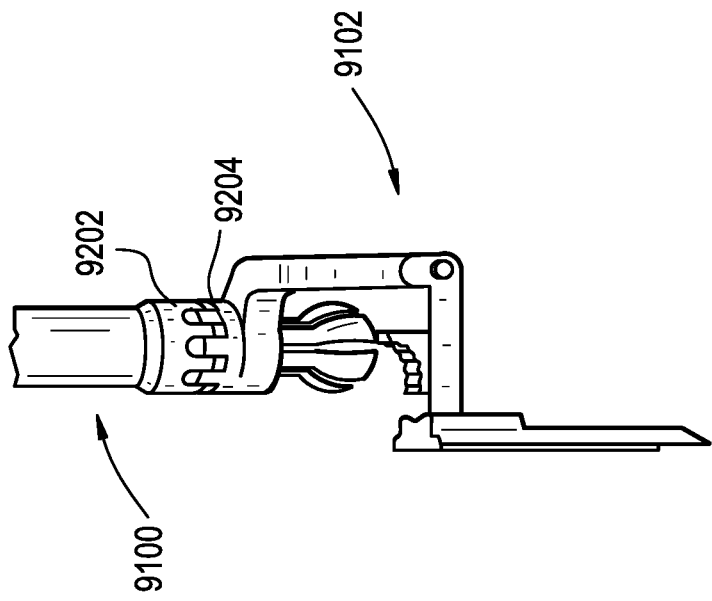
FIG. 92A is a detail view of a distal end of the actuating instrument of FIG. 91A and the tissue manipulating implement of FIG. 91A.
Figure 92B:
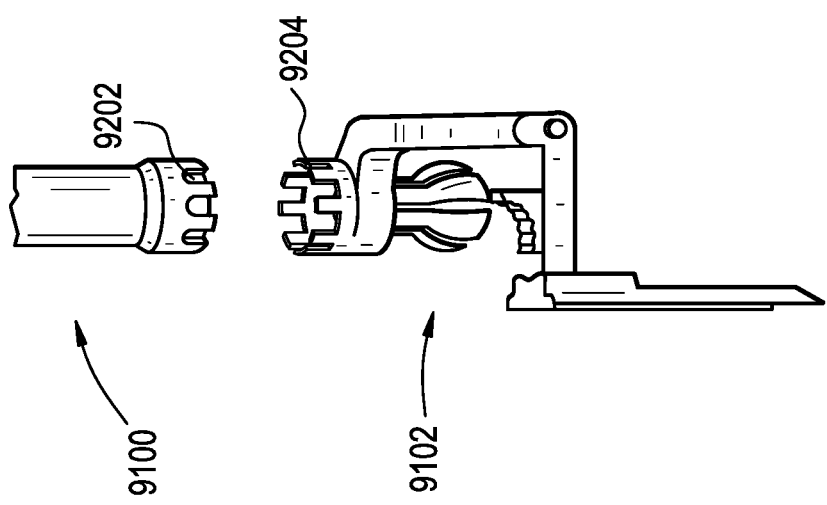
FIG. 92B is a detail view of the portion of the actuating instrument of FIG. 92A coupled to the tissue manipulating implement of FIG. 92A.

FIG. 90 illustrates still another embodiment of an actuating instrument 9000. The instrument is similar to the above-described instruments but utilizes a lever 9002 at a proximal end thereof to control lockout of polyaxial movement of the tissue manipulating implement assembly relative to the retractor body. In particular, a user can depress the lever 9002 in the direction of arrow 9001 to lockout polyaxial movement by expanding the ball 8806 within the socket of the retractor. A detent can signal maximum lockout and detachment of the instrument from the tissue manipulating implement assembly can be achieved by pressing the lever beyond the detent in the direction of arrow 9003 by a distance 9005. The instrument 9000 similarly includes a smooth distal stem 9004 to facilitate an extra hand when, e.g., cobbing during a surgical procedure.

FIGS. 91A-91D illustrate coupling and decoupling of another embodiment of an actuating instrument 9100 to a tissue manipulating implement assembly 9102 that includes a tissue manipulating implement 9104 coupled to an arm 9106 and an expandable ball 9108. To begin, a user can depress the button 9110 at the proximal end of the instrument 9100 in the direction of arrow 9111 to put the instrument in a "load" configuration, as shown in FIG. 91A. The user can then press the instrument 9100 onto the tissue manipulating implement assembly 9102 to couple the two components. This coupling will cause the button 9110 to pop up or proximally, as shown by arrow 9113 in FIG. 91B. The user can then manipulate the position of the assembly 9102 using the instrument 9100 and, once a desired position is reached, the user can expand the ball 9108 to lock the position of the assembly 9102 relative to the retractor body using the thumbwheel 9112. Once positioned and locked, the instrument 9100 can be detached from the assembly 9102 by again pressing the button 9110, as shown by the arrow 9115 in FIG. 91C. Doing so will decouple the instrument from the assembly, as shown in FIG. 91D.

The instrument 9100 can advantageously be utilized entirely single-handedly by a user, who need only grab the instrument and manipulate the button 9110 and thumbwheel 9112 with their thumb. Further, the instrument 9100 can include a castellated feature 9202 formed on a distal end thereof that can be complementary to a castellated feature 9204 formed on a proximal end of the assembly 9102 to allow a user to couple the two components at a variety of rotational orientations relative to one another.

FIGS. 93-101E illustrate one embodiment of a surgical retractor system 9300 according to the teachings provided herein. The system can be used to facilitate retraction of skin, muscle, and other soft tissue to access, for example, various portions of a patient's spine. Further, the system can include a retractor and other components docked via support instruments to a patient's body via, e.g., vertebrae, and as a result can be utilized to perform various procedures, including vertebral distraction, etc.

Figure 93:
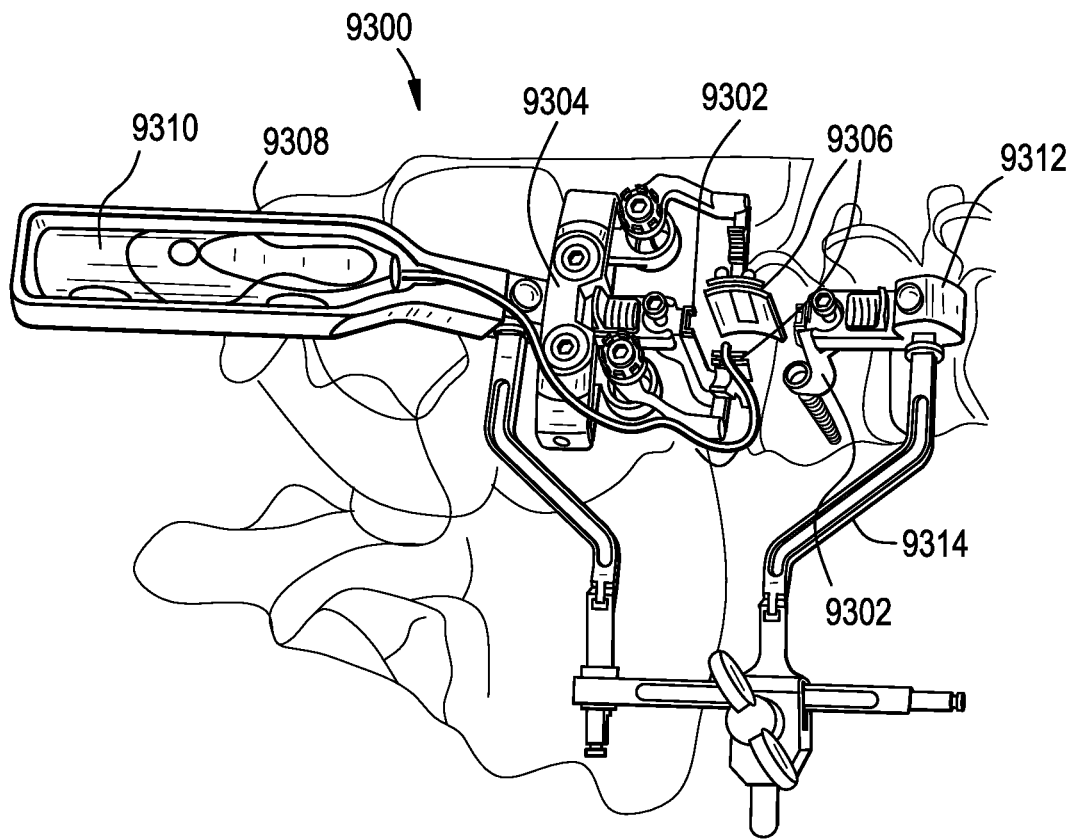
FIG. 93 is a perspective view of one embodiment of a surgical instrument assembly.
Figure 94:
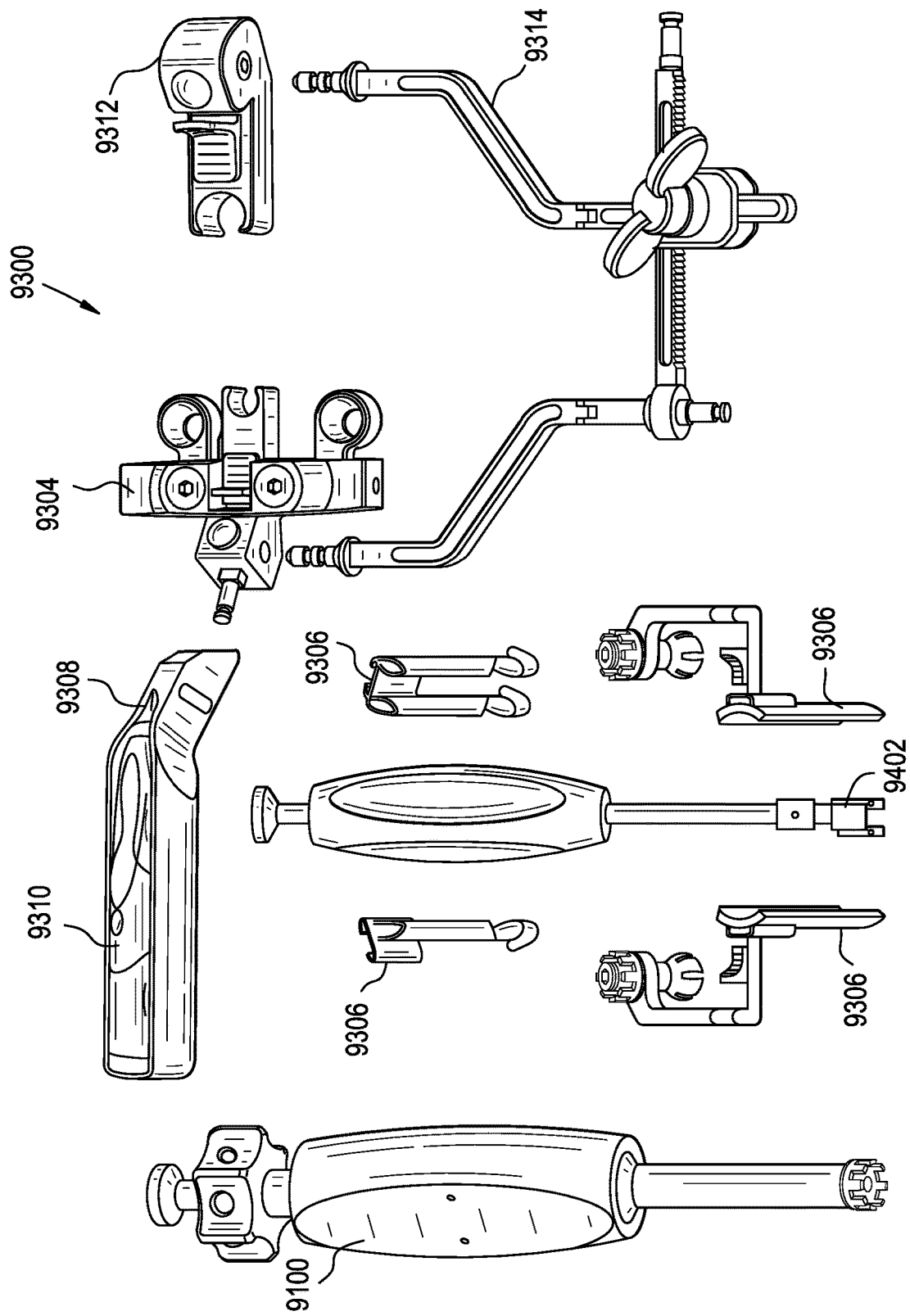
FIG. 94 is an exploded view of the components of the surgical instrument assembly of FIG. 93.
Figure 95A:
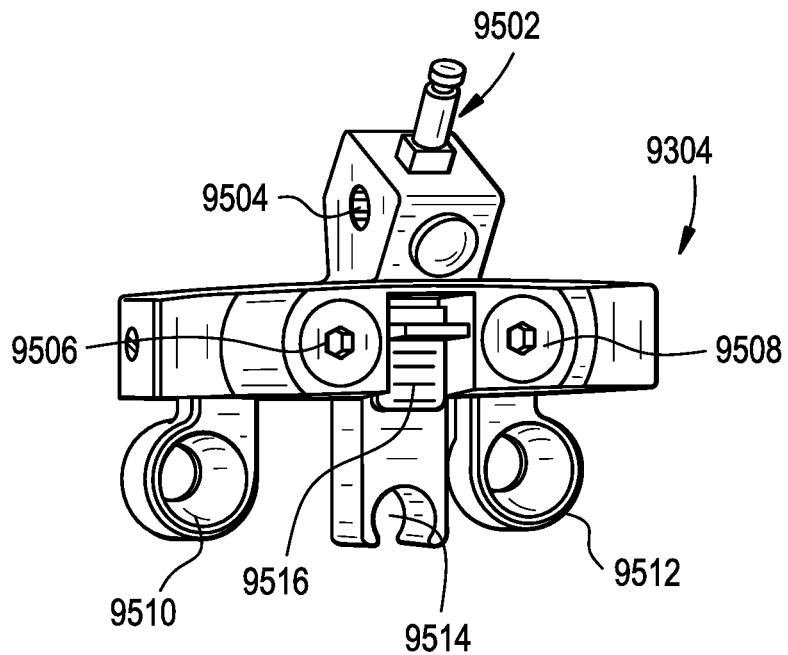
FIG. 95A is a top perspective view of a retractor of the assembly of FIG. 93.
Figure 95B:
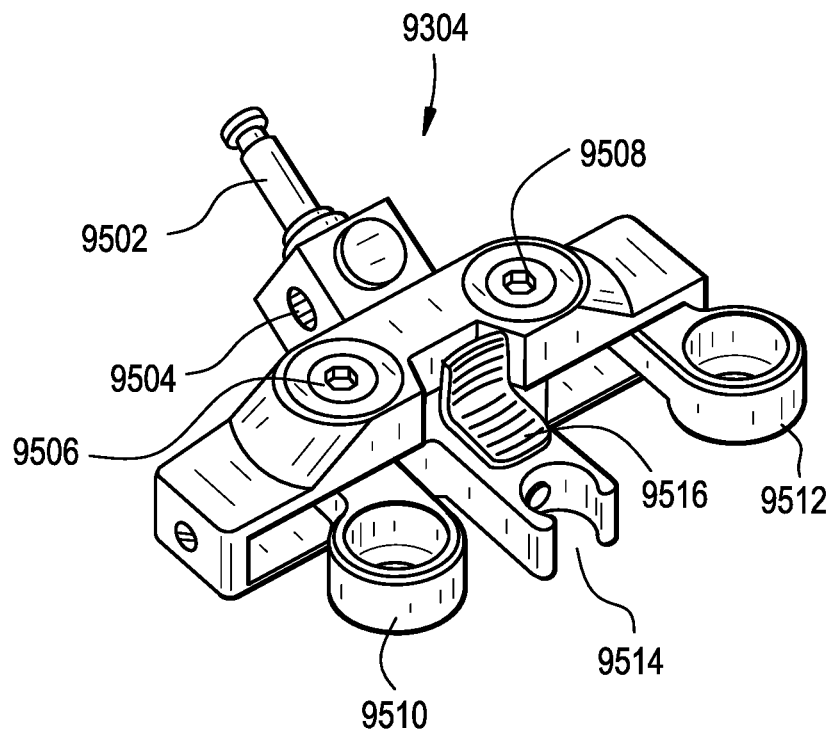
FIG. 95B is a perspective view of the retractor of FIG. 95A.
Figure 95C:
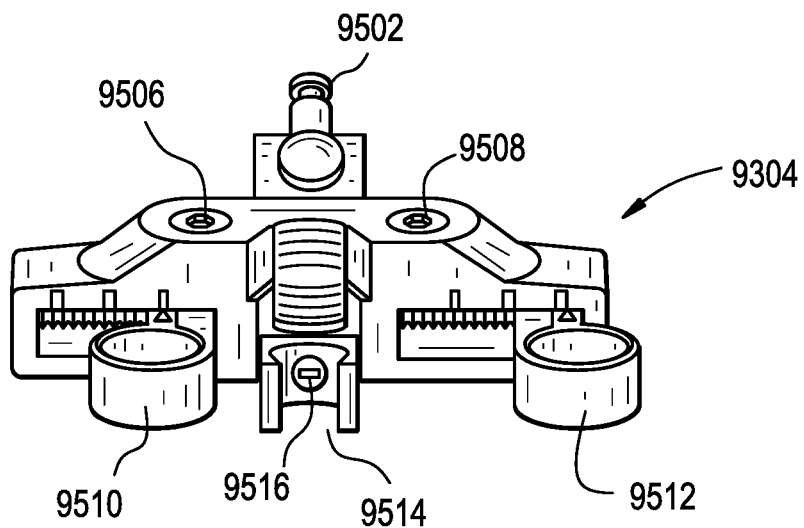
FIG. 95C is a front perspective view of the retractor of FIG. 95A.
Figure 95D:
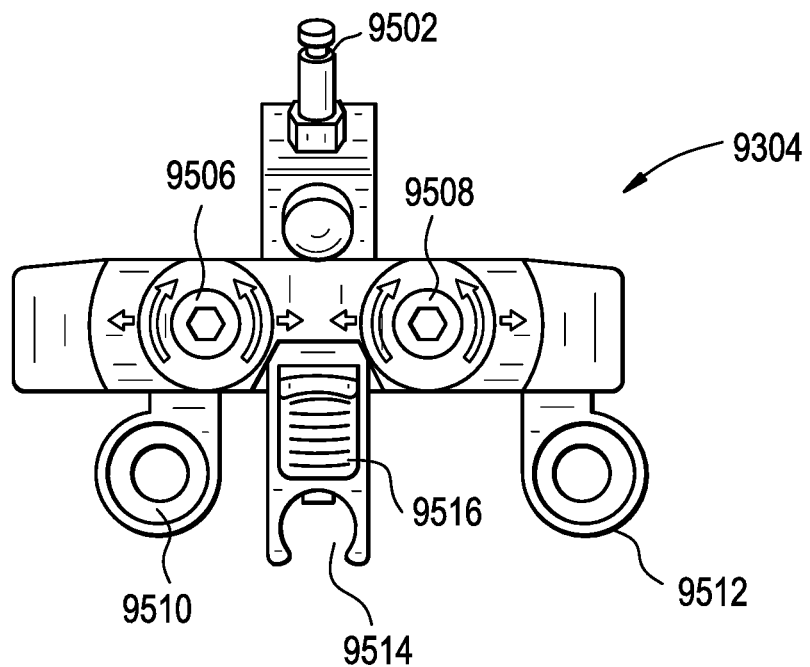
FIG. 95D is a top view of the retractor of FIG. 95A.

As shown by the assembled system of FIG. 93 and the disassembled view of FIG. 94, the system 9300 can include one or more support instruments 9302 coupled to screws implanted in a patient's vertebrae, a retractor 9304 coupled to a support instrument, one or more tissue manipulating implements 9306 coupled to the retractor, a stability handle 9308 with light source 9310 coupled to the retractor 9304, a distraction module 9312 coupled to another support instrument 9302 from the retractor 9304, and a distraction rack 9314 coupled to the retractor 9304 and the distraction module 9312 to perform distraction, e.g., between adjacent vertebrae. Also shown in FIG. 94 is the above-described actuating instrument 9100 that can be used to couple the tissue manipulating implements 9306 to the retractor 9304 and control positioning/locking thereof, as well as a tissue manipulating implement adjuster 9402 that can be utilized to adjust a position, depth, etc. of an expandable tissue manipulating implement, as described herein.

FIGS. 95A-95D illustrate various views of the retractor 9304, which is similar to the other retractor embodiments described herein. For example, the retractor 9304 includes a post 9502 that can be utilized to attach various components thereto, e.g., the stability handle 9308 or a mount coupled to a surgical table, etc. The retractor 9304 also includes a socket 9504 to receive a post on the distraction rack 9314. Further, the retractor 9304 includes drive features 9506, 9508 to independently control translation of tissue manipulating implement sockets 9510, 9512 that can receive expandable balls of tissue manipulating implement assemblies, as described above. Finally, the retractor 9304 includes a recess 9514 and locking feature 9516 for adjusting a position of the retractor along a length of a support instrument received within the recess.

Figure 96:
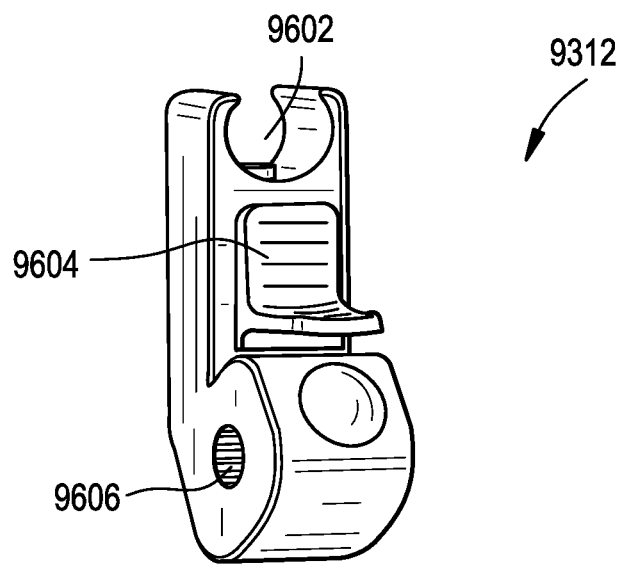
FIG. 96 is a perspective view of a distraction rack coupler of the assembly of FIG. 93.

FIG. 96 illustrates the distraction module 9312 in greater detail. The distraction module includes a recess 9602 and locking feature 9604 similar to the retractor module 9304 to allow the distraction module to be coupled to and adjusted along a length of a support instrument received within the recess. The distraction module also includes a socket 9606 to receive a post formed on the distraction rack 9314.

Figure 97A:
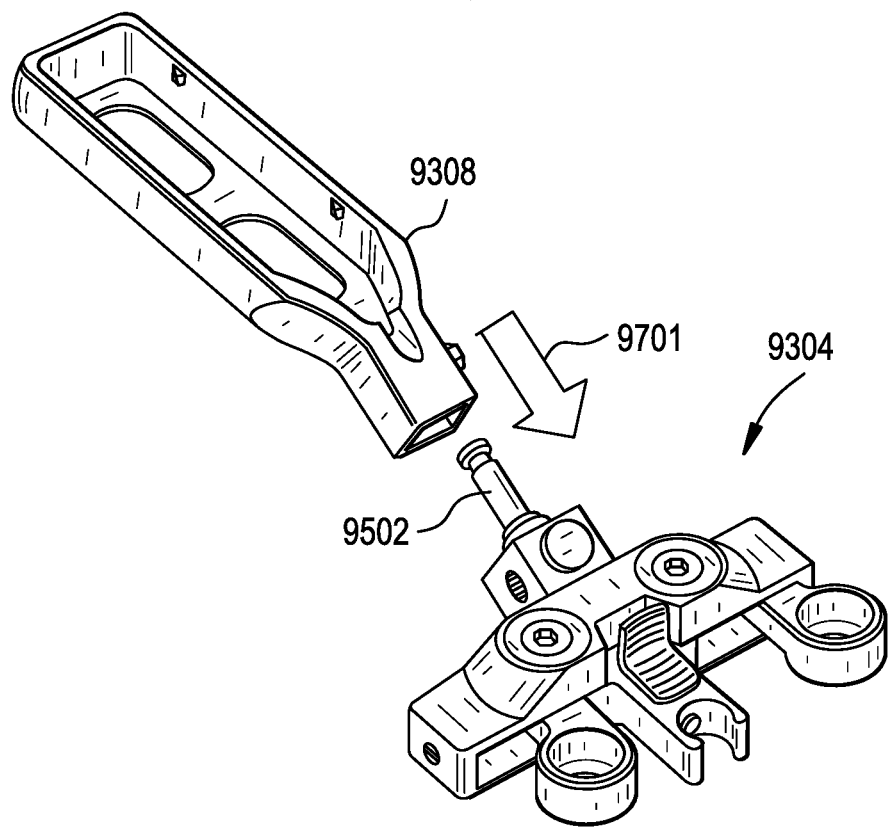
FIG. 97A is a perspective view of a stability handle of the assembly of FIG. 93 coupling to the retractor of the assembly of the FIG. 93.
Figure 97B:
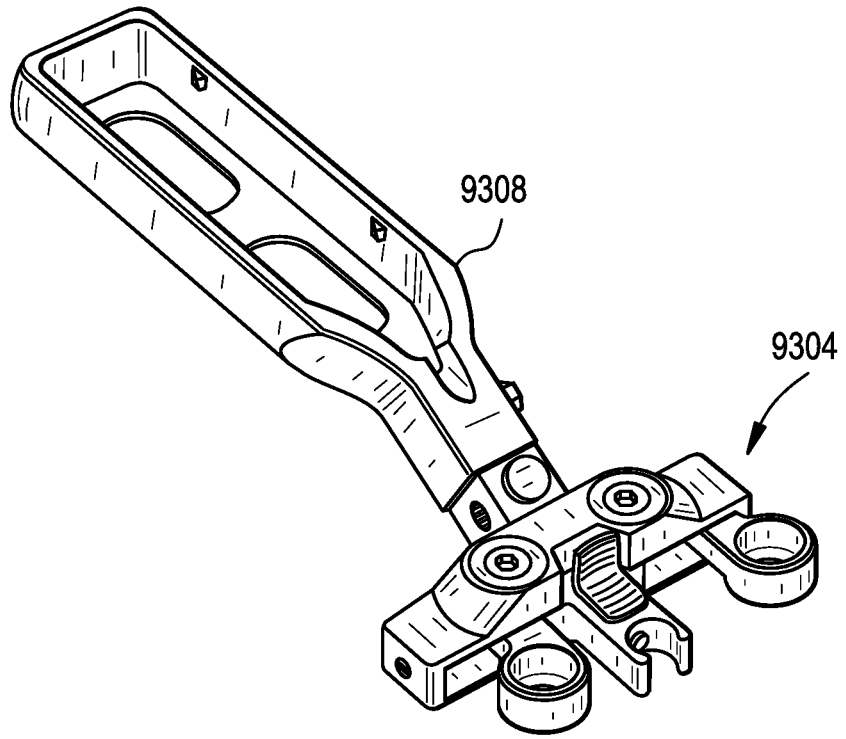
FIG. 97B is a perspective view of the stability handle of the assembly of FIG. 93 coupled to the retractor of the assembly of FIG. 93.
Figure 97C:
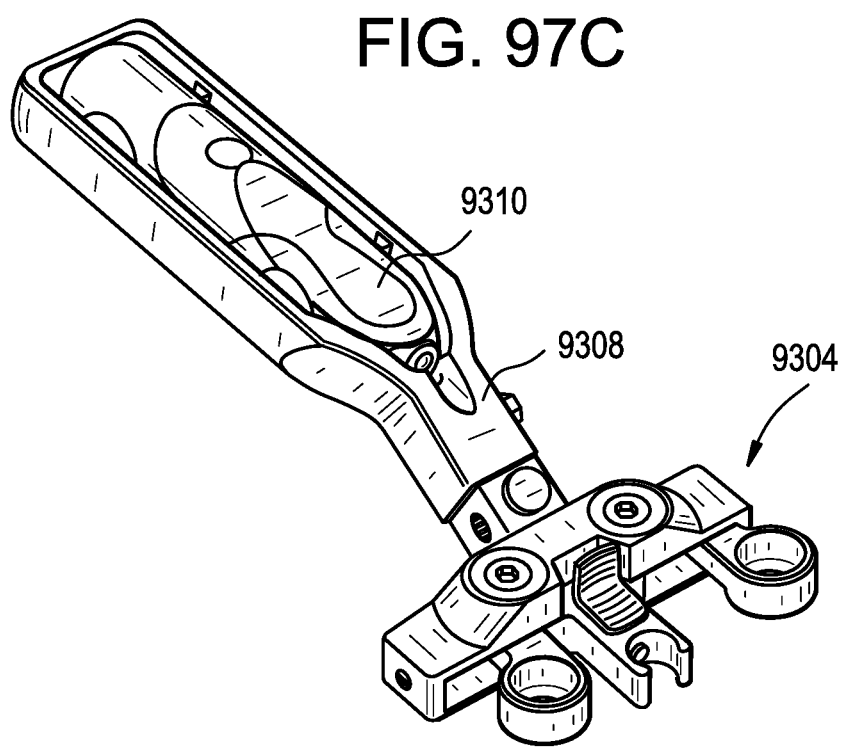
FIG. 97C is a perspective view of a light source of the assembly of FIG. 93 coupled to the stability handle and retractor of the assembly of FIG. 93.

FIGS. 97A-97C illustrate the stability handle 9308 coupled to the retractor 9304 via the post 9502. For example, the stability handle can be slid onto the post 9502 in the direction of arrow 9701 in FIG. 97A to reach the configuration shown in FIG. 97B. The stability handle can be used for added stabilization during tissue manipulating implement positioning, for example. The handle can be utilized alone or, in some embodiments, a light source 9310 can be placed within a recess formed in the stability handle 9308 if additional lighting is desired at the surgical site, as shown in FIG. 97C.

Figure 99A:
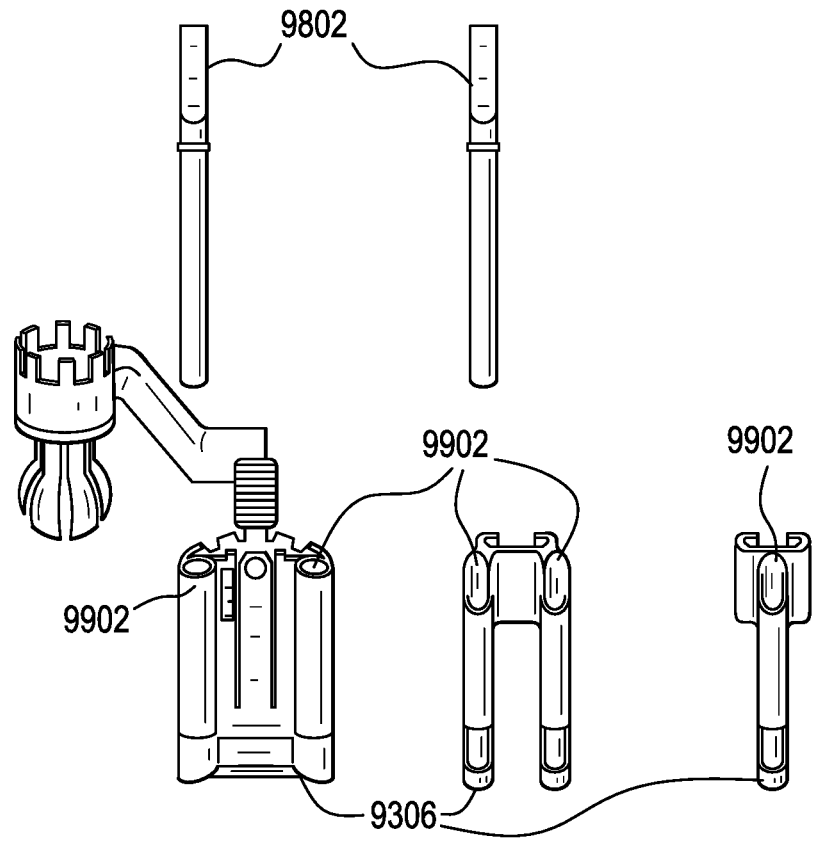
FIG. 99A is a side view of a distal portion of the light source of FIG. 98 aligned with the various tissue manipulating implements of FIG. 98.
Figure 99B:
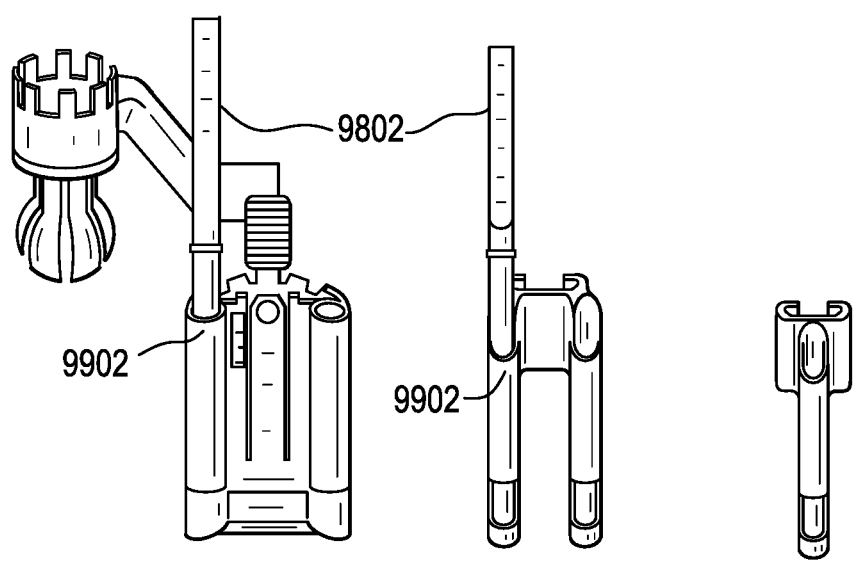
FIG. 99B is a side view of the distal portion of the light source of FIG. 98 coupled to the various tissue manipulating implements of FIG. 98.
Figure 99C:
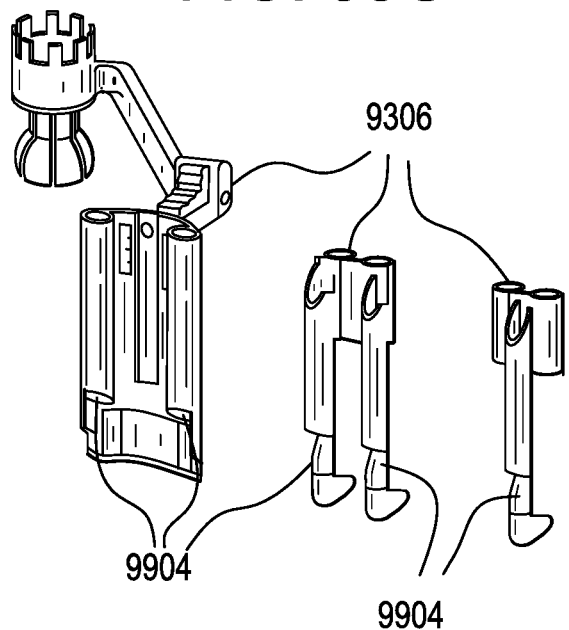

FIG. 98 illustrates the light source 9310 in greater detail. The light source 9310 can, in some embodiments, include a battery or other power source and a light source. In some embodiments, the light source and battery can be disposed in a housing with optical fibers 9802 or other light guides carrying light therefrom. In other embodiments, light sources, such as light emitting diodes, can be disposed separate from a housing containing a battery or other power source and wires 9802 can carry electrical power to the light sources disposed at a distal end of each wire 9802. Further, the leads or optical fibers 9802 can be configured to dock within recesses formed in the various types of tissue manipulating implements that can be coupled to the retractor 9304. FIGS. 99A-99C illustrate various tissue manipulating implements 9306 having recesses 9902 formed therein that are configured to receive leads or optical fibers 9802. Further, and as shown in FIG. 99C, the tissue manipulating implements 9306 can include angled, reflective facets 9904 to direct light into an operative corridor for optimal distribution.

Figure 100A:
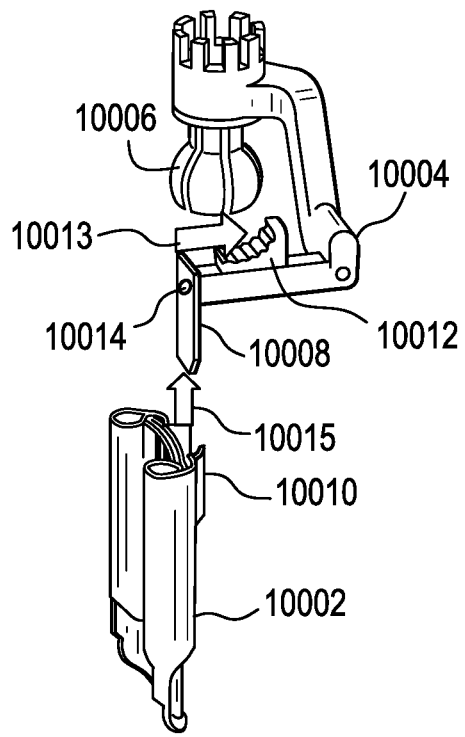
Figure 100B:
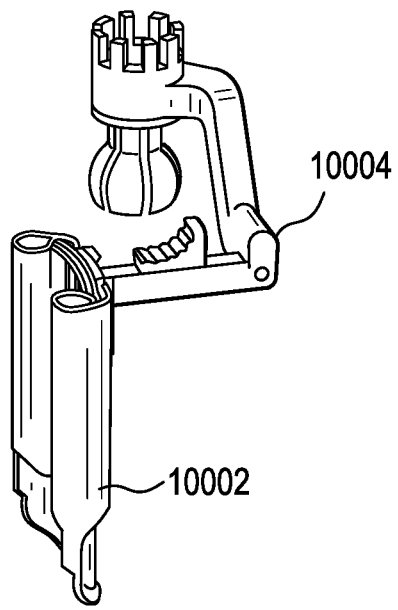

FIGS. 100A and 100B illustrate a modular attachment mechanism for a tissue manipulating implement 10002 and an arm assembly 10004 that includes an expandable ball 10006 that can be received within a socket 9510, 9512 of the retractor 9304. In the illustrated embodiment, the arm assembly 10004 includes a protrusion 10008 that can be received within a slot 10010 formed in the tissue manipulating implement 10002. Further, a translating locking feature 10012 on the arm assembly 10004 can selectively lock the tissue manipulating implement to the arm assembly. As shown in FIG. 100A, coupling a tissue manipulating implement to an arm assembly can include sliding the locking feature 10012 in the direction of arrow 10013 to withdraw the locking pawl 10014 and then sliding the tissue manipulating implement 10002 in the direction of arrow 10015 to position the protrusion 10008 within the slot 10010. Note that while the figure and arrow 10015 indicate a bottom loading configuration in which the implement 10002 is moved upward in the direction of arrow 10015 from below the arm assembly 10004 to couple the two components, a reverse top loading operation is also possible. In such a configuration, the implement 10002 can be lowered onto the protrusion 10008 of the arm assembly 10004 from above. After positioning the two components relative to one another, the locking feature 10012 can be released (in embodiments where it is biased) or slid in an opposite direction into position where the locking pawl 10014 is seated in a detent (not shown) of the tissue manipulating implement to prevent separation of the two components. Decoupling the two components can be accomplished by reversing this procedure. FIG. 100B illustrates the two components coupled and locked to one another.

Figure 101D:
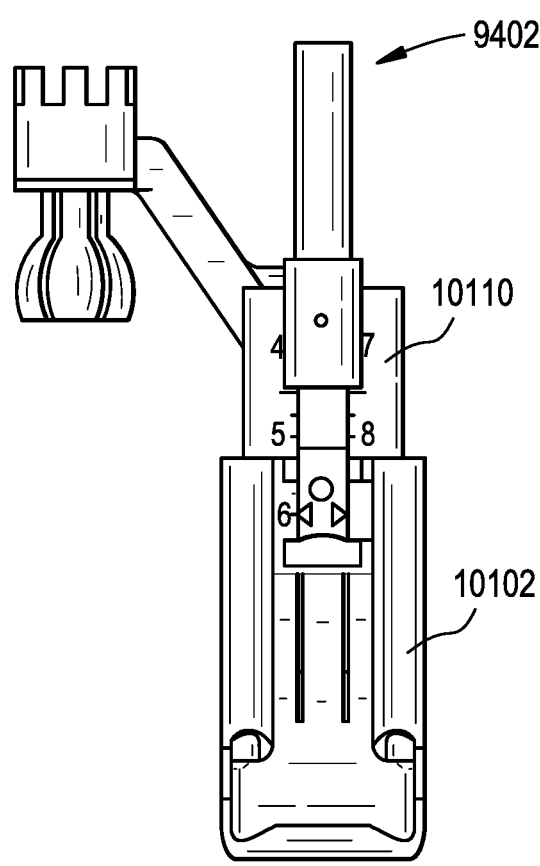
Figure 101E:
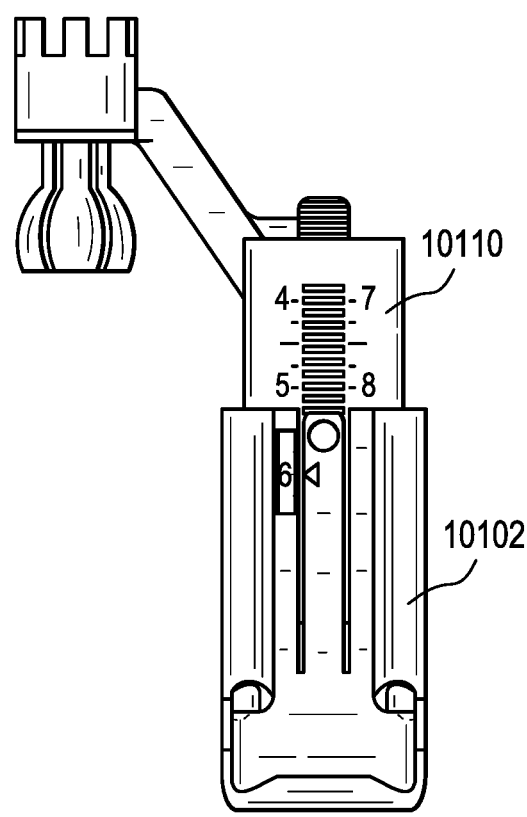

FIGS. 101A-101E illustrate use of the tissue manipulating implement adjuster 9402 that can be utilized to adjust a position, depth, etc. of an expandable tissue manipulating implement 10102. As shown in FIG. 101A, the adjuster 9402 can be coupled to an adjustable or expandable tissue manipulating implement 10102 by aligning dovetail protrusions 10104 with a complementary slot 10106 formed on the implement 10102 and inserting a distal end of the adjuster into the slot 10106. With the expandable implement coupled to the adjuster, a user can depress the button 10108 in the direction of arrow 10109 to retract a spring or other connecting mechanism that can lock the expandable implement to a static tissue manipulating implement 10110 (e.g., as described above with regard to adjustable depth tissue manipulating implements). While depressing the button 10108, the user can slide the expandable implement 10102 along the static implement 10110 to achieve a desired height and then release the button 10108 to lock a position of the expandable implement 10102 relative to the static implement 10110, as shown in FIGS. 101C and 101D. The blade adjuster can then be removed by withdrawing the dovetail protrusions 10104 from the slot 10106 to leave the locked assembly of expandable and static tissue manipulating implements, as shown in FIG. 101E.

In combination with the above-described distraction, any of a variety of surgical procedures can be performed utilizing the working channel provided by the support instrument 7406 and retractor assembly 7410 (or any of the other embodiments of such components described herein). For example, a user can perform a spinal fusion cage insertion procedure via the working channel between the opposed tissue manipulating implements of the retractor assembly 7410. Other exemplary procedures can include disc replacement, discectomy, endplate preparation, bone graft delivery, and the like.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

One skilled in the art will appreciate further features and advantages based on the above-described embodiments. Accordingly, the disclosure is not to be limited by what has been particularly shown and described. All publications and references cited herein are expressly incorporated herein by reference in their entirety.

What is claimed is:

1. A surgical instrument comprising:
   a body configured to couple to an implantable anchor, the body including a plurality of sockets configured to receive and capture a ball to form a ball and socket joint;
   a first tissue manipulating implement including a ball configured to be coupled to the body via one of the plurality of sockets and capable of polyaxial movement relative to the socket when coupled;
   a second tissue manipulating implement including a ball configured to be coupled to the body via one of the plurality of sockets and capable of polyaxial movement relative to the socket when coupled; and
   a lock comprising a deformable expanding member formed at a distal end and disposed inside the ball, the deformable member configured to expand radially to urge a deformable exterior portion of the ball to expand radially outward to selectively lock the ball against movement relative to the socket when coupled
   wherein the first and second tissue manipulating implements are configured to be opposed to one another such that they can move any of toward and away from one another when coupled; and
   wherein each tissue manipulating implement is configured to be coupled to the body with movement of the ball into one of the plurality of sockets of the body.

2. The instrument of claim 1, further comprising an anchor extension extending between the body and the implantable anchor.

3. The instrument of claim 2, further comprising a lock body coupled to the body and configured to interface with the anchor extension to selectively lock a position of the body relative to the anchor extension.

4. The instrument of claim 3, wherein the lock body includes a pawl configured to move relative to the body and configured to interface with a ratchet formed on an anchor extension.

5. The instrument of claim 1, wherein at least one of the tissue manipulating implements is a planar blade.

6. The instrument of claim 5, wherein the tissue manipulating implements include a first blade and a second blade configured to translate relative to one another to adjust an overall length of the tissue manipulating implement.

7. The instrument of claim 5, wherein at least one of the tissue manipulating implements includes a distal tip configured to scrape tissue from bone.

8. The instrument of claim 1, wherein at least one of the tissue manipulating implements includes a pointed distal tip.

9. The instrument of claim 1, further comprising an extension post coupled to the body.

10. The instrument of claim 9, wherein the extension post pivots relative to the body.

11. The instrument of claim 1, wherein polyaxial movement of the tissue manipulating implements relative to the body includes toeing of a distal end of the tissue manipulating implements any of toward and away from one another.

* * * * *